(12) United States Patent
Watanabe et al.

(10) Patent No.: US 7,176,459 B2
(45) Date of Patent: Feb. 13, 2007

(54) ELECTRON BEAM APPARATUS

(75) Inventors: Kenji Watanabe, Kanagawa-ken (JP); Tohru Satake, Kanagawa-ken (JP); Mamoru Nakasuji, Kanagawa-ken (JP); Takeshi Murakami, Tokyo (JP); Tsutomu Karimata, Kanagawa-ken (JP); Nobuharu Noji, Kanagawa-ken (JP); Keiichi Tohyama, Kanagawa-ken (JP); Masahiro Hatakeyama, Kanagawa-ken (JP)

(73) Assignee: Ebara Corporation, Tokyo (JP)

( * ) Notice: Subject to any disclaimer, the term of this patent is extended or adjusted under 35 U.S.C. 154(b) by 25 days.

(21) Appl. No.: 10/999,124

(22) Filed: Nov. 30, 2004

(65) Prior Publication Data

US 2005/0253066 A1    Nov. 17, 2005

(51) Int. Cl.
*H01J 37/28* (2006.01)
*G01N 23/225* (2006.01)

(52) U.S. Cl. .................. 250/310; 250/311; 250/306
(58) Field of Classification Search ................. 250/310
See application file for complete search history.

(56) References Cited

U.S. PATENT DOCUMENTS

| 6,265,719 | B1* | 7/2001 | Yamazaki et al. .......... 250/310 |
|---|---|---|---|
| 6,385,292 | B1* | 5/2002 | Dunham et al. ............. 378/122 |
| 6,765,217 | B1* | 7/2004 | Nishimura et al. ....... 250/491.1 |
| 2002/0036264 | A1* | 3/2002 | Nakasuji et al. ............. 250/306 |
| 2004/0183013 | A1* | 9/2004 | Nakasuji et al. ............. 250/310 |
| 2005/0121611 | A1* | 6/2005 | Kimba et al. ................ 250/311 |
| 2005/0194535 | A1* | 9/2005 | Noji et al. ................... 250/311 |

FOREIGN PATENT DOCUMENTS

JP    11-283548    * 3/1998

* cited by examiner

*Primary Examiner*—Nikita Wells
*Assistant Examiner*—James J. Leybourne
(74) *Attorney, Agent, or Firm*—Westerman, Hattori, Daniels & Adrian, LLP.

(57) ABSTRACT

An electron beam apparatus is provided for evaluating a sample at a high throughput and a high S/N ratio. As an electron beam emitted from an electron gun is irradiated to a sample placed on an X-Y-θ stage through an electrostatic lens, an objective lens and the like, secondary electrons or reflected electrons are emitted from the sample. The primary electron beam is incident at an incident angle set at approximately 35° or more by controlling a deflector. Electrons emitted from the sample is guided in the vertical direction, and focused on a detector. The detector is made up of an MCP, a fluorescent plate, a relay lens, and a TDI (or CCD). An electric signal from the TDI is supplied to a personal computer for image processing to generate a two-dimensional image of the sample.

12 Claims, 51 Drawing Sheets

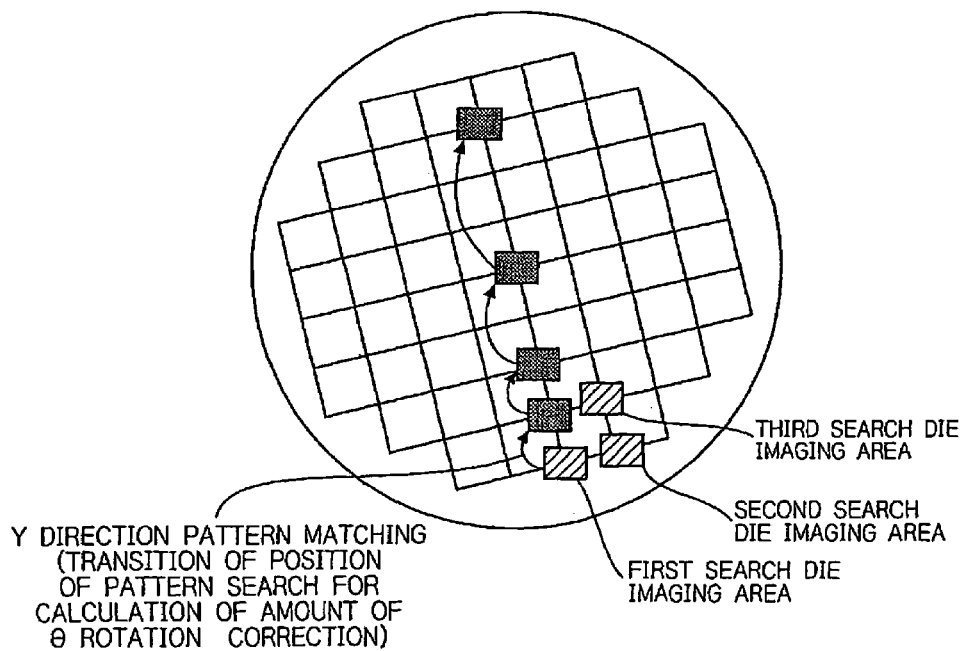

DIE MAP PICTUE

16 DOTS

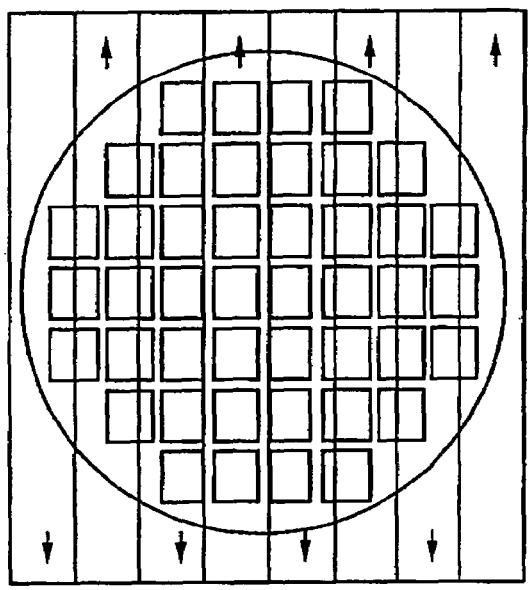 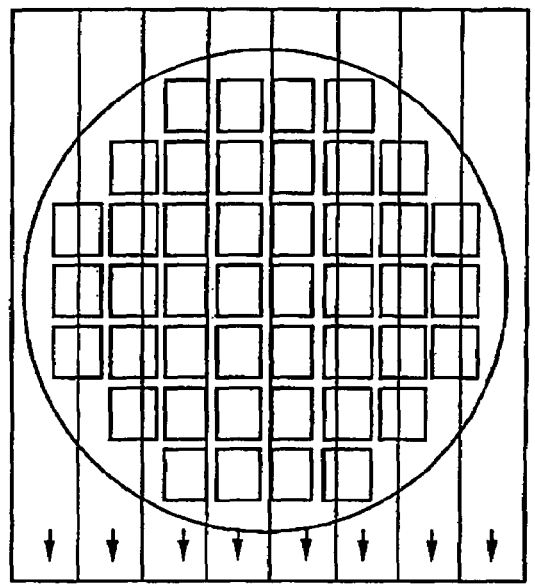
Fig. 44 (A)  Fig. 44 (B)
OPERATION A  OPERATION B

118·1

118·2

118·3

ELECTRON BEAM APPARATUS

BACKGROUND OF THE INVENTION

The present invention relates to an electron beam apparatus for testing (or inspecting), observing, and evaluating the surface of a sample such as a semiconductor wafer for structure, electric conduction and the like, and more particularly, to an electron beam apparatus which can accurately and reliably evaluate a pattern formed on a sample with a minimum line width of 0.15 µm or less at a high throughput.

Conventionally, electron beam apparatuses have been known to irradiate an electron beam onto the surface of a semiconductor wafer, which is a sample under testing, for scanning to detect secondary electrons emitted from the wafer, generate image data of the surface of the wafer from captured signals indicative of the detected secondary electrons, and detect whether the image data matches or does not match each of dies on the wafer to detect defects on the wafer.

Such an electron beam apparatus also includes a projection imaging electron beam apparatus. The projection imaging electron beam apparatus forms an enlarged image from secondary electrons emitted from the surface of a wafer irradiated with a primary electron beam or electrons reflected from the same using a multi-stage lens system such as an objective lens. Since the projection imaging electron beam apparatus is capable of evenly irradiating an electron beam to a relatively large area on the surface of a sample, tests can be conducted at a higher throughput than that obtained using a SEM-based electron beam apparatus.

Japanese Patent Public Disclosure (Kokai) No. 11-283548 describes a projection imaging electron beam apparatus which directs a plurality of primary electron beams onto a sample from an inclined direction.

While the projection imaging electron beam apparatuses are typically capable of conducting tests at a relatively high throughput as described above, the following problems are implied in the projection imaging electron beam apparatuses.

When reflected electrons, rather than secondary electrons, are detected by a projection imaging electron beam apparatus, a test cannot be conducted at a desired throughput in some cases because a number of reflected electrons emitted from the surface of a sample is approximately 1/100 that of secondary electrons.

In some prior art examples, an ExB deflector is used to separate a primary electron beam from emitted electrons (secondary electrons or reflected electrons), but the use of the ExB deflector disadvantageously results in increased color aberration caused by energy diffusion of the secondary electrons or reflected electrons within an electric field and a magnetic field. Further, when a primary electron beam is directed using an ExB deflector, a resulting image is more susceptible to blur due to a spatial charge effect if primary electrons travel along an optical path close to that of secondary electrons.

Further, the apparatus described in Laid-open Japanese Patent Application No. 11-283548 directs a plurality of primary electron beams onto a sample in an inclined direction between an objective lens for enlarging or focusing emitted electrons and the surface of a sample, so that the emitted electrons are deflected by a draw-out electric field (an electric field for guiding emitted electrons toward a secondary optical system) to cause an exit angle to largely incline from the optical axis, resulting in a reduction in the number of emitted electrons per incident electron. Thus, this apparatus may fail to conduct a test at a desired throughput as well. Also, when a sample has ruggedness on the surface, the resulting image tends to include shading.

SUMMARY OF THE INVENTION

The present invention has been made in view of the problems encountered in the prior art examples as described above, and it is an object of the invention to provide a projection imaging electron beam apparatus which is capable of evaluating the surface of a sample at a high throughput and a high S/N ratio.

To achieve the above object, the present invention provide an electron beam apparatus for evaluating a surface of a sample by detecting electrons having information on the sample surface generated by irradiation of a primary electron beam to the sample, which comprises:

an electron gun for generating an electron beam;

a primary opto-electro system for directing at least one primary electron beam to the sample surface in an inclined direction;

an objective lens disposed near the sample for passing therethrough the primary electron beam and electrons having information on the sample surface; and a detector for detecting the electrons having information on the sample surface.

In the electron beam apparatus according to the present invention, it is preferable that the primary opto-electro system is adapted to simultaneously direct a plurality of primary electron beams toward an observation spot on the sample surface, or the primary opto-electro system is adapted to axially symmetrically irradiate a plurality of primary electron beams toward an observation spot on the sample surface. Further, it is preferable that the primary opto-electro system is adapted to simultaneously direct a plurality of primary electron beams toward the sample surface, wherein at least one of the primary electron beams is directed in front of the observation spot in a scanning direction for pre-charge irradiation. In addition, preferably, the detector is located on a line perpendicular to the sample surface.

Also preferably, in the electron beam apparatus according to the present invention described above, the primary opto-electro system comprises a deflector for setting an incident angle of the primary electron beam into the sample surface by controlling a magnetic field or an electric field, and the deflector is formed in a fan or sector shape. The primary opto-electro system preferably includes means for setting an incident angle of the primary electron beam in a range of 35°–90°, preferably in a range of 55°–90°, and optimally an a range of 70°–90°.

Further, in the electron beam apparatus according to the present invention, the primary opto-electro system preferably includes means for forming a crossover on an optical axis of a secondary opto-electro system before irradiating the primary optical beam onto the sample surface, and preferably the primary opto-electro system comprises a lens column including an electrostatic lens which has a plurality of electrodes made by plating on an inner surface of a ceramic. It is preferable that the electron gun comprises a cathode using a cold cathode source made of a carbon nano tube or the like.

Moreover, it is preferable that the electron beam apparatus according to the present invention further comprises a sample stage having an electrostatic chuck for holding the sample through absorption; and voltage applying means for applying the sample with a retarding voltage. In this electron beam apparatus, the electrostatic chuck preferably comprises an ampere meter for confirming that the sample is in a conducting condition before the retarding voltage is applied to the sample.

The present invention also provides a semiconductor device manufacturing method which includes the step of evaluating a wafer in the middle or after completion of a process using the electron beam apparatus described above.

Since the present invention is configured as described above, it can provide the following advantageous effects.

(1) Since the primary electron beam is irradiated to a sample through the objective lens near the sample, a relatively high count of electrons can be emitted per primary electron incident thereon, thus making it possible to prevent a reduction in the number of emitted electrons, as experienced in the prior art example, to improve the throughput and SIN ratio.

(2) When a sufficient number of electrons are emitted from a sample with only one electron beam irradiated to the sample, simultaneous irradiation of a plurality of primary electron beams can cause distorted images due to charge-up or the like, as is the case with an imaging projection type for detecting secondary electrons. However, the remaining primary electron beams are irradiated to the sample at a shifted location such that the sample is pre-charged, thereby preventing the charge-up.

(3) When a plurality of primary electron beams are simultaneously irradiated to an observation spot from inclined directions which are axially symmetric to each other, no shades result even if a sample has ruggedness on the surface, thus improving the S/N ratio.

(4) Electrons (secondary electrons or reflected electrons) emitted from a sample are detected by a detector which is disposed vertically with respect to the surface of the sample, and therefore the electrons are directed straight, instead of being deflected, so that no aberration will occur.

(5) For controlling the incident angle of the primary electron beam, a fan-shaped (sector type) deflector using a magnetic field or an electric field is disposed around the optical axis, thus permitting the primary electron beams to be incident on the surface of the sample at an angle close to a right angle. When the primary electron beams are incident on the sample at an incident angle of approximately 35° or more, an increased amount of electrons are emitted from the surface of the sample in the vertical direction, so that an increased number of electrons can be detected in connection with the incident beams, thereby making it possible to conduct a low-loss evaluation and test or inspection.

(6) With the use of a fan-shaped deflector in the primary opto-electro system, even if the detector is disposed on the vertical line to a sample, the detector does not interfere with the optical axis which extends in the vertical direction from the sample, so that secondary electrons emitted from the sample or reflected electrons can be passed through the detector.

(7) While the use of an ExB deflector has a disadvantage of increasing chromatic aberration caused by energy dispersion of the secondary electrons or reflected electrons within an electric field or a magnetic field, the electron beam apparatus of the present invention does not employ the ExB deflector, thus eliminating the need for controlling the primary electron beams in consideration of the increase in chromatic aberration.

(8) When a quadruple (QL) lens or the like is employed in the primary opto-electro system to form a crossover on the optical axis before irradiation in order to converge a plurality of primary electron beams for irradiation onto a sample, it is possible to reduce a loss due to an opening formed by extended electron beams and collision of electrons onto the inner wall of a column. "Column" generally refers to a lens column which forms part of the primary electron system, and is a generic name for electrodes, ceramic insulators and the like. The position of the crossover may be set to lie on an optical trajectory near the intersection of the primary electron beams with secondary electron beams (i.e., the center position when an ExB deflector is used as in the prior art), particularly when reflected electrons from the sample are detected, thus making it possible to irradiate more primary electrons to the surface of the sample.

(9) When electron beam generators are arranged in multiple stages, an increased amount of current can be applied from the primary electron beams to the sample. In this event, even upon replacement of a cathode or the like due to the expiration of lifetime, the replacement can be performed while the electron beam apparatus (electron gun and primary opto-electro system) is in operation.

(10) A plurality of electrodes which make up the electrostatic lens included in the primary opto-electro system are formed of integral ceramic having its inner surface plated, thereby reducing the size and weight of the overall electron beam apparatus.

(11) The electron gun can emit beams at improved luminance and extend the lifetime by use of a cold cathode type emitter such as a carbon nano tube for the electron gun.

BRIEF DESCRIPTION OF THE DRAWINGS

FIGS. 1(A) to 1(C) are graphs showing incident angle dependence of emitted electrons for explaining the principles of the present invention;

FIG. 31-2 is a diagram for explaining the configuration and operational procedure subsequent to the operation in FIG. 31-1 of the elevator mechanism in the load lock chamber shown in FIG. 21;

FIG. 35 is a die map showing how dies are arranged after alignment of the wafer;

FIG. 36 is a diagram for explaining a coordinate value update in a wafer alignment procedure;

FIGS. 44(A) and 44(B) are diagrams each for explaining the semiconductor device inspection procedure;

DETAILED DESCRIPTION OF THE INVENTION

Before describing preferred embodiments of an electron beam apparatus according to the present invention, description will be made on aspects that are taken into consideration by the present invention.

Figure 1:
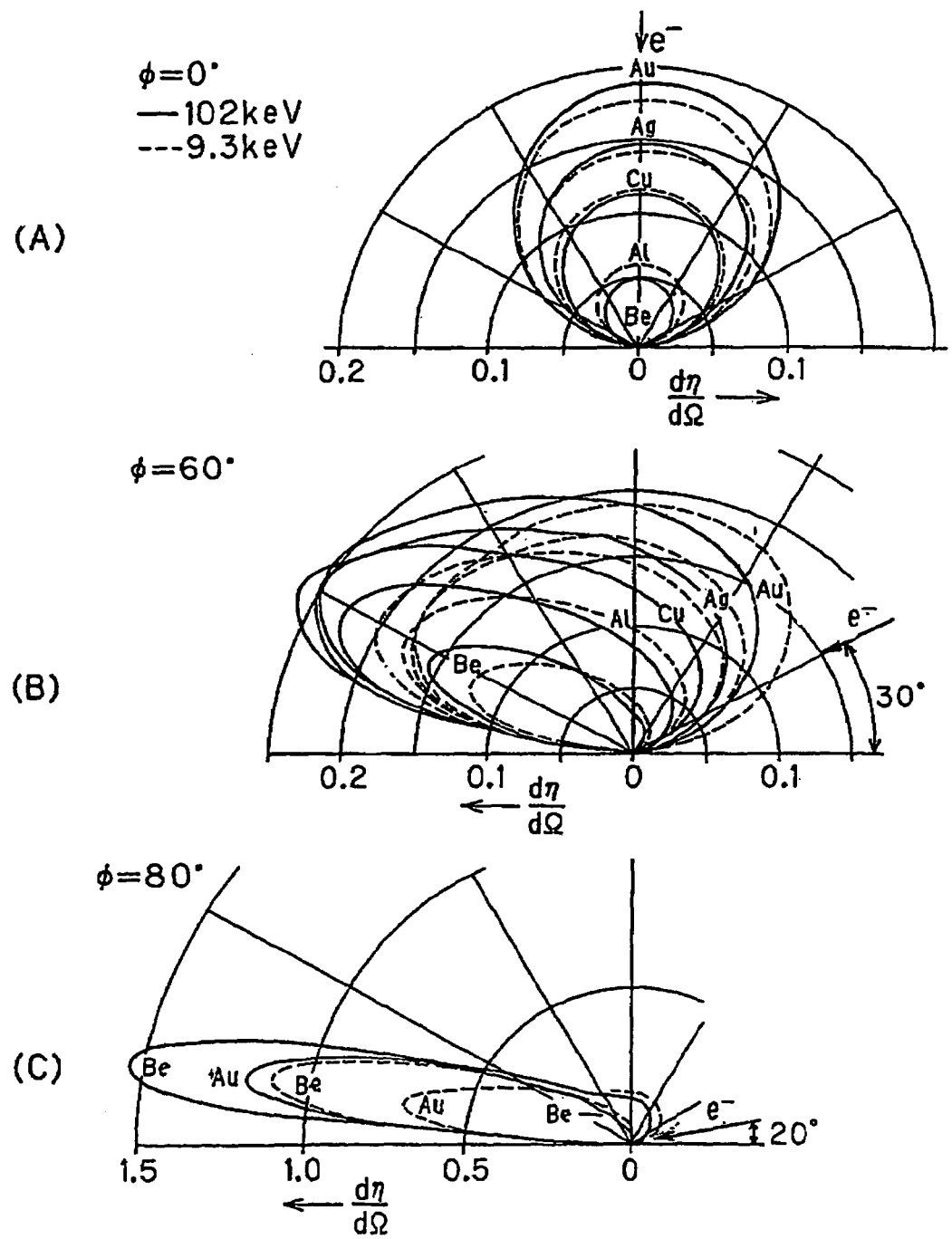
FIG. 31-1 is a diagram for explaining the configuration and operational procedure of an elevator mechanism in a load lock chamber shown in FIG. 21.

FIG. 1 shows the incident angle dependence characteristic of a back scattering coefficient of electrons emitted from a sample, which is described in "Electron Beam Testing Handbook" (Electron Beam Research, Vol. 7). Here, the incident angle refers to the angle formed by the optical axis of a primary opto-electro system to the surface of the sample. FIGS. 1(A)–1(C) show the incident angle dependence characteristic when the incident angle θ is 90°, 60°, and 80°, respectively. Also, in these graphs, solid lines indicate the characteristic when the energy is equal to 100 keV, while dotted lines indicate the characteristic when the energy is equal to 9.3 keV.

As is apparent from the characteristics shown in FIGS. 1(A)–1(C), it is understood that an emission distribution of back-scattered electrons is high in a direction orthogonal to the surface of the sample and conforms to the cosine rule when an incident angle to the surface of the sample is approximately 35° or more, but the incident angle dependence is prominent when the incident angle is approximately 30° or less. It can therefore be appreciated that the incident angle is preferably set at 35° or more. Also, when the incident angle is set in a range of 70° to 90°, an emission distribution of reflected electrons is substantially the same as that which is found when a primary electron beam is directed perpendicularly to the surface of the sample, so that such setting of the incident angle will not cause a reduction in the number of detected electrons with respect to the incident beam.

Figure 2:
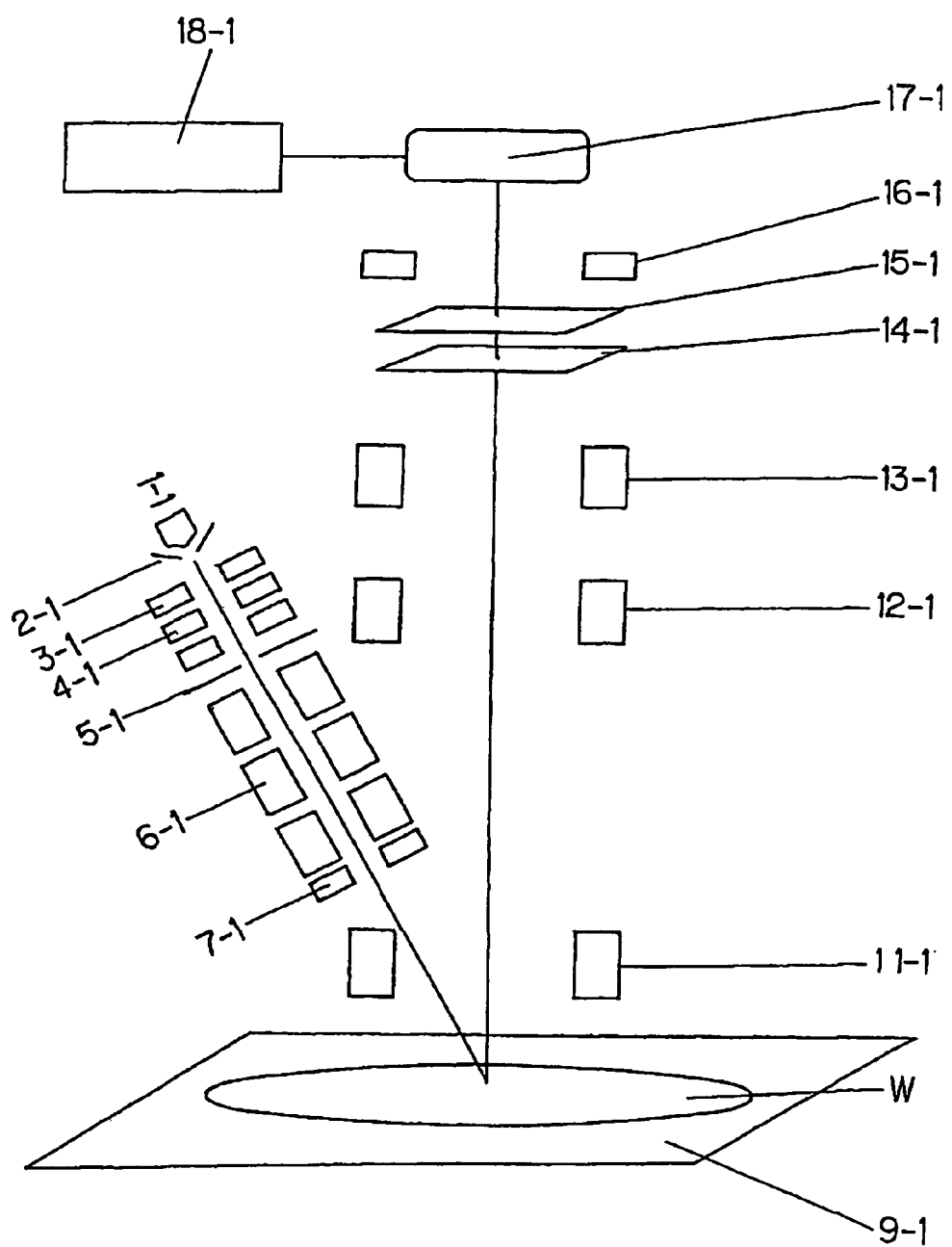
FIG. 2 is a schematic diagram generally illustrating a first embodiment of an electron beam apparatus according to the present invention.

FIG. 2 is a diagram for explaining a first embodiment of an electron beam apparatus according to the present invention which detects electrons having information on the surface of a sample, when it is irradiated with a primary electron beam, to evaluate the surface of the sample. In the first embodiment, the electron beam apparatus comprises a single lens column which contains an electron gun and a primary opto-electro system for directing only a single primary electron beam onto the surface of a sample in a direction inclined to the surface.

In the first embodiment, the electron gun comprises an electron source 101, a Wehnelt electrode 2-1, and an anode (acceleration electrode). As an electron beam is radiated from the electron gun, a primary electron beam is irradiated to a sample W placed on an X-Y-θ stage 9-1 through an electrostatic lens 4-1, an aperture 5-1, a quadruple electrode 6-1, a deflector 7-1, and an objective lens or electrostatic lens 11-1 which make up a primary opto-electro system. Consequently, secondary electrons or reflected electrons are emitted from the sample W.

The incident angle for the primary electron beam, which may be adjusted by controlling the deflector 8-1, should be selected to be approximately 35° or more, as has been previously described in connection with FIG. 1.

Electrons emitted from the sample W are guided in a direction normal to the sample W through the objective lens comprised of an electrostatic lens, and electrostatic lenses 12-1, 13-1, and are focused on a detector disposed on the vertical line. The electrostatic lenses 12-1, 13-1 make up a secondary opto-electro system, while the objective lens 11-1 is shared by the first opto-electro system and secondary opto-electro system. The detector is made up of a microchannel plate (MCP) 14-1, a fluorescent screen 15-1, a relay lens 16-1, and a TDI (or CCD) 17-1. Electrons enlarged by the electrostatic lenses 11-1-13-1 and projected onto the MCP 14-1 are multiplied by the MCP 14-1, and converted into an optical signal by the fluorescent screen 15-1. The resulting optical signal is guided by the relay lens 16-1 to the TDI 17-1 which detects the optical signal as an image.

In this event, since the primary electron beam is irradiated onto the sample while the X-Y-θ stage 9-1 is two-dimensionally moved in a continuous manner, the TDI 17-1 can acquire a signal representative of a two-dimensional image which includes an area under inspection of the sample W. The electric signal from the TDI 17-1 is supplied to a personal computer 18-1 for image processing, which can reproduce the two-dimensional image. For testing the sample W for defects, images of dies on the sample W may be compared with each other, or may be compared with another reference image to detect such defects.

Figure 3:
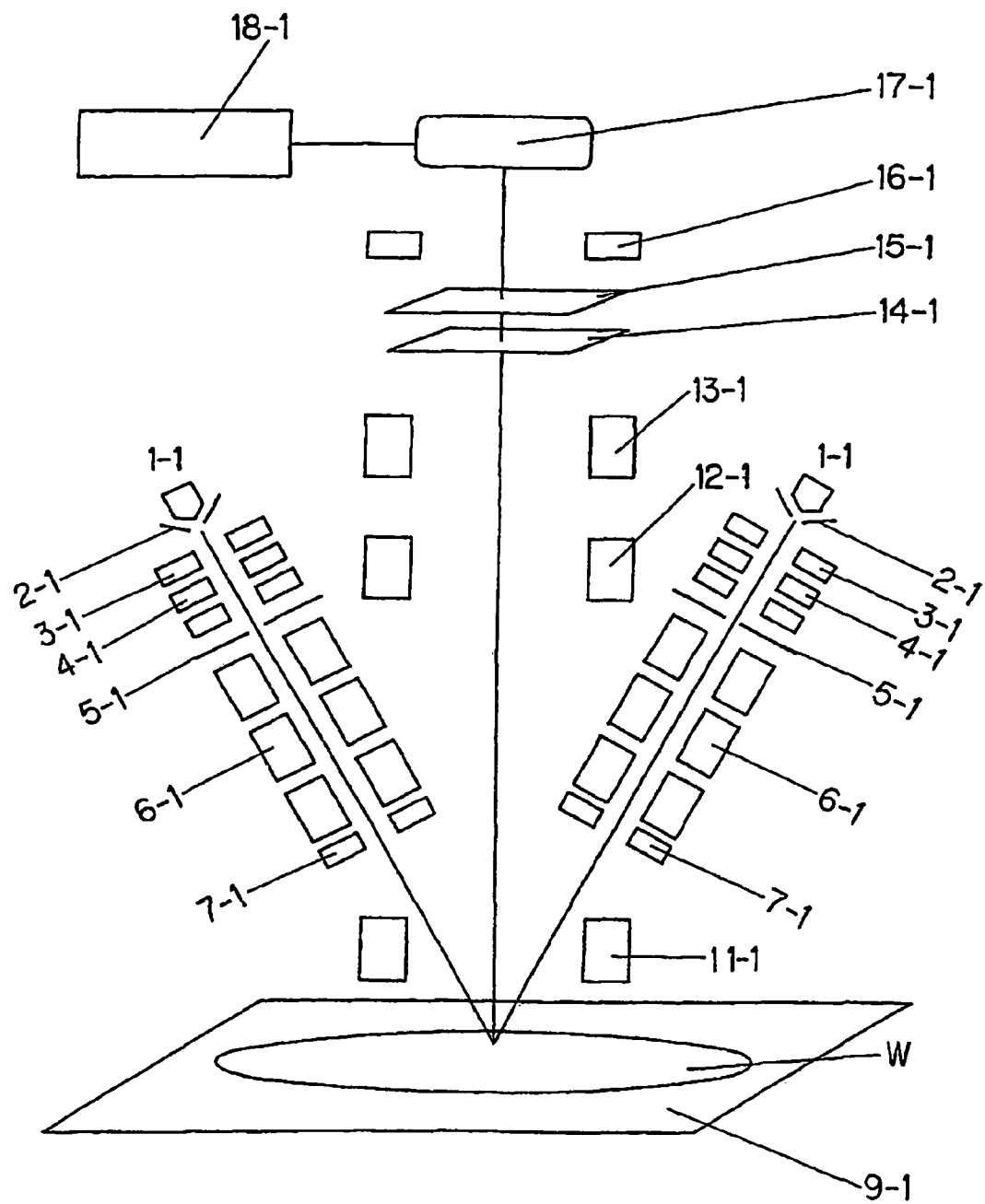
FIG. 3 is a schematic diagram generally illustrating a second embodiment of the electron beam apparatus according to the present invention.

FIG. 3 is a diagram for explaining a second embodiment of the electron beam apparatus according to the present invention. In the second embodiment, the electron beam apparatus is configured to irradiate a spot under observation on the sample W with two primary electron beams which are simultaneously emitted in inclined directions symmetric about the optical axis of the secondary opto-electro system. Specifically, in the second embodiment, the electron beam apparatus comprises two lens columns s, each of which is made up of an electron gun (1-1-3-1) and a primary opto-electro system (4-1-7-1, 11-1), and the optical axes of these lens columns are set symmetric about the optical axes of a secondary optical system (11-1-13-1). It should be understood that the electron beam apparatus may include three or more lens columns.

Likewise, in the second embodiment, the incident angle of the primary electron beams should be selected to be 35° or more, as has been previously described.

Figure 4:
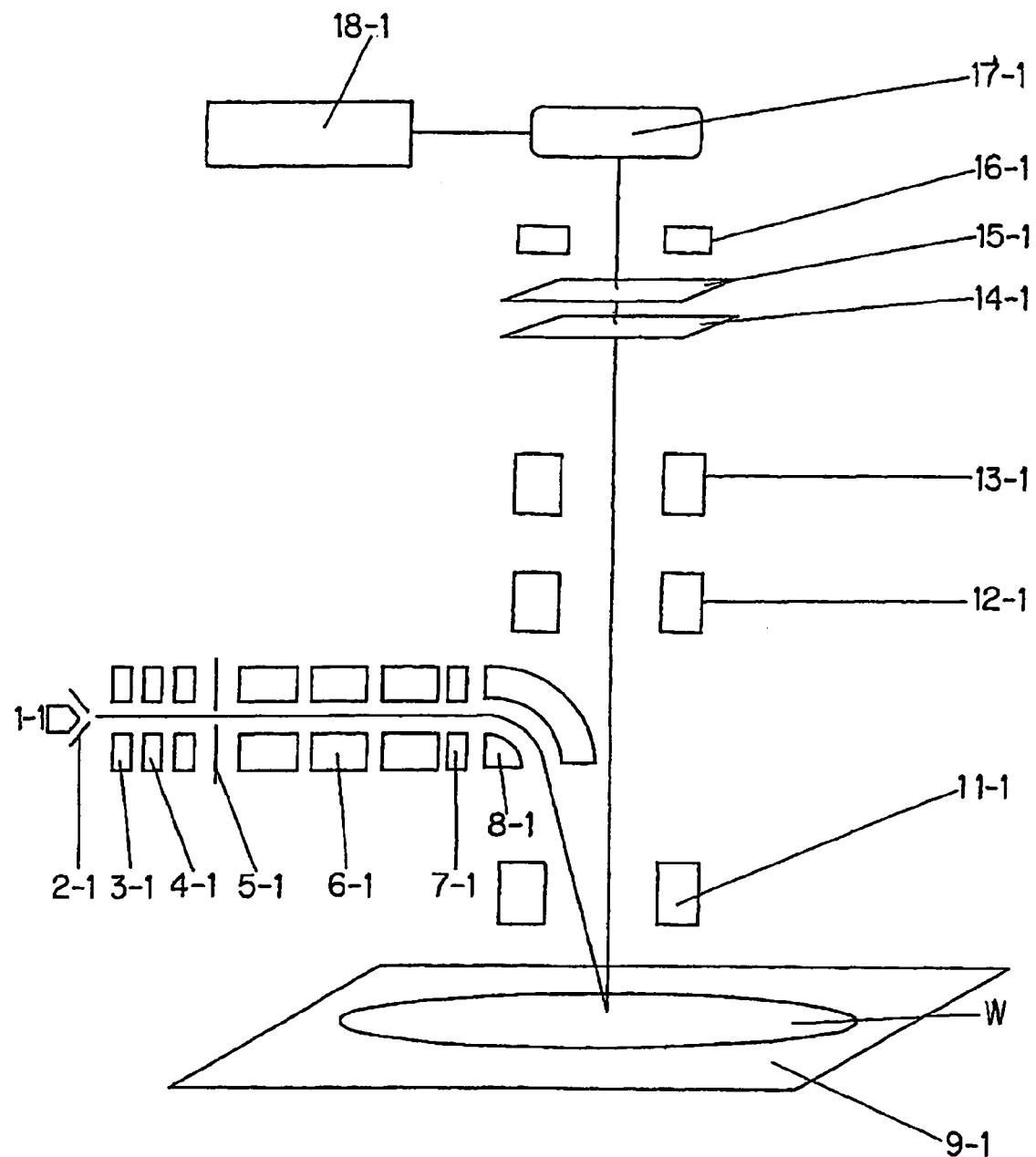
FIG. 4 is a schematic diagram generally illustrating a third embodiment of the electron beam apparatus according to the present invention.

FIG. 4 illustrates a third embodiment of the electron beam apparatus according to the present invention. In the third embodiment, the electron beam apparatus is configured to irradiate an electron beam onto a sample at a larger incident angle. In comparison with the first embodiment illustrated in FIG. 2, a sector or fan-shaped deflector 8-1 is added between the deflector 7-1 and the objective lens 11-1.

Now, description will be made of the configuration of the fan-shaped deflector 8-1.

Figure 5:
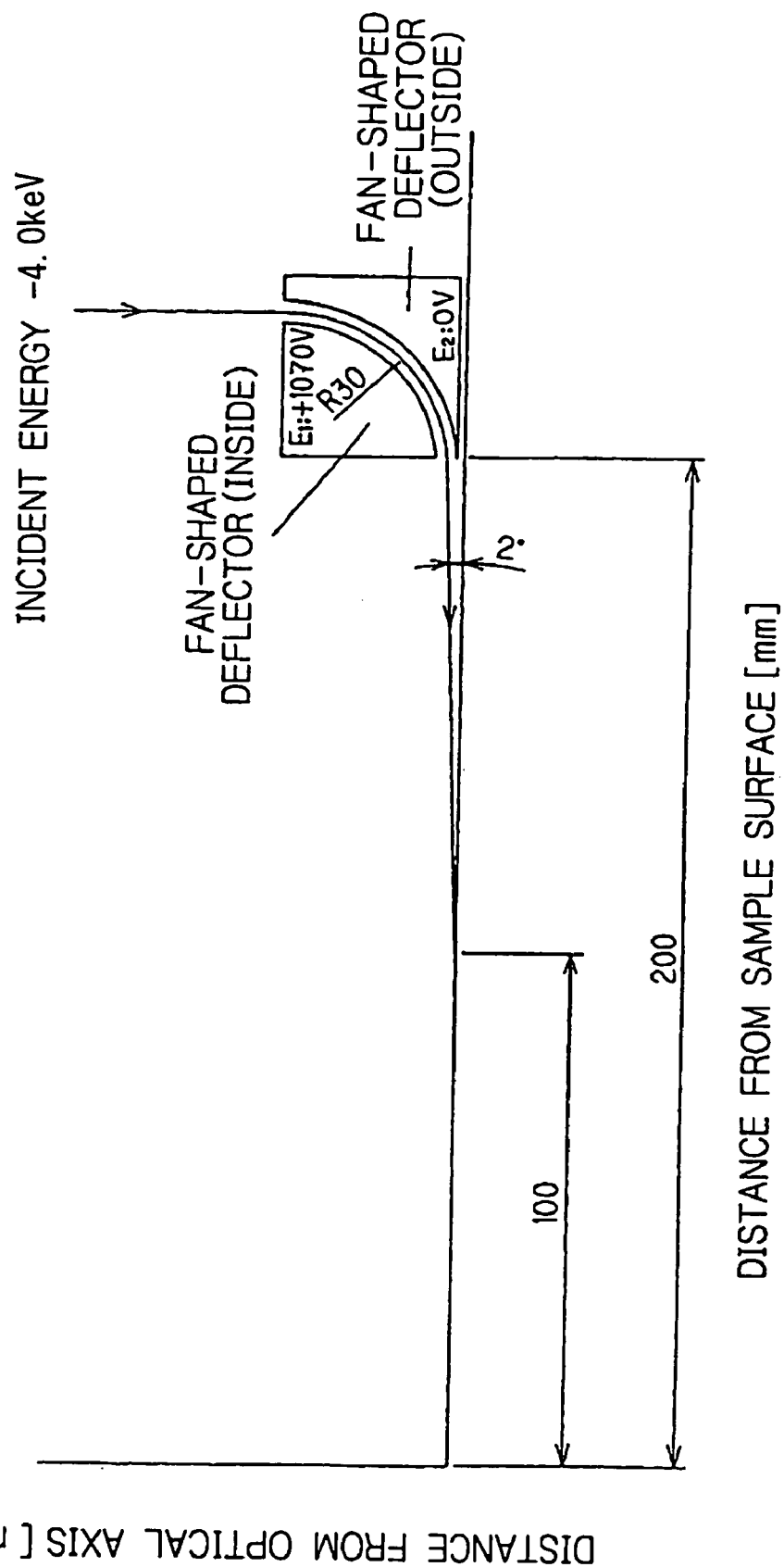
FIG. 5 is an explanatory diagram illustrating the configuration of a fan-shaped deflector used in the third embodiment illustrated in FIG. 4.

FIG. 5 is a diagram illustrating the configuration of the fan-shaped deflector 8-1 for deflecting a primary electron beam with an electric field or a magnetic field.

When an electric field is relied on for a deflecting function of the deflector 8-1, the following relationship is established in accordance with the equation of motion, where E represents the field strength, m the mass of electron, v the velocity, e a charge, and R the radius of a trajectory:

$$m \cdot v^2 / R = e \cdot E$$

In the foregoing relationship, assuming that the energy V of electron is 4.0 KeV, the velocity v of electron is $3.755 \times 10^7$ m/s, and the field strength E is calculated to be $3.0 \times 10^5$ V/m when the radius R of the trajectory is 30 mm.

With such a field strength, assuming that there is a spacing d equal to 4 mm between an inner electrode E1, which serves as a guide for the deflector, and an outer electrode E2, these electrodes may be set at potentials of +535V and −535V, respectively. Specifically, the voltage V between the two electrodes is calculated in the following manner:

$$V = E \cdot d = 2.67 \times 10^6 \times 4 \times 10^{-3} = 1{,}070 \quad \text{(V)}$$

Therefore, for generating 1,070V, these electrodes may be set at potentials of +535V and −535V, respectively. However, if one wishes to set the outer electrode E2 close to the optical axis at 0V (or ground potential), the inner electrode E1 may be applied with +1,070V.

On the other hand, when a magnetic field is relied on for the deflection of the deflector 8-1, the following relationship is established in accordance with the equation of motion:

$$m \cdot v^2 / R = e \cdot v \cdot B$$

where B is the field strength.

With a calculation under the same condition as the foregoing (radius R of trajectory =30 mm), the resulting field strength B is calculated to be 71G.

Figure 6:
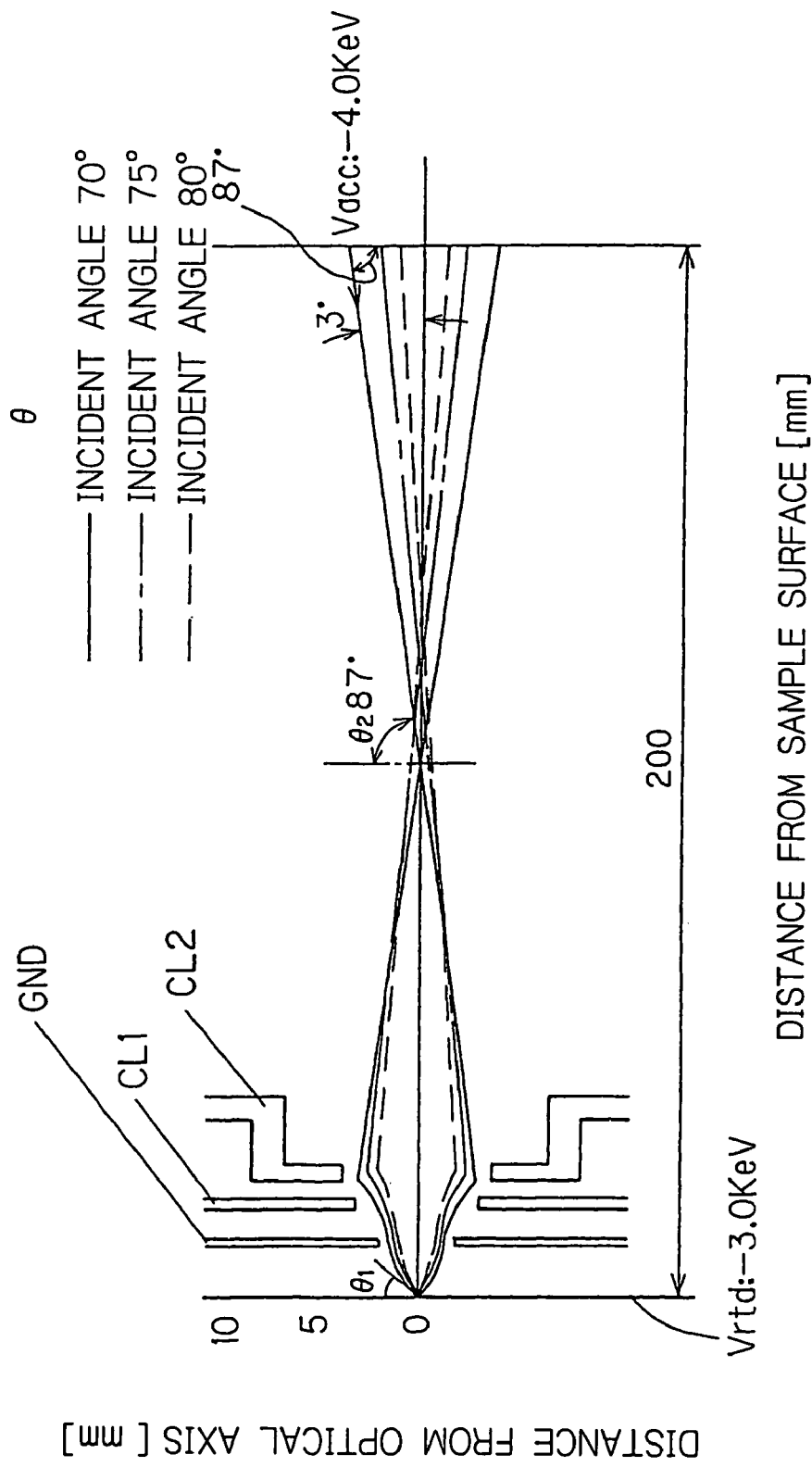
FIG. 6 is a diagram showing a trajectory of an incident primary electron beam during an observation of reflected electrons.

FIG. 6 shows trajectories of an incident primary electron beam, derived by a simulation, when the primary electron beam emitted with energy of V=4 KeV (detected reflected electrons also have energy of 4 KeV) is directed to a position on the surface of a sample (i.e., at height of 0 mm on the sample) at an incident angle θ1 of each of 70°, 75°, and 80°, in an exemplary detection of reflected electrons. Electron beams directed at an incident angle of 70° or less impinge on an inner wall of an electrode such as the electrostatic lenses CL1, CL2 and the like, and therefore cannot reach the position on the sample. As shown in FIG. 6, when θ1=70°, an incident angle θ2 is approximately 87° at a position Z=100 mm which is the midpoint of a trajectory from the deflector 8-1 to the surface of the sample; a distance of 200 mm. As is apparent from the foregoing, electron beams which can reach the surface of the sample are only those which enter at an incident angle of approximately 87° or more with respect to the direction of the sample at a position distanced by 100 mm from the position of the sample toward the detector.

Bearing the foregoing in mind, in the present invention, the fan-shaped deflector 8-1 is positioned such that beams at the exit of the fan-shaped deflector 8-1 form an angle of approximately 87° with the surface of the sample, and the straight traveling beam intersects the optical axis at a position distanced by 100 mm from the sample. Also, the primary opto-electro system includes an electrostatic lens 6-1 comprised of quadruple electrodes (QL) which causes the primary electron beams to crossover at a position distanced by 100 mm from the surface of the sample.

Figure 7:
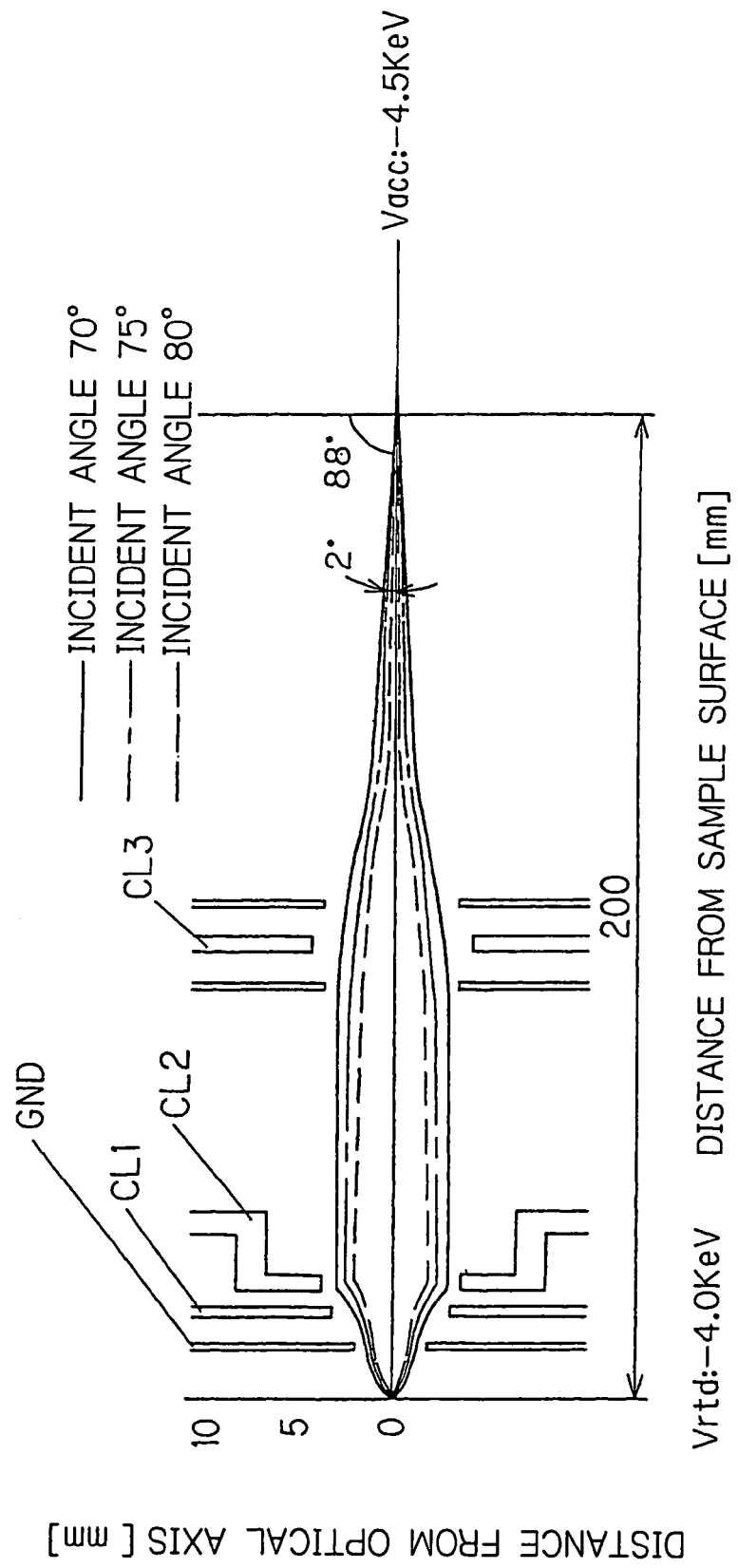
FIG. 7 is a diagram showing a trajectory of an incident primary electron beam during an observation of secondary electrons.

FIG. 7 shows trajectories of incident primary electron beams, derived by a simulation, when the primary electron beams emitted with energy of V=4.5 KeV are directed to the surface of a sample at an incident angle of each of 70°, 75°, and 80°, in an exemplary detection of secondary electrons. For detecting secondary electrons, the fan-shaped deflector 8-1 is adjusted in position such that the primary electron beams can be directed to the surface of the sample at an angle of approximately 88° at a position distanced by 200 mm from the surface of the sample.

It should be noted that while FIGS. 6 and 7 show the trajectories produced through simulations as mentioned above, the trajectories are actually deflected by voltages applied to the cylindrical electrodes CL1, CL2, CL3, so that the deflector 8-1 should be adjusted in position before it is installed in consideration of such unintended deflections.

In the third embodiment, the fan-shaped deflector 8-1, in the configuration illustrated in FIG. 5, may be used, and the incident angle (θ1 or θ2) of the primary electron beam may be adjusted at the position at which the primary electron beam is incident (at 100 mm or 200 mm) depending on whether emitted electrons to be detected are reflected electrons or secondary electrons.

While the lens column (up to the deflector 7 of the primary opto-electro system) is installed such that the optical axis thereof is horizontal, i.e., in parallel with the surface of the sample, the lens column may have a certain inclination instead of being horizontal. Nevertheless, the horizontal installation is optimal in consideration of ease of the manufacturing, installation and machining accuracy of the fan-shaped deflector 8-1.

Figure 8:
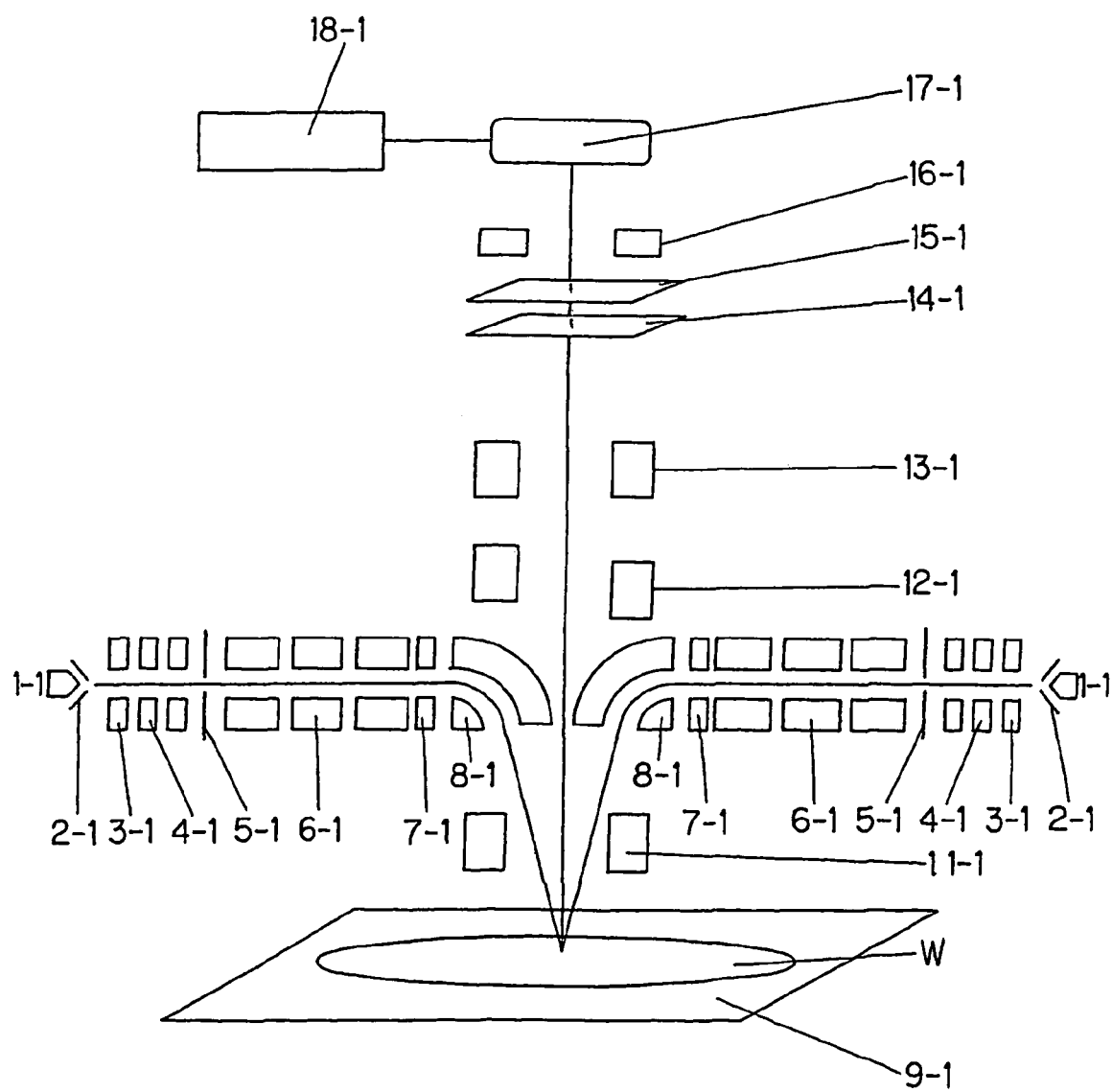
FIG. 8 is a schematic diagram illustrating a fourth embodiment of the electron beam apparatus according to the present invention.

FIG. 8 is a diagram for explaining a fourth embodiment of the electron beam apparatus according to the present invention. In the fourth embodiment, the electron beam apparatus comprises a pair of lens columns s, each of which comprises a fan-shaped or sector-shaped deflector 8-1 that is added to the third embodiment illustrated in FIG. 5, and is configured to irradiate a sample W with two primary electron beams in axial symmetry about the optical axis of the secondary opto-electro system. Likewise, in this embodiment, the electron beam apparatus may comprise three or more lens columns.

Figure 9:
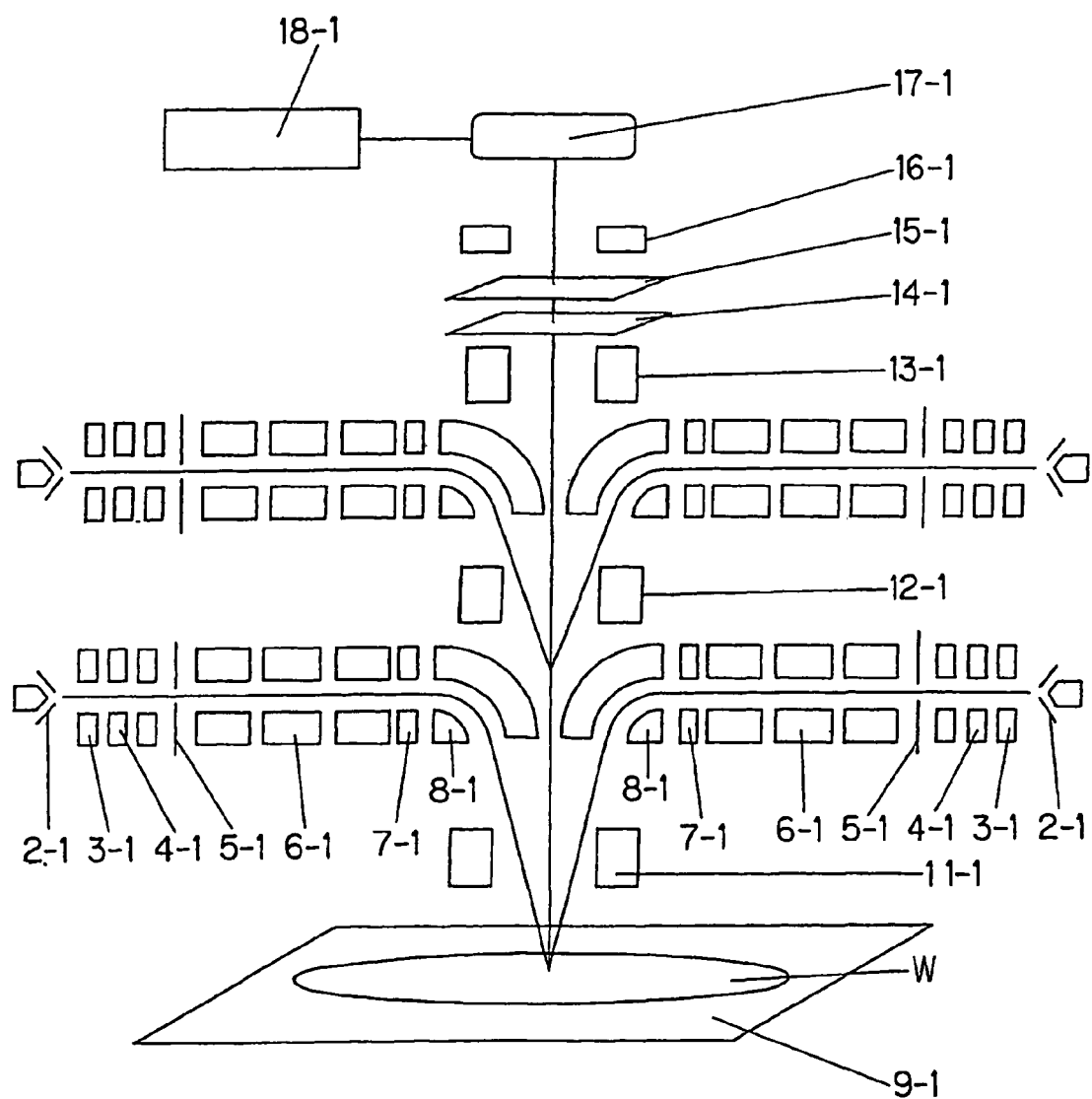
FIG. 9 is a schematic diagram illustrating a fifth embodiment of the electron beam apparatus according to the present invention.

FIG. 9 is a diagram for explaining a fifth embodiment of the electron beam apparatus according to the present invention. In the fifth embodiment, the electron beam apparatus further comprises a pair of lens columns in a second stage in addition to the pair of lens columns disposed in the fourth embodiment illustrated in FIG. 8. The lens columns may be arranged in three or more stages, and/or three or more lens columns may be included in each stage.

Next, the operation of a specific example will be described when a sample W is actually irradiated with a total of eight primary electron beams from four lens columns in each stage in the fifth embodiment illustrated in FIG. 9.

The sample W is a silicon wafer, the diameter of which may range from 8 to 12 inches, and is formed with circuit patterns during manufacturing of LSIs. As an electron beam is radiated from an electron gun made up of an electron source 1-1, a Wehnelt electrode 2-1, and an anode (acceleration electrode), the electron beam is irradiated onto the sample W at an angle of 3° to the optical axis of the secondary opto-electro system through an electrostatic lens 4-1, an aperture 5-1, a quadruple-electrode lens 6-1, a deflector 7-1, a fan-shaped deflector 8-1, and an objective lens 11-1, which make up the primary opto-electro system. Then, the quadruple-electrode lens 6-1 is adjusted such that the crossover is formed at a position distanced by 100 mm from the surface of the sample W in the normal direction, and is also adjusted such that the beam has a spot diameter f of approximately 200 μm on the sample W. When the quadruple-electrode lenses 6-1 are used in three or more stages, an oval spot may be irradiated to the sample as a pseudostigmatic condition.

When a conventional ExB deflector is used to irradiate a single beam to a spot having a diameter of 200 μm, a current of merely 1.6 μA is generated, whereas in the foregoing example of the present invention, a current of 12.8 μA (1.6 μA×8) can be generated by simultaneously irradiating eight primary electron beams to a spot having a diameter of 200 μm.

The detection of reflected electrons from the sample W and associated image processing are performed in a manner described in connection with the first embodiment illustrated in FIG. 2.

In the following, the number of electrons detected by the foregoing specific example of the electron beam apparatus according to the present invention will be compared with the number of electrons detected by a conventional single-beam electron beam apparatus using an ExB deflector.

In the prior art example, when the magnification of the secondary optical system is set to 320, and the TDI pixel size is set to 16 μm square (16×16 μm²), a pixel size on the sample is equivalent to 0.05 μm square. When the primary opto-electro system has a current density of 1.6 μA and the secondary opto-electro system has a transmittance of 4.2%, 390 secondary electrons are detected within one pixel of the TDI, so that a test can be conducted at a TDI line rate of 3.3 μsec and a stage speed of 15 mm/sec. However, as to reflected electrons, the number of detected electrons is one one-hundredth part of the number of detected secondary electrons, and therefore, the number of reflected electrons detected within one pixel of the TDI is approximately 3.9.

On the other hand, in the embodiment of the present invention described above, since eight primary electron beams are simultaneously irradiated, 31.2 reflected electrons (=3.9×8) can be detected. It is therefore possible to ensure a number of electrons required to form images in 512 levels of gradation. When a CCD is used instead of the TDI, the present invention can accomplish an S/N ratio eight times higher than the prior art example, as is the case with the TDI-based test speed ratio.

For detecting secondary electrons instead of reflected electrons, it is possible to use only one of the eight primary electron beams in order to ensure a throughput equivalent to the throughput associated with the detection of reflected electrons in the embodiment of the present invention described above. When a single electron beam was used and the quadruple-electrode lens 6-1 was adjusted to form a crossover at a position distanced by 200 mm from the surface of the sample, the stage speed reached 15 mm/sec when the TDI was used. When the throughput should be further improved, primary electron beams from some of the remaining lens columns may be used as appropriate.

For detecting secondary electrons, the lens columns in the upper stage are preferably used.

When all the primary electron beams are not used for the detection, the remaining primary electron beams may be shifted to the front of an observed spot to pre-charge the wafer, thereby alleviating the influence due to charge-up.

Next, description will be made of a semiconductor device manufacturing method according to the present invention, with reference to FIGS. 10 and 11. The semiconductor device manufacturing method according to the present invention is executed using the electron beam apparatus as described above.

Figure 10:
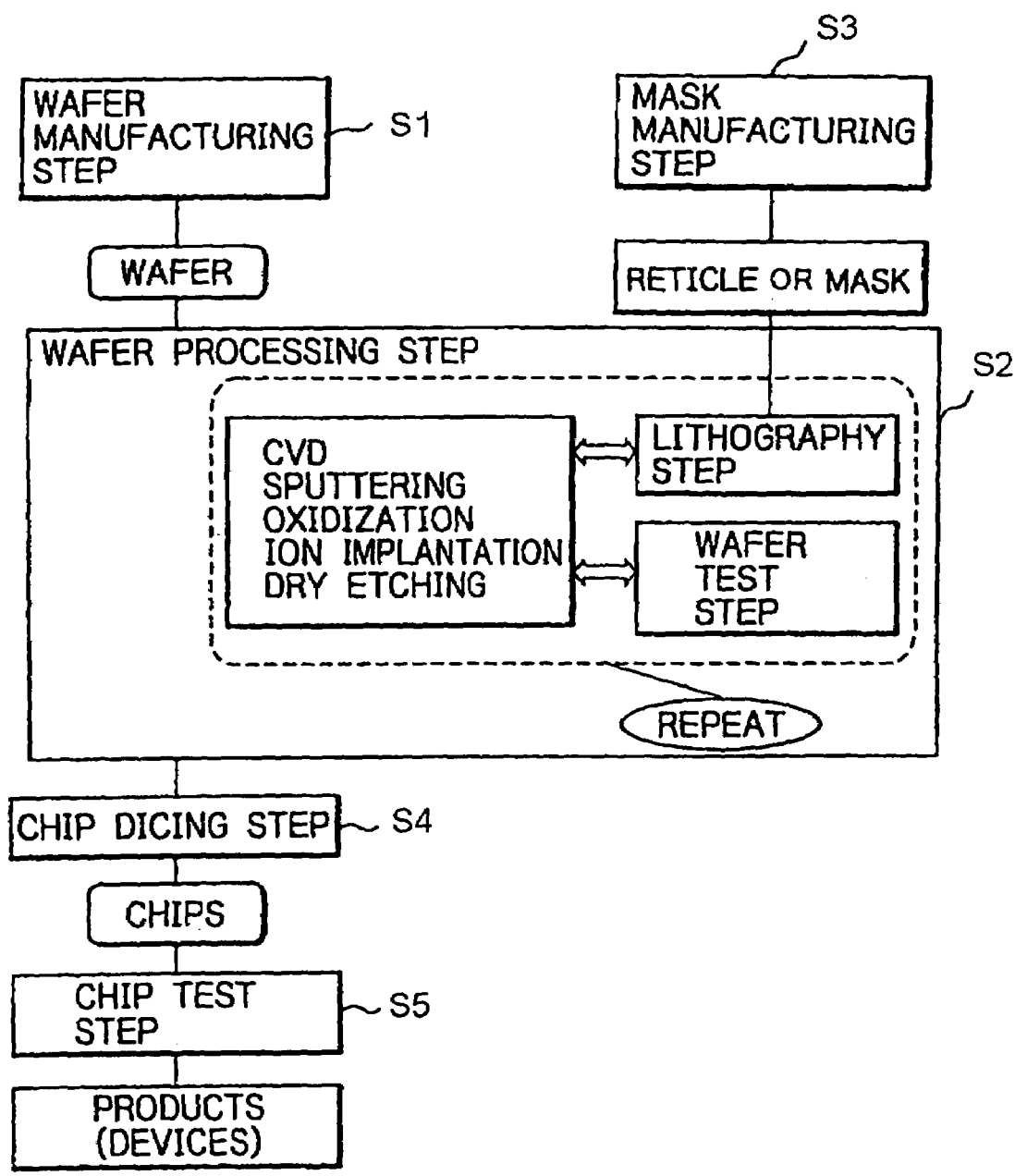
FIG. 10 is a flow chart representing an exemplary method of manufacturing semiconductor devices according to the present invention.

As illustrated in FIG. 10, the semiconductor device manufacturing method may be generally divided into a wafer manufacturing process Si for manufacturing wafers; a wafer processing process S2 for processing wafers as required; a mask manufacturing process S3 for manufacturing masks required for exposure; a chip assembling process S4 for singulating chips formed on a wafer to make the respective chips; and a chip testing process S5 for testing completed chips. These processes may include several sub-processes.

Among the foregoing processes, the wafer processing process S2 exerts a decisive influence on the manufacturing of semiconductor devices. In this process, a designed circuit pattern is formed on a wafer to create multiple chips which will operate as a memory and MPU.

Thus, it is critical to evaluate how a wafer is processed in the wafer processing process S2 which affects the manufacturing of semiconductor devices. The process S2 includes the following steps:

1. a thin film formation step for forming dielectric thin films which serve as insulating layers, wires, metal thin films which form electrodes, and the like (using CVD and sputtering);

2. an oxidization step for oxidizing the thin film layers and wafer;

3. a lithography step for forming a resist pattern using a mask (or reticle) for selectively processing thin film layers, wafer substrate, and the like;

4. an etching step for processing the thin film layers and substrate in accordance with a resist pattern (for example, using a dry etching technique);

5. an ion/impurity injection and diffusion step;

6. a resist stripping step; and 7. a wafer test step for testing or inspecting processed wafers.

It should be noted that the foregoing steps, which make up the wafer processing process S2, are repeated a number of times equal to the number of required layers to form the processed wafer before it is diced into individual chips in the chip assembling process S4.

Figure 11:
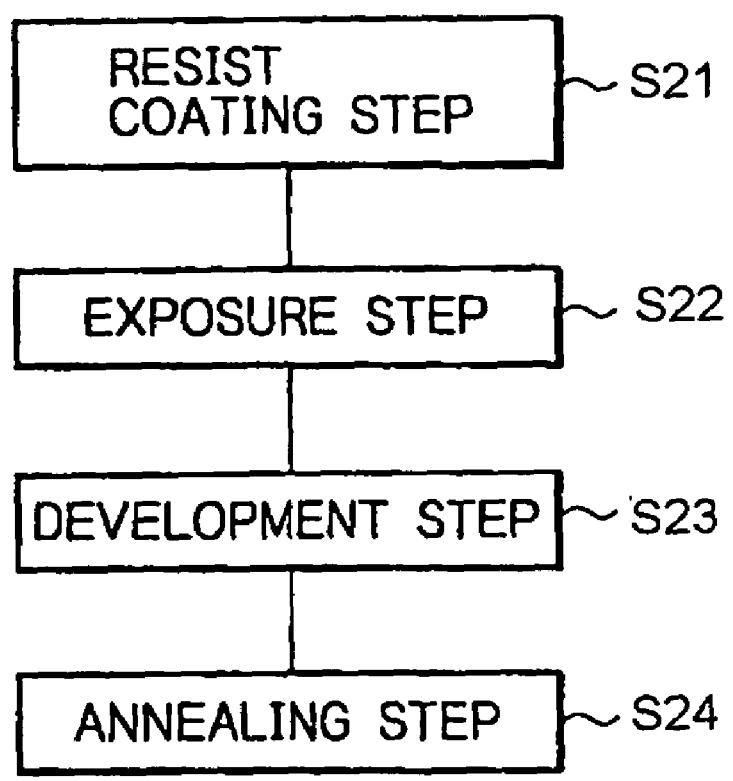
FIG. 11 is a flow chart representing a lithography step which forms the heart of a wafer processing process shown in FIG. 10.

FIG. 11 is a flow chart illustrating a lithography step which is a sub-process of the wafer processing process S2 in FIG. 10. As illustrated in FIG. 11, the lithography step includes a resist coating step S21, an exposure step S22, a development step S23, and an annealing step S24.

In the resist coating step S21, a resist is coated on a wafer, which has been formed with circuit patterns thereon, using CVD or sputtering, and the coated resist is exposed in the exposure step S22. Then, the exposed resist is developed to create a resist pattern in the development step S23. The developed resist pattern is annealed in the annealing step S24 for stabilization. These steps S21–S24 are repeatedly executed a number of times equal to the number of required layers.

In the semiconductor device manufacturing method of the present invention, the electron beam apparatus described in connection with FIGS. 1 to 9 can be used not only in an intermediate process during the processing (wafer test process) but also in the chip test process S5 for testing or inspecting completed chips to generate images of semiconductor devices on a wafer, even if they have miniature patterns, with reduced distortions, blur and the like, thus detecting defects in the wafer without fail.

Next, description will be made of the general configuration of a semiconductor wafer inspection system which can incorporate and utilize the electron beam apparatus according to the present invention.

Figure 12:
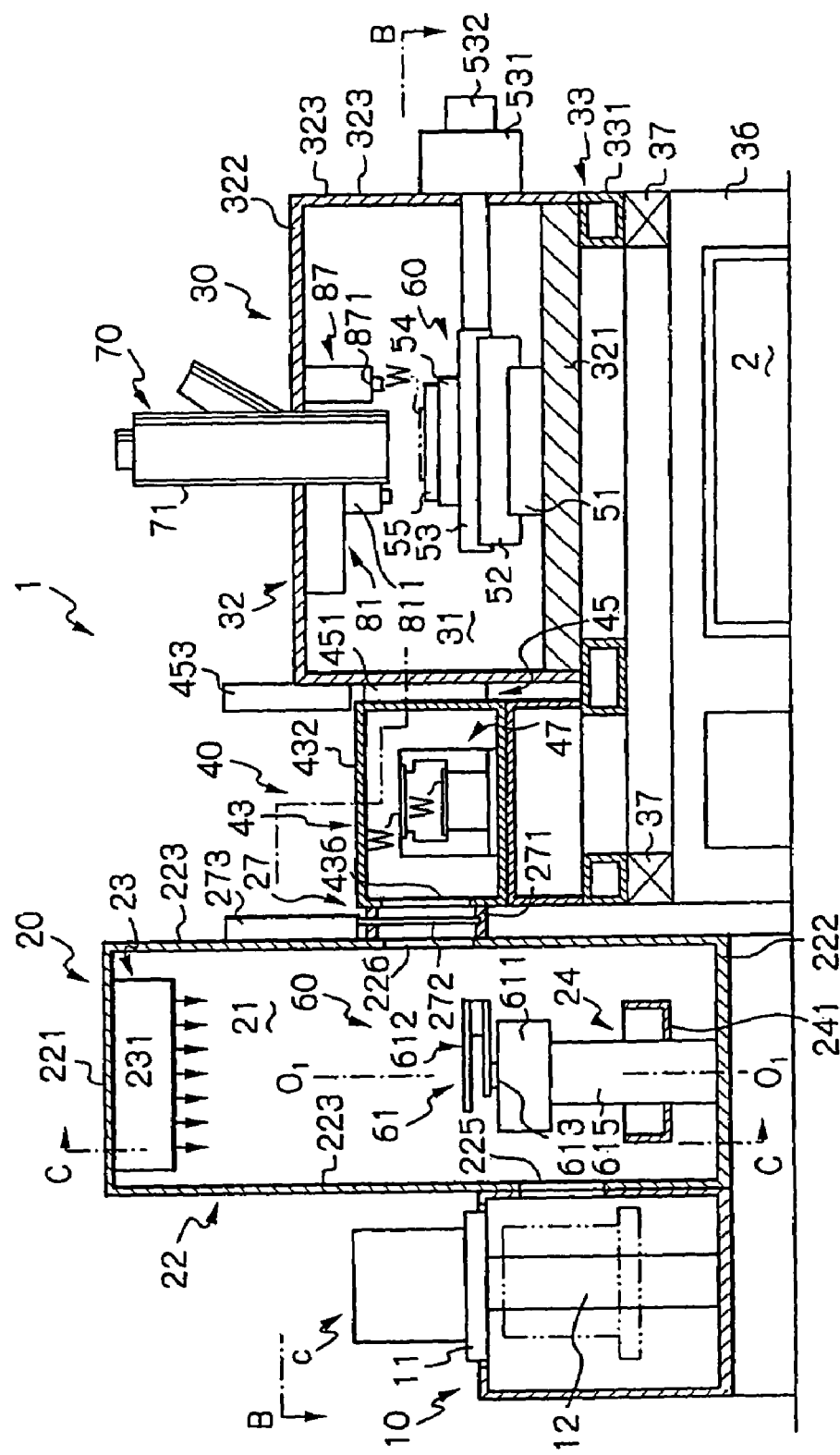
FIG. 12 is an elevation illustrating main components of a semiconductor wafer inspection system to which the electron beam apparatus according to the present invention can be applied.
Figure 13:
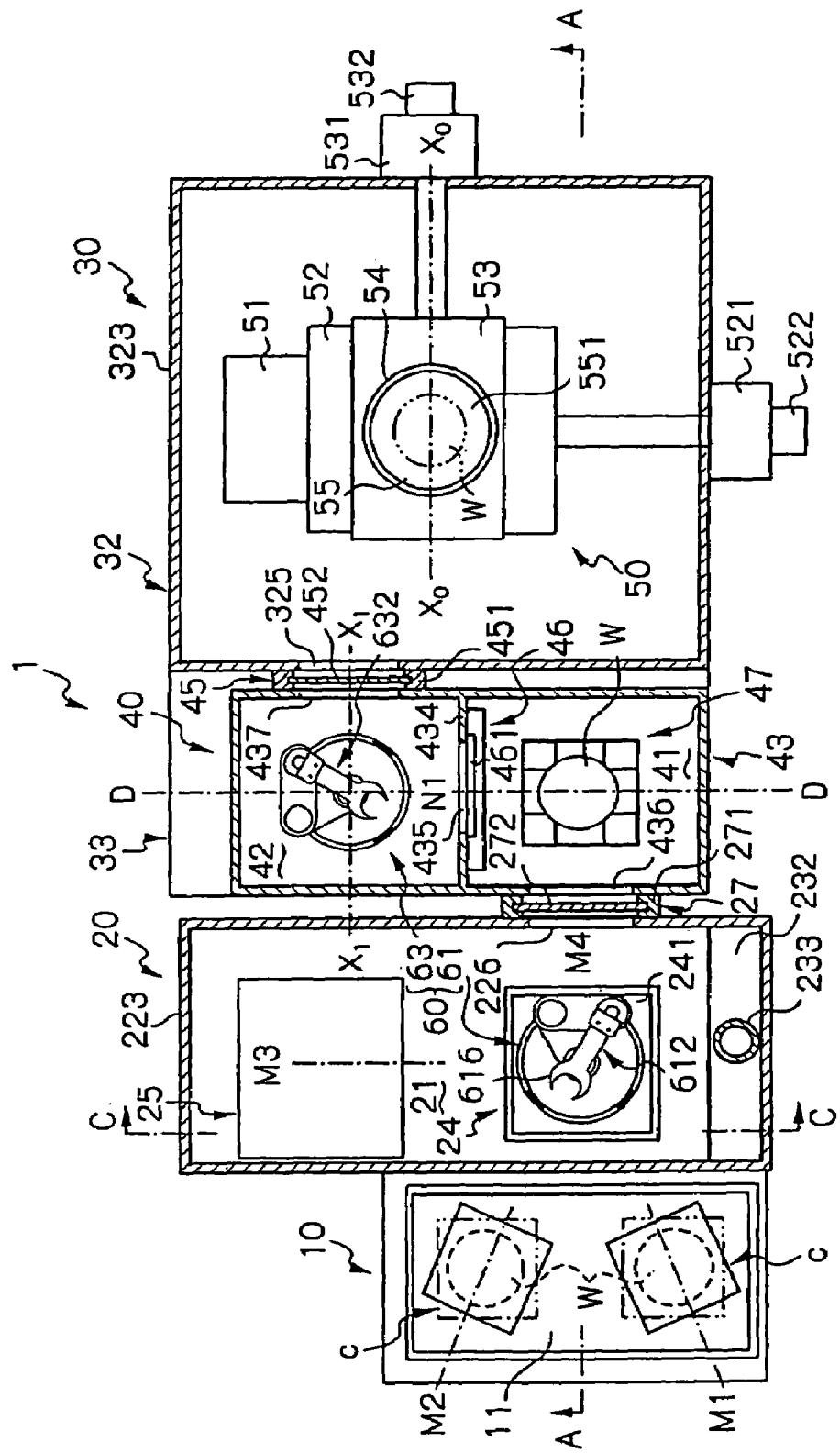
FIG. 13 is a top plan view of the main components of the inspection system illustrated in FIG. 12, taken along a line B—B in FIG. 12.

FIGS. 12 and 13 are an elevation and a plan view illustrating main components of the inspection system 1, respectively. The inspection system 1 comprises a cassette holder 10 for holding a cassette which contains a plurality of wafers; a mini-environment device 20; a main housing 30; a loader housing 40 disposed between the mini-environment device 20 and the main housing 30 for defining two loading chambers; a stage device 50 disposed within the main housing 30 for carrying a wafer W for movements; a loader 60 for loading a wafer from the cassette holder 10 onto the stage device 50 disposed within the main housing 30; and an opto-electro system 70 mounted in the main housing 30. These components are arranged in a positional relationship as illustrated in FIGS. 12 and 13. The electron beam apparatus of the present invention can be employed as the opto-electro system 70.

Figure 19:
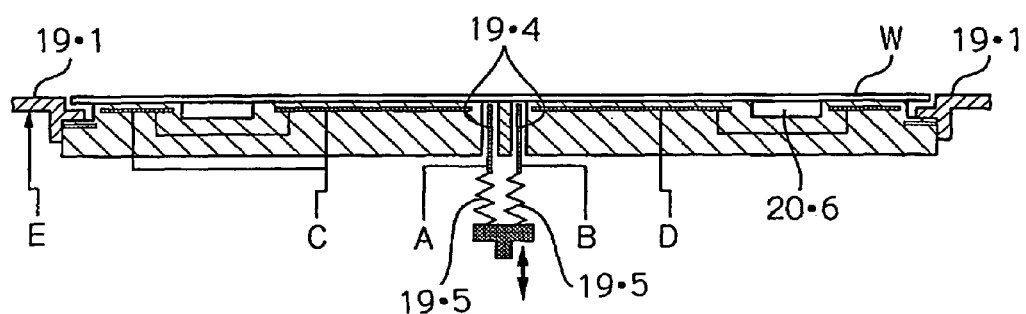
FIGS. 19(A) and 19(B) are diagrams for explaining a further exemplary electrostatic chuck used in the electron beam apparatus according to the present invention.
Figure 19:
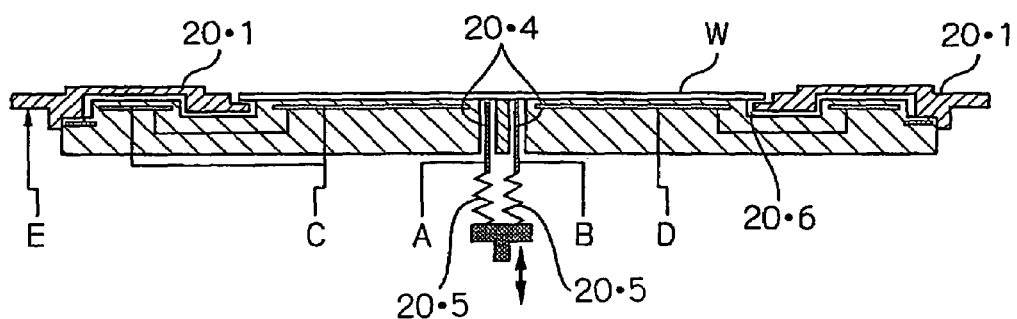

The inspection system 1 also comprises a pre-charge unit 81 disposed in the main housing 30 in vacuum; a potential applying mechanism for applying a potential to a wafer; an electron beam calibration mechanism; and an optical microscope 871 which forms part of an alignment control unit 87 (shown in FIG. 19) for aligning a wafer on the stage device 50. The inspection system 1 further comprises a control device 2 for controlling the operation of these components.

In the following, detailed description will be made of the configuration of the respective main components (sub-systems) of the inspection system 1.

Cassette Holder 10

The cassette holder 10 is configured to hold a plurality (two in this embodiment) of cassettes c (for example, closed cassettes such as SMIF, FOUP made by Assist Co.), each of which contains a plurality (for example, 25) of wafers arranged one above another in parallel. When a cassette is transferred and automatically loaded into the cassette holder 10 by a robot or the like, the cassette holder 10 having a suitable structure can be selected for installation. Alternatively, when a cassette is manually loaded into the cassette holder 10, the cassette holder 10 having an open cassette structure, suitable for the manual loading, can be selected for installation. In this embodiment, the cassette holder 10 is a type which allows the cassettes c to be automatically loaded, and comprises, for example, an up/down table 11, and an elevating mechanism 12 for moving up and down the up/down table 11. The cassette c can be automatically loaded onto the up/down table in a state indicated by a chain line in FIG. 13, and after the loading, is automatically rotated to a state indicated by a solid line in FIG. 13 to be oriented to the axis of rotation of a first transfer unit within the mini-environment device 20. The up/down table 11 in turn is moved down into a state indicated by a chain line in FIG. 12.

Figure 14:
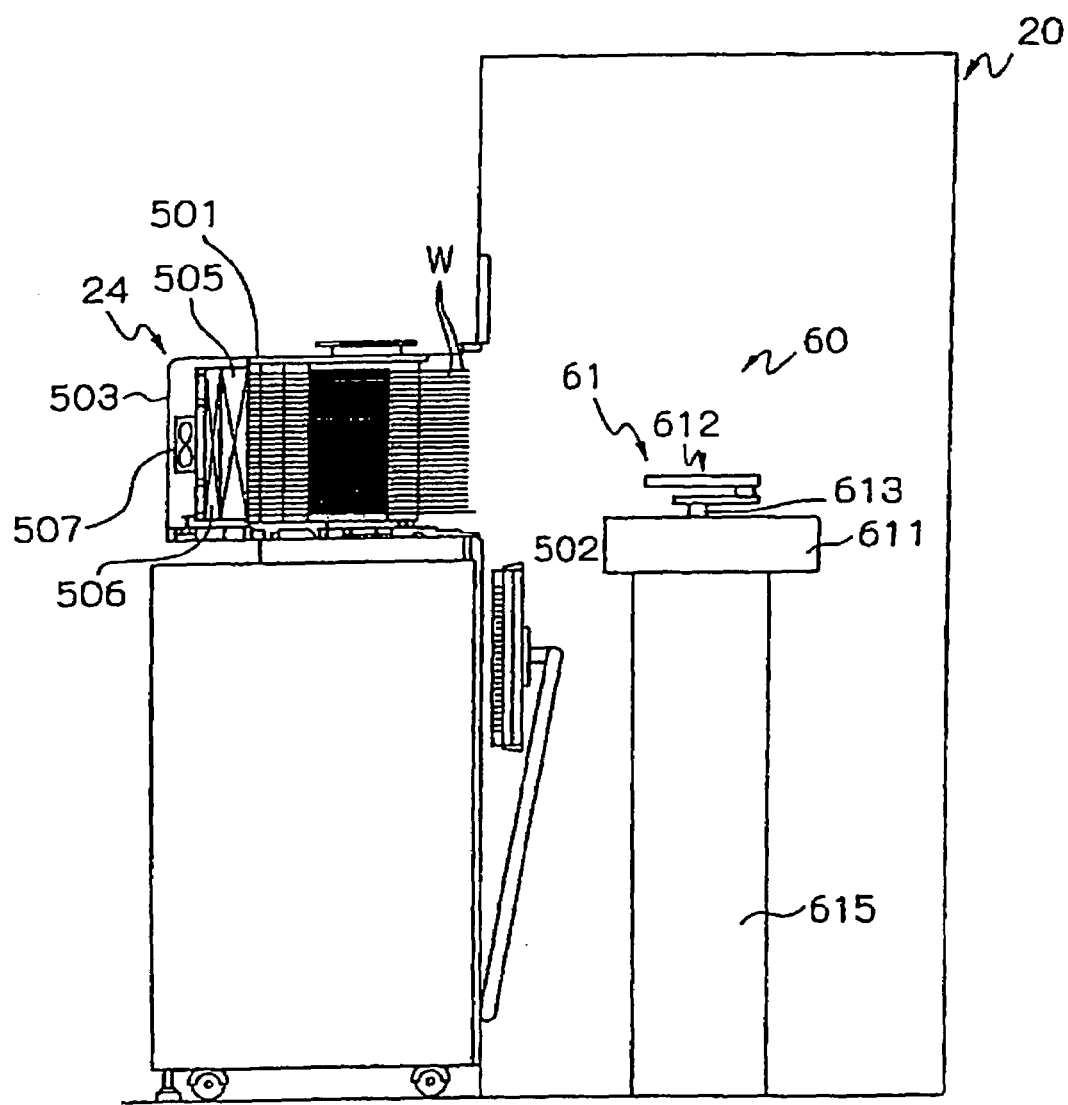
FIG. 14 is a diagram showing the relationship between a wafer carrier box and a loader in the inspection system illustrated in FIG. 12.

In another embodiment, as illustrated in FIG. 14, a plurality of 300 mm wafers W are placed in groove-shaped pockets (not shown) fixed inside a box body 501, transferred, and stored. A substrate carrier box 24 is coupled to the prism-shaped box body 501 and to an automatic gating device associated with a substrate transfer access door 502, and comprises the substrate transfer access door 502 for mechanically opening and closing an opening on a side surface of the box body 501; a lid 503 positioned opposite to the opening for covering the opening for mounting and removing filters and a fan motor; and a groove-shaped pocket 507 for holding wafers W. In this embodiment, wafers are transferred into and out of the box body 501 by a robot-type transfer unit 61 of the loader 60.

Wafers may be stored in the cassette c after the process for processing the wafers during the semiconductor manufacturing processes or during the process. Specifically, wafers which have undergone deposition, CMP, ion implantation and the like, wafers formed with wiring patterns on the surface thereof, wafers which have not been formed with wiring patterns may be stored in the cassette c for inspecting. Wafers stored in the cassette c are arranged one above another with a spacing therebetween and in parallel with one another, such that a first transfer unit, to be described later, can be moved up and down for holding a wafer at an arbitrary location within the cassette c with an arm thereof.

Mini-Environment Device 20

Figure 15:
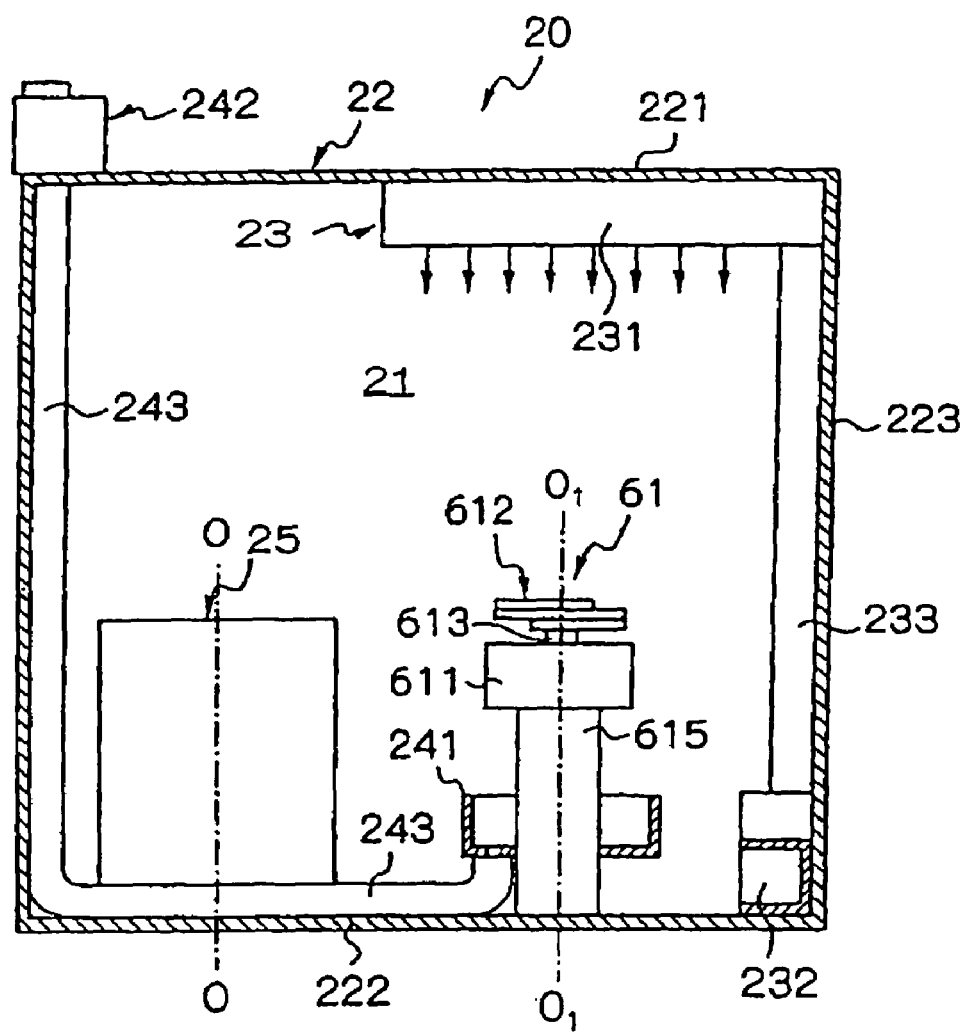
FIG. 15 is a cross-sectional view illustrating a mini-environment apparatus for use with the inspection system illustrated in FIG. 12, taken along a line C—C in FIG. 12.

FIG. 15 is an elevation of the mini-environment device 20, taken from a direction different from that in FIG. 12. As illustrated in FIG. 15 and the aforementioned FIGS. 12 and 13, the mini-environment device 20 comprises a housing 22 which defines a mini-environment space 21, the atmosphere of which is controlled; a gas circulator 23 for circulating a gas such as cleaning air within the mini-environment space 21 for controlling the atmosphere; a discharger 240 for recovering part of air supplied into the mini-environment space 21 for emission; and a pre-aligner 25 disposed within the mini-environment space 21 for roughly aligning a wafer which is a sample.

The housing 22 has a top wall 221, a bottom wall 222, and a peripheral wall 223 which surrounds the four sides of the housing 22, and is structured to block the mini-environment space 21 from the outside. For controlling the atmosphere within the mini-environment space 21, the gas circulator 23 comprises a gas supply unit 231 mounted on the top wall 221 to face downward for cleaning a gas (air in this embodiment) and supplying the cleaned air directly therebelow in laminar flow through one or more air blow ports (not shown); a recovery duct 232 mounted on the bottom wall 222 for recovering air which has flown down to the bottom from the gas supply unit 231; and a conduit 233 for connecting the recovery duct 232 to the air supply unit 231 for returning recovered air to the gas supply unit 231, as illustrated in FIG. 15.

The cleaned air, which goes down in laminar flow, is supplied such that it mainly flows through a carrying surface of a first transfer unit, to be described later, disposed within the mini-environment space 21, thereby preventing dust, possibly produced by the transfer unit, from sticking to wafers. A portion of the peripheral wall 223 of the housing 22 adjacent to the cassette holder 10 is formed with an access port 225.

The discharger 240 comprises a suction duct 241 disposed below a transfer unit, to be described later, at a position lower than the wafer carrying surface of the transfer unit; a blower 242 disposed outside the housing 22; and a conduit 243 for connecting the suction duct 241 to the blower 242. This discharger 240 aspires a gas flowing down around the transfer unit and including dust possibly produced by the transfer unit through the suction duct 241 for discharging the gas out of the housing 22 through the conduits 243, 244 and blower 242.

The pre-aligner 25 disposed within the mini-environment space 21 optically or mechanically detects an orientation flat (which refers to a flat portion formed near the outer periphery of a circular wafer) formed on a wafer, or one or more V-shaped notches formed on the outer periphery of a wafer, and preliminarily determines the position of the wafer in a rotating direction about the axial line $O_1$–$O_1$ of the wafer with an accuracy of approximately ±1 degree based on the detected orientation flat or V-shaped notches. The pre-aligner 25 forms part of a mechanism for determining the coordinates of the wafer, and is-responsible for alignment of wafers.

Main Housing 30

As illustrated in FIGS. 12 and 13, the main housing 30, which defines a working chamber 31, comprises a housing body 32 which is supported by a housing supporting device 33 carried on a vibration blocking device, i.e., a vibration isolator 37 disposed on a base frame 36. The housing supporting device 22 comprises a frame structure 221 assembled into a rectangular shape. The housing body 32, which is securely placed on the frame structure 331, comprises a bottom wall 321 carried on the frame structure 331; a top wall 322; and a peripheral wall 323 connected to the bottom wall 321 and top wall 322 to surround the four sides of the housing body 32 to isolate the working chamber 31 from the outside. In this embodiment, the housing body 32 and housing supporting device 33 are assembled in rigid structure, and the vibration isolator 37 prevents vibrations from a floor on which the base frame 36 is installed from transmitting to the rigid structure. A portion of the peripheral wall 343 of the housing 32 adjacent to the loader housing 40 is formed with an access port 325 for carrying a wafer into and removing a wafer from the loader housing 40.

The working chamber 31 is held in vacuum atmosphere by a general purpose evacuator (not shown). Below the base frame 36, a control device 2 is disposed for controlling the operation of the entire inspection system 1.

In the inspection system 1, a variety of housings including the main housing 30 are evacuated, wherein an evacuation system used for it is composed of vacuum pumps, vacuum valves, vacuum gages, vacuum pipes, and the like for evacuating the opto-electro systems, detector, wafer chamber, load lock chamber and the like in accordance with a predetermined sequence. In the respective components, the vacuum valve is controlled to achieve a required degree of vacuum. Then, the degree of vacuum is monitored at all times, such that in the event of a failure, an urgent control is conducted by an interlock function to disconnect between chambers, or between chambers and emission system with isolation valves or the like, thereby ensuring a required degree of vacuum in each of the components. Vacuum pumps suitable for use with the inspection system 1 may be a turbo molecular pump for main emission, and a Roots-type dry pump for rough pumping. A site under inspection (electron beam irradiated site) may be at pressure in a range of $10^{-3}$ to $10^{-5}$ Pa, and preferably in a range of $10^{-4}$ to $10^{-6}$ Pa, lower by an order of magnitude, for a practical use.

Loader Housing 40

Figure 16:
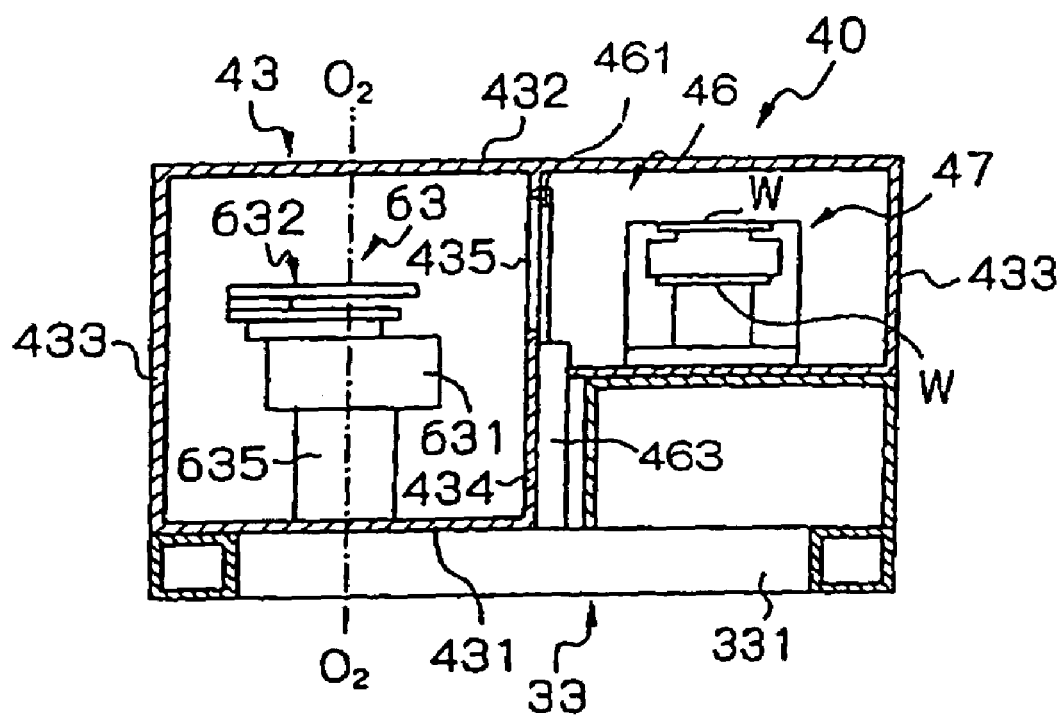
FIG. 16 is a diagram illustrating a loader housing for use with the inspection system illustrated in FIG. 12, taken along a line D—D in FIG. 13.

FIG. 16 illustrates an elevation of the loader housing 40 taken from a different direction from that in FIG. 12. As illustrated in FIGS. 16, 12, 13, the loader housing 40 comprising a housing body 43 which defines a first loading chamber 41 and a second loading chamber 42. The housing body 43 comprises a bottom wall 431, a top wall 432, a peripheral wall 433 which surrounds the four sides of the housing body 43, and a partition wall 434 for partitioning the first loading chamber 41 from the second loading chamber 43, and isolates the two loading chambers from the outside. The partition wall 434 is formed with an opening, i.e., a port 435 for passing or receiving a wafer W between the two loading chambers. Also, a portion of the peripheral wall 433 adjacent to the mini-environment device 20 and main housing 30 is formed with gates 436, 437. The housing body 43 of the loader housing 40 is carried on and supported by the frame structure 331 of the housing supporting device 33. Therefore, no vibrations are transmitted to the loader housing 40 from the floor.

While the access port 436 of the loader housing 40 is in alignment to the access port 226 of the housing 22 of the mini-environment device 20, a shutter 27 is disposed between these access ports 436 and 226 for selectively blocking communications between the mini-environment space 21 and the loading chamber 41. Also, while the access port 437 of the loader housing 40 is in alignment to the access port 325 of the housing body 32 of the main housing 30, a shutter 45 is disposed between these access ports 436 and 325 for selectively blocking communications between the loading chamber 42 and the working chamber 31 in a sealing structure. Further, a shutter 46 is disposed in an opening formed through the partition wall 434 for closing the opening with a door 461 to selectively block communications between the first and second loading chambers in a sealing structure. These shutters 27, 45, 46 can hermetically seal the respective chambers when they are closed.

A wafer rack 47 is arranged within the first loading chamber 41 for horizontally supporting a plurality (two in this embodiment) of wafers W one above another with a space defined therebetween.

The first and second loading chambers 41, 42 are controlled to be in a high vacuum state by a general-purpose evacuator (not shown) including a vacuum pump (the degree of vacuum is in a range of $10^{-5}$ to $10^{-6}$ Pa). In this event, the first loading chamber 41 is held in a low vacuum atmosphere to serve as a low vacuum chamber, while the second loading chamber 42 is held in a high vacuum atmosphere to serve as a high vacuum chamber, thereby making it possible to effectively prevent wafers from contamination. With the employment of such a loading housing structure which comprises two loading chambers, wafers W can be transferred from the loading chamber into the working chamber without delay. Also, the employment of such a loading chamber structure can improve the throughput of a test for defects and the like, and approach the degree of vacuum around the electron source, which must be held in a high vacuum state, to a highest possible vacuum state.

Each of the first and second loading chambers 41, 42 is connected to an evacuation pipe and a vent pipe (not shown) for an inert gas (for example, dry pure nitrogen). With this structure, inert gas vent (an inert gas is injected to prevent an oxygen gas and the like other than the inert gas from sticking to the surface) is achieved in an atmospheric condition within each loading chamber.

It should be noted that in the main housing 30 which uses electron beams, representative lanthanum hexaboride ($LaB_6$) or the like for use as an electron source, i.e., an electron gun of the opto-electro system 70 should essentially be brought into contact with oxygen or the like with the least possible frequency in order not to reduce the life time thereof. Since the electron source is brought into contact with oxygen with reduced possibilities by conducting the atmospheric control as mentioned above before the wafers W are loaded into the working chamber which contains the opto-electro system 70 of the main housing 30, the life time of the electron source is less likely to be reduced.

Stage Device 50

The stage device 50 comprises a fixed table 51 disposed on the bottom wall 321 of the main housing 30; a Y-table 52 for movements on the fixed table 51 in a Y-direction (in the direction perpendicular to the sheet surface in FIG. 12); an X-table 53 for movements on the Y-table 52 in an X-direction (a left-to-right direction in FIG. 12); a rotary table 54 rotatable on the X-table 53; and a holder 55 disposed on the rotary table 54. Wafers W are releasably held on a wafer carrying surface 551 of the holder 55. The holder 55 may be of a general-purpose structure for releasably chucking a wafer W mechanically or in an electrostatically chucking manner. The stage device 50 operates a plurality of tables 52–54 mentioned above using servo motors, encoders, and a variety of sensors (not shown) for highly accurately aligning a wafer W held by the holder 55 on the carrying surface 551 in the X-, Y-, and Z-directions (an up-to-down direction in FIG. 1), as well as in a rotating direction (θ direction) about an axis normal to the wafer supporting surface with respect to electron beams irradiated from the opto-electro system 70.

For aligning a wafer in the Z-direction, the position of the carrying surface 551 on the holder 55 may be made finely adjustable in the Z-direction, by way of example. In this event, a reference position on the carrying surface 551 may be sensed by a position measuring device using a micro-diameter laser (a later interferometric telemeter using the principle of interferometer) for control by a feedback circuit (not shown), and additionally or alternatively, the position of the notch or orientation flat on a wafer may be measured to sense a planar position and a rotating position of the wafer with respect to an electron beam, and the rotary table 54 is rotated by a stepping motor or the like which can be controlled to operate in small angular increments. The wafers W may be directly placed on the rotary table 54 without providing the holder 55. For maximally preventing dust from occurring within the working chamber 31, the servo motors 521, 531 and encoders 522, 532 for the stage device 50 are disposed outside the main housing 30.

By previously inputting a rotating position and a position on the X-Y coordinate of the wafer W with respect to the electron beam into a signal detection system or an image processing system, later described, signals can be scaled as well.

Further, the wafer chucking mechanism associated with the holder is applied with a voltage for chucking a wafer at electrodes of the electrostatic chuck, such that the wafer chucking mechanism fixes a wafer at three points (preferably equally distanced in the circumferential direction of the wafer) for positioning. The wafer chucking mechanism comprises two fixed positioning pins and one press-type cramp pin. The cramp pin can carry out automatic chucking and automatic releasing, and constitutes a component through which an applied voltage passes.

In this embodiment, the table which moves in the horizontal direction in FIG. 13 is designated the X-table, while the table which moves in the vertical direction in FIG. 13 is designated the Y-table, but alternatively, the table which moves in the horizontal direction in FIG. 13 may be designated a Y-table, while the table which moves in the vertical direction in FIG. 13 may be designated an X-table.

Wafer Chucking Mechanism

1) Basic Structure of Electrostatic Chuck:

For accurate and rapid focusing in the opto-electro system, ruggedness on the surface of a sample or a wafer is preferably as small as possible. Stated another way, when a substrate such as a wafer is tested, unless the substrate is appropriately fixed at a desired location on a stage, the wafer may be shifted during the test to hinder a comparison of images, which is relied on for the test, or a varying working distance can fail to satisfy a focusing condition, resulting in a failure in generating a clear image. As such, it is extremely important to appropriately fix a substrate such as a wafer at a desired location on the stage, and a chucking mechanism is required for fixing a wafer on the stage.

On the other hand, since the test is conducted within a inspection chamber which is in a high vacuum state, a vacuum chuck is not appropriate because it cannot act as an absorption mechanism. Therefore, a mechanical chuck or an electrostatic chuck is preferably employed for a chucking mechanism for use with the inspection apparatus of the present invention. The electrostatic chuck in particular is reliable because of fewer errors such as bowing, undulating and the like of wafer, as typically experienced with a mechanical chuck. Also, since a substrate must be applied with a retarding voltage during a test, the electrostatic chuck is most preferred for the inspection apparatus because it applies a voltage to a substrate for absorption of a wafer to the stage. Thus, a wafer is absorbed on the surface of an electrostatic chuck which is manufactured with a high flatness (flatness of 5 µm or less is preferable).

The structure for the electrode of the electrostatic chuck is classified into a monopole type and a dipole type. The monopole type electrostatic chuck previously brings a wafer into conduction, and applies a high voltage (generally approximately in a range of several tens to several hundreds of volts) between the single electrode of the electrostatic chuck and the wafer, to absorb the wafer. The dipole type electrostatic chuck need not bring a wafer into conduction, but can absorb a wafer by only applying a positive and a negative voltage to two electrodes of the electrostatic chuck, respectively. However, generally, for ensuring a stable absorption condition, the two electrodes must be formed into an interdigital shape, so that the electrodes are in a complicated shape.

On the other hand, for testing a sample, a wafer must be applied with a predetermined voltage (retarding voltage) in order to establish a focusing condition for the opto-electro system, or in order to facilitate electronic observations on the state of the surface of a sample. The electrostatic chuck must be the monopole type in order to apply the retarding voltage to a wafer and to stabilize the potential on the surface of the wafer. (However, the electrostatic chuck must be operated to be a dipole type until the wafer is brought into conduction with a conduction needle, as will be described later. To meet this requirement, the electrostatic chuck is configured to be switchable between a monopole mode and a dipole mode.) When the potential on the surface of the wafer is not stable at a predetermined value in each test mode, the focusing condition is not satisfied, resulting in a failure of generating a clear image. It is therefore necessary to securely confirm that the wafer is conducting before the application of the retarding voltage.

A procedure for confirming the conduction of a wafer begins with the placement of the wafer on the electrostatic chuck, and the absorption of the wafer by the electrostatic chuck. Subsequently, the wafer is brought into conduction using a conduction pin, followed by a confirmation made by an ampere meter as to whether or not the wafer is conducting. After confirming the conduction, the electrostatic chuck is switched to the dipole mode, and the retarding voltage is applied to the wafer using the conduction pin in association with the conduction confirmation operation. The foregoing procedure permits secure absorption of the wafer to the stage and smooth application of the retarding voltage, so that preparative operations can be extremely smoothly and securely performed for starting a test using the inspection apparatus.

While it must be confirmed without fail that a wafer is conducting before it is applied with the retarding voltage as described above, a mechanical contact with the wafer is involved in bringing the wafer into conduction. However, increasingly strict requirements are imposed on wafers for preventing contaminations, and it is therefore requested that a mechanical contact to a wafer be made with the least possible frequency, so that a contact to the edge of a wafer may not be permitted. In this event, the wafer must be brought into conduction through the back thereof.

A wafer is generally formed with a silicon oxide film on its back, so that the conduction cannot be established unless the silicon oxide film is partially removed from the back. To do this, needles are brought into contact with the back of the wafer at two or more locations, and a voltage is applied between the needles to locally break the oxide film, thereby making it possible to successfully bring the wafer into conduction. The voltage applied between the needles may be a DC voltage or an AC voltage of approximately several hundreds of volts. The needles are required to be made of a refractory material which is non-magnetic and wear-resistant, for example, tungsten. Further, for enhancing the durability or for preventing contaminations of wafers, the needles may be effectively coated with TiN or diamond. In addition, for confirming that the wafer is conducting, a voltage is effectively applied between the needles to measure a current with an ampere meter. By applying the retarding voltage after the confirmation of the conduction, the surface of the wafer can be charged with a desired potential, thus conducting a test while satisfying the focusing condition.

Figure 17:
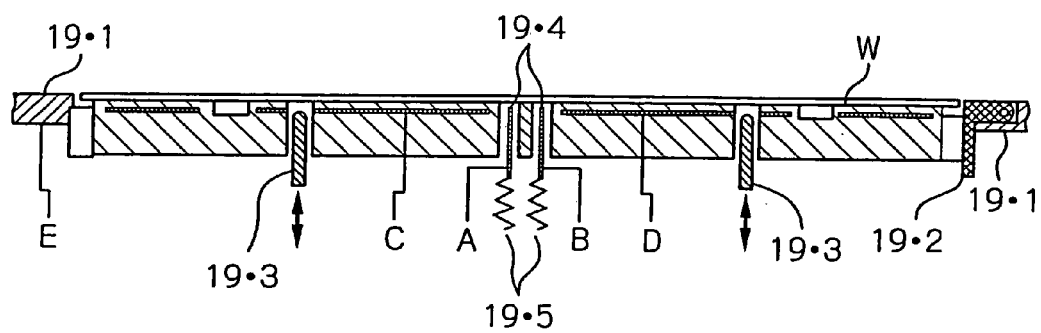
FIGS. 17(A) and 17(B) are diagrams for explaining an electrostatic chuck used in the electron beam apparatus according to the present invention.
Figure 17:
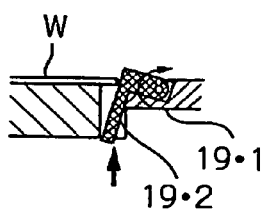

FIGS. 17(A) and 17(B) illustrate a chucking mechanism which has been created from the foregoing background. An electrostatic chuck is provided with electrodes 19-1, 19-2 which preferably have an interdigital shape for stably absorbing a wafer 17; three pusher pins 19-3 for passing a wafer; and two or more conduction needles 19-4 for applying a voltage to a wafer. In addition, a correction ring 19-1 and a wafer dropping mechanism 19-6 are disposed around the electrostatic chuck.

The pusher pins 19-3 previously protrude from the surface of the electrostatic chuck when a sample wafer W is transferred by a robot hand, and slowly move down as the wafer W is placed on the electrostatic chuck by the action of the robot hand to receive the wafer W on the electrostatic chuck. When a wafer W is removed from the electrostatic chuck, the pusher pins 19-3 perform the reverse actions to pass the wafer W to the robot hand. The pusher pins 19-3 must be made of a material which contributes to prevention of a shifted position and contamination of the wafer, and silicone rubber, rubber fluoride, ceramics such as SiC, alumina or the like, resin such as teflon, polyimide or the like, are preferably used for the pusher pins 19-3.

The pusher pins 19-3 can be driven by several possible methods. A first method involves the installation of a non-magnetic actuator below the electrostatic chuck. Specifically, the pusher pins are directly driven linearly by an ultrasonic linear motor, or the pusher pins are linearly driven by a combination of a rotary ultrasonic motor and a ball screw or a rack-and-pinion gear. With this method, the pusher mechanism can be integrated in compact on the table of the XY-stage on which the electrostatic chuck is mounted, whereas excessively many wires are required for actuators, limit sensors and the like. These wires run from the table on which the XY-stage operates to a wall surface of a sample chamber (main chamber or main housing), and bend in association with the actions of the stage, so that the wires must be routed with large radii of curvature, resulting in a need for a large space. Also, the wires can be a source of particles, and must be replaced on a periodic basis, so they should be used in a minimally required amount.

An alternative method may supply a driving force from the outside. As the stage is moved to a position at which a wafer is removed, a shaft protruding into a vacuum through a bellows is driven by an air cylinder disposed outside the chamber to push a shaft of a pusher driving mechanism disposed below the electrostatic chuck. The shaft is connected to a rack-and-pinion gear or a link mechanism within the pusher driving mechanism, such that reciprocal movements of the shaft are associated with up-and-down movements of the pusher pins. When a wafer W is passed to the robot hand, the pusher pins 19-3 are moved up by adjusting the speed to a proper level by a controller and pushing the shaft out into the vacuum by the air cylinder.

The external shaft driving force is not limited to the air cylinder, but may be implemented by a combination of a servo motor with a rack-and-pinion gear or a ball screw. Alternatively, the external driving source can be a rotary shaft. By this strategy, the rotary shaft is coupled through a vacuum sealing mechanism such as a magnetic fluid seal or the like, and the pusher driving mechanism contains a mechanism for converting rotations into linear motions of pusher pins.

The correction ring 19-1 has an action of holding a uniform electric field distribution around the edge of a wafer, and is basically applied with the same potential as the wafer. However, the correction ring 19-1 may be applied with a potential slightly different from the potential at the edge of the wafer in order to cancel out the influence of a narrow gap between the wafer and the correction ring, and of a small difference in height between the surfaces of the wafer and the correction ring. The correction ring 19-1 has a width of approximately 10–30 mm in a radial direction of the wafer, and can be made of a non-magnetic and conductive material, for example, titanium, phosphor bronze, TiN or Tic coated aluminum, or the like.

Each of the conduction needles 19-4 is supported by a spring 19-7, and as a wafer is placed on the electrostatic chuck, the conduction needles 19-4 are lightly urged onto the back of the wafer by the forces of the springs. In this state, a voltage is applied in a manner described above to bring the wafer into electric conduction.

The electrostatic chuck body comprises non-magnetic flat electrodes 19-1, 19-2 made of tungsten or the like, and dielectric films formed on the electrodes. The dielectric films may be made of alumina, aluminum nitride, polyimide or the like. Generally, ceramics such as alumina are perfect insulating materials having a volume resistivity of approximately $10^{14}$ Ocm, so that no charge migration occurs within the material, and a Coulomb force acts as an absorption force. However, by slightly adjusting the composition of ceramics, the volume resistivity can be reduced to approximately $10^{10}$ Ocm, permitting charges to migrate within the material to cause a so-called Jonson-Rahbeck force to act as a wafer absorption force which is stronger than the Coulomb force. The stronger the absorption force is, a correspondingly lower voltage can be applied to the wafer, a larger margin can be ensured for breakdown, and a stable absorption force is more likely to be provided. Also, by machining the surface of the electrostatic chuck into a dimple shape, particles or the like, even sticking to the surface of the electrostatic chuck, are likely to drop into valleys of dimples, leading to an expected effect of reducing the possibility of affecting the flatness of the wafer.

Bearing the foregoing discussion in mind, the electrostatic chuck suitable for practical use may be made of such material as aluminum nitride or alumina ceramics which is adjusted to have the volume resistivity of approximately $10^{10}$ Ωcm, and formed with ruggedness such as dimples on the surface which is machined such that a surface formed of a collection of convex portions has a flatness of approximately 5 μm.

Figure 18:
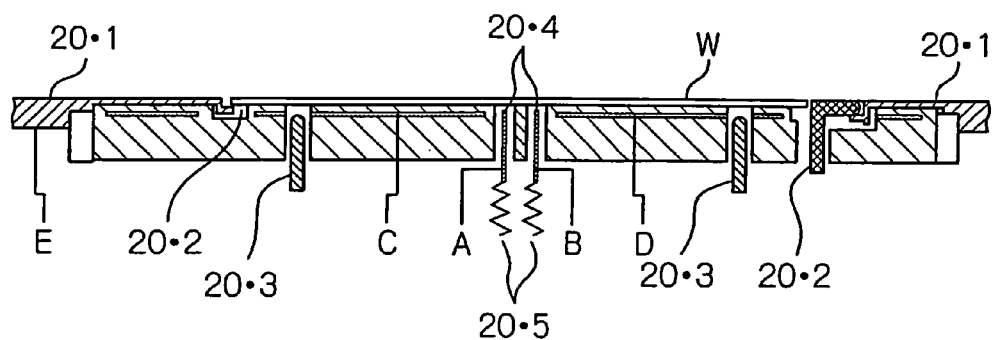
FIG. 18 is a diagram for explaining another exemplary electrostatic chuck used in the electron beam apparatus according to the present invention.

2) Chucking Mechanism for 200/300 Bridge Tool:

The inspection apparatus may be required to test two types of wafers of 200 mm and 300 mm diameters without mechanical modifications. In this event, the electrostatic chuck must have the ability to chuck the wafers in two sizes, and a correction ring compatible with the two wafer sizes must be provided along the periphery of the wafer. FIGS. 17(A), 17(B) and 18 illustrate the structure for meeting the foregoing requirements.

FIG. 17(A) illustrates how a 300-mm wafer W is placed on the-electrostatic chuck. The correction ring 19-1, which has an inner diameter slightly larger than the size of the wafer W (defining a gap of approximately 0.5 mm therebetween), is positioned by and carried on a metal ring part disposed along the outer periphery of the electrostatic chuck with a spigot joint. The correction ring 19-1 is provided with wafer dropping mechanisms 19-2 at three locations. Each of the wafer dropping mechanisms 19-2 is driven by a vertical driving mechanism associated with a mechanism for driving the pusher pins 19-3, and is supported for rotation about the rotating shaft arranged in the correction ring 19-1.

When a wafer W is received from a robot hand, the pusher pin driving mechanism operates to push up the pusher pins 19-3. The wafer dropping mechanisms 19-2 provided in the correction ring 19-1 also receive a driving force to rotate at a timing appropriate to the operation of the pusher pin driving mechanism, as illustrated in FIG. 17(B). Consequently, each wafer dropping mechanism 19-2 forms a tapered surface for guiding the wafer W about the electrostatic chuck. Next, after the wafer W is placed on the pusher pins 19-3 thus pushed up, the pusher pins 19-3 are moved down. By adjusting a timing at which the driving force acts on the wafer dropping mechanism 19-2 to be appropriate to the lowering of the pusher pins 19-3, the wafer W is placed on the electrostatic chuck such that the center of the wafer W substantially matches the center of the electrostatic chuck while the position of the wafer W is modified by the tapered surfaces of the wafer dropping mechanisms 19-2.

Desirably, the tapered surface of each wafer dropping mechanism 19-2 is coated with a low-friction material such as Teflon, or preferably a conductive low-friction material (for example, conductive Teflon, conductive diamond-like carbon, TIN coating). In FIG. 17(A), terminals A, B, C, D and E are applied with respective appropriate voltages (later described), and wafer conduction needles 19-4 sense that a wafer W is placed on the electrostatic chuck, and are pushed up by associated springs 19-5.

FIG. 18 illustrates a 200-mm wafer W placed on the same electrostatic chuck. Since the surface of the electrostatic chuck is exposed due to the diameter of the wafer smaller than that of the electrostatic chuck, the electrostatic chuck is mounted with a correction ring 20-1 which has a size large enough to completely cover the electrostatic chuck. The positioning of the correction ring 20-1 is performed in a similar manner to the correction ring for 300-mm wafer.

The correction ring 20-1 is formed with a step along the inner periphery, such that the step fits into an annular groove 20-2 of the electrostatic chuck. This is a structure for covering the surface of the electrostatic chuck with a conductor (correction ring 20-1), when a 200-mm wafer W is placed on the electrostatic chuck, such that the surface of the electrostatic chuck is invisible from the gap between the inner periphery of the correction ring 20-1 and the outer periphery of the wafer W. If the surface of the electrostatic chuck were visible, charges would be accumulated on the surface of the electrostatic chuck when electron beams are irradiated and would cause disturbance of the potential on the surface of the sample.

For replacing the correction ring 20-1, a correction ring replacement station has been installed at a predetermined location within the vacuum chamber, and a correction ring of a required size is transferred by a robot from the station, and mounted on the electrostatic chuck (inserted into a spigot joint).

The 200-mm wafer correction ring is also provided with wafer dropping mechanisms 20-2 similar to those of the 300-mm wafer correction ring. The electrostatic chuck is formed with relief portion for preventing interference with the wafer dropping mechanisms 20-2. A 200-mm wafer is placed on the electrostatic chuck completely in the same manner as the 300-mm wafer. The electrostatic chuck comprises terminals A, B, C, D, E for receiving respective appropriate voltages, push pins 30-3 similar to the push pins 19-3, and wafer conduction needles 20-4 similar to the wafer conduction needles 19-4.

FIGS. 19(A) and 19(B) generally illustrate the configuration of an electrostatic chuck which can support both of 300-mm wafer and 200-mm wafer, wherein FIG. 19(A) illustrates a 300-mm wafer placed on the electrostatic chuck, and FIG. 19(B) illustrates a 200-mm wafer placed on the electrostatic chuck. As is understood from FIG. 19(A), the electrostatic chuck has an area large enough to accommodate a 300-mm wafer, and as illustrated in FIG. 19(B), a central portion of the electrostatic chuck has an area large enough to accommodate a 200-mm wafer. A groove 20-6 is formed to surround the central portion of the electrostatic chuck for fitting the inner periphery of the correction ring 20-1. The electrostatic chuck also comprises terminals A, B, C, D and E for receiving respective appropriate voltages.

In the electrostatic chuck illustrated in FIGS. 19(A) and 19(B), detections may be optically made as to whether or not a wafer is placed on the electrostatic chuck, whether or not a wafer is correctly placed on the electrostatic chuck, whether or not the correction ring is used, and the like. For example, an optical sensor may be disposed above the electrostatic chuck, in which case detection can be made as to whether a wafer is evenly placed or is inclinedly placed by measuring the length of an optical path when light emitted from the optical sensor is reflected back by the wafer to return again to the optical sensor. Also, the presence or absence of the correction ring can be detected by a light emitter which inclinedly emits light to an appropriate point within the area on which the correction ring should be mounted, and a light receiver which receives reflected light from the correction ring. Further, it is possible to detect which of the 300-mm wafer correction ring or 200-mm wafer correction ring is mounted on the electrostatic chuck by providing a combination of a light emitter which inclinedly emits light to an appropriate point in the area on which the 200-mm wafer correction ring should be mounted and a light receiver which receives reflected light from the correction ring, and a combination of a light emitter which inclinedly emits light to an appropriate point in the area on which the 300-mm wafer correction ring should be mounted and a light receiver which receives reflected light from the correction ring, and detects which light receiver receives the reflected light.

3) Wafer Chucking Procedure:

The wafer chucking mechanism which has the structure described above chucks a wafer in the following procedure.

(1) A correction ring suited to a wafer size is transferred by a robot, and mounted on the electrostatic chuck.

(2) The wafer is transferred by a robot hand, and placed on the electrostatic chuck through vertical movements of the pusher pins.

(3) The electrostatic chuck is applied with voltages (a positive and a negative voltage are applied to the terminals C and D, respectively) in the dipole mode to absorb the wafer.

(4) A predetermined voltage is applied across the conduction needles to break the insulating film (oxide film) on the back of the wafer.

(5) A current between the terminals A and B is measured to confirm whether or not the wafer is conducting.

(6) The electrostatic chuck is switched to the monopole absorption mode (a ground potential GRD is applied to the terminals A, B, while the same voltage is applied to the terminals C and D).

(7) The voltage at the terminal A (or B) is reduced while maintaining a potential difference between the terminal A (or B) and the terminal C (or D), and the wafer is applied with a predetermined retarding voltage.

Configuration of Apparatus for 200/300 Bridge Tool

Figure 20:
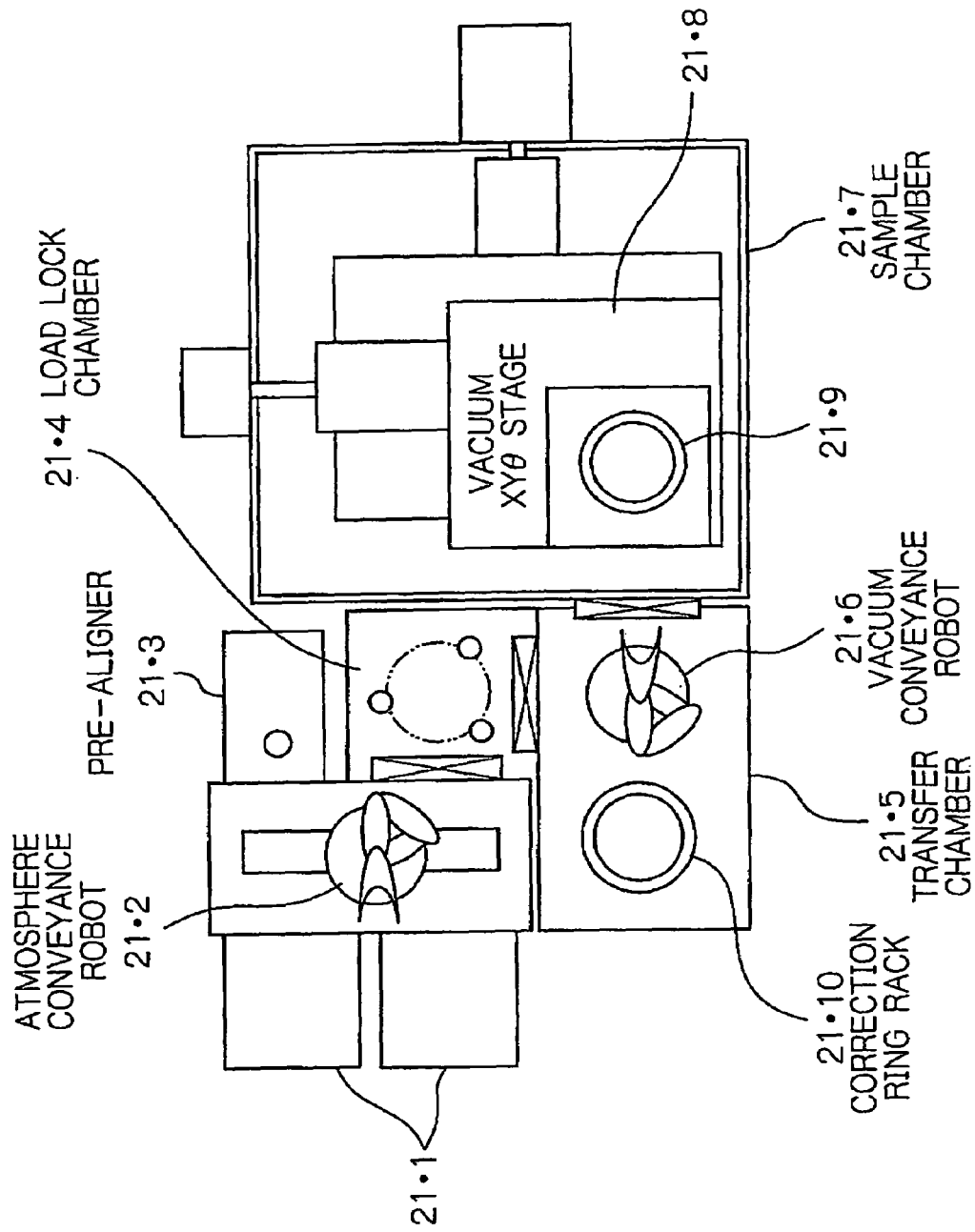
FIG. 20 is a diagram for explaining a bridge tool used in the electron beam apparatus according to the present invention.
Figure 21:
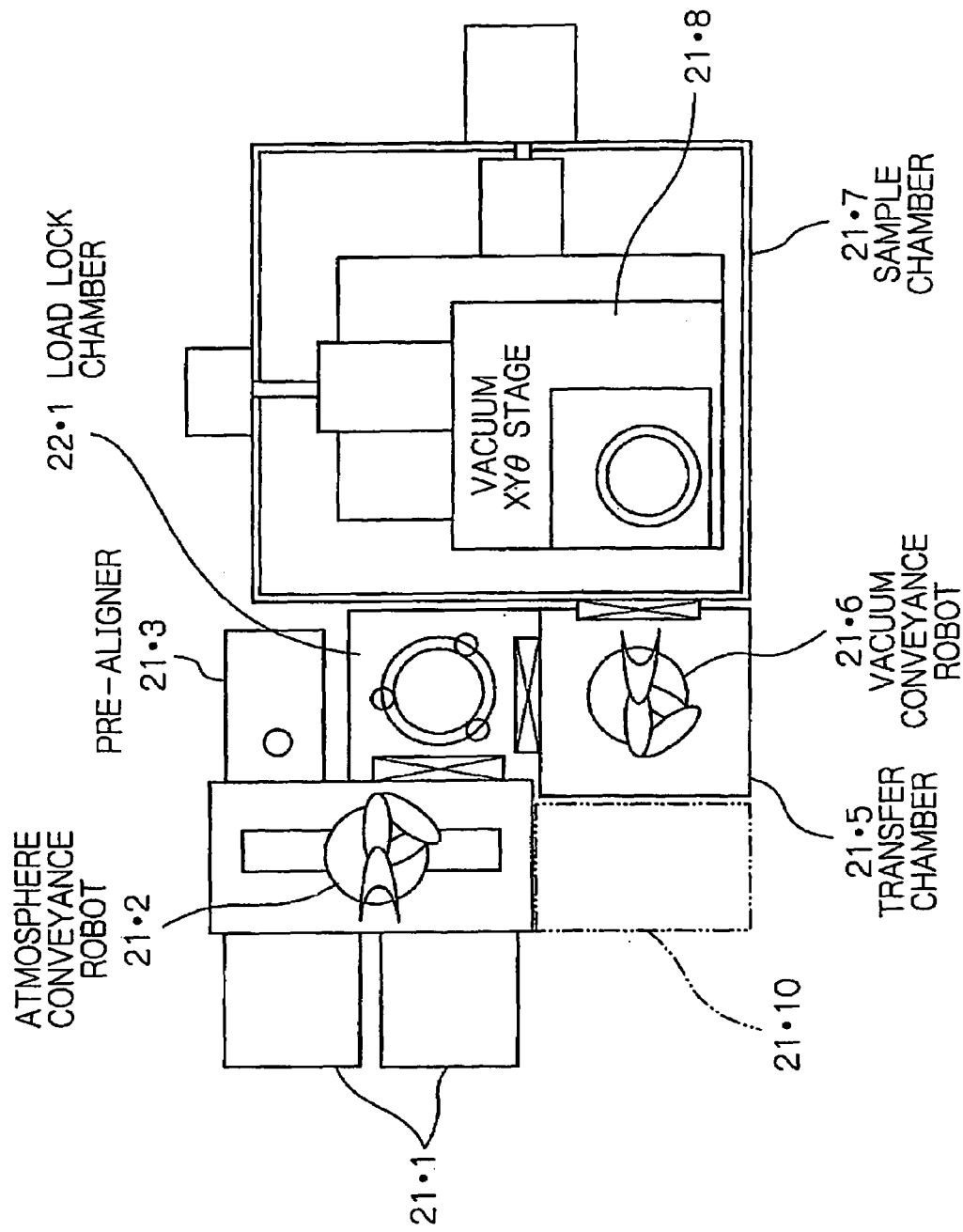
FIG. 21 is a diagram for explaining another exemplary bridge tool used in the electron beam apparatus according to the present invention.

Each of FIGS. 20 and 21 illustrates a detection system which is capable of testing either of 200-mm wafers and 300-mm wafers without mechanical modifications. The following description will be centered on aspects different from inspection apparatuses dedicated to 200-mm wafers or 300-mm wafers.

In storage spaces 21-1 for storing wafer cassettes which are picked up in accordance with particular specifications such as 200/300-mm wafer, FOUP, SMIF, open cassette and the like, a variety of wafer cassettes can be stored in accordance with wafer sizes and types of wafer cassettes determined by specifications determined by the user. An atmosphere transfer robot 21-2 has a hand which can support different sizes of wafers, and more specifically, is formed with a plurality of wafer receiving steps suited to respective wafer sizes, such that a wafer is placed on the hand at a location appropriate to its size. The atmosphere transfer robot 21-2 transfers wafers from the storage space 21-1 to a pre-aligner 21-3 to adjust the orientation of the wafers, and then removes the wafers from the pre-aligner 21-3 for delivery into a load lock chamber 21-4.

A wafer rack within the load lock chamber 21-4, which is also in a similar structure, has a wafer support formed with a plurality of receiving steps suited to respective wafer sizes. The robot hand is adjusted in height such that a group of wafers fit into the receiving step suited to their size. The wafers placed on the hand of the atmosphere transfer robot 21-2 are loaded into a wafer rack, and then the robot hand is moved down to fit the wafers into a predetermined receiving step of the wafer support.

Each of the wafers placed in the wafer rack within the load lock chamber 21-4 is next removed from the load lock chamber 21-3 by a vacuum transfer robot 21-6 arranged in a transfer chamber 21-5, and transferred onto a stage 21-8 within a sample chamber 21-7. The vacuum transfer robot 21-6 also has a hand which is formed with a plurality of receiving steps suited to respective wafer sizes, similar to the atmosphere transfer robot 21-2. The wafer fitted into a predetermined receiving step of the robot hand is placed on the electrostatic chuck which has been previously mounted with a correction ring suited to the wafer size, and securely absorbed by the electrostatic chuck. The correction ring 21-9 is placed on a correction ring rack 21-10 disposed within the transfer chamber 21-5. Here, the vacuum transfer robot 21-6 picks up a correction ring 21-9 suited to the wafer size from the correction ring rack 21-10, and mounts the correction ring onto the electrostatic chuck. After fitting the correction ring 21-9 into a positioning spigot joint formed on the outer periphery of the electrostatic chuck, the wafer is placed on the electrostatic chuck.

When a correction ring is to be replaced with another one, operations reverse to the foregoing are performed. Specifically, the correction ring 21-9 is removed from the electrostatic chuck by the robot 21-6, and transferred back into the correction ring rack 21-10 within the transfer chamber 21-5. Then, a correction ring suited to the size of a wafer which is to be tested is transferred from the correction ring rack 21-10 to the electrostatic chuck.

In the inspection apparatus illustrated in FIG. 20, the pre-aligner 21-3 is positioned near the load lock chamber 22-4, so that even if a correction ring cannot be mounted in the load lock chamber due to an improperly aligned wafer, the wafer can be readily transferred back to the pre-aligner to again align the wafer, thus advantageously reducing a time loss in the process.

FIG. 21 illustrates an exemplary inspection system in which correction rings are stored at different places. The correction ring rack 21-10 incorporated in the system of FIG. 20 is omitted. The load lock chamber 22-1 is formed with a wafer rack and a correction ring lack in a layered structure. These racks are installed on an elevator and can therefore be moved up and down. First, for mounting the electrostatic chuck with a correction ring suited to the size of a wafer which is to be tested, the elevator of the load lock chamber 22-1 is moved to a position at which the vacuum transfer robot 21-6 can pick up the correction ring. Then, after the correction ring has been mounted on the electrostatic chuck by the vacuum transfer robot 21-6, the elevator is operated to carry a wafer to be tested, and the wafer is removed from the wafer rack by the vacuum transfer robot 21-6, and then placed on the electrostatic chuck. This configuration, though the elevator is required in the load lock chamber 22-1, can effectively reduce the vacuum transfer chamber 21-5 held in volume, and also reduce the foot print of the apparatus.

While a sensor for sensing whether or not a wafer is placed on the electrostatic chuck is preferably disposed at a position at which the sensor can support any of different wafer sizes, a plurality of sensors which are identical in function may be provided for respective wafer sizes if such a position is not available.

Using the algorithm as described above, an alignment of a wafer on the stage is conducted.

Now, description will be made of a whole procedure for a defect test.

Figure 22:
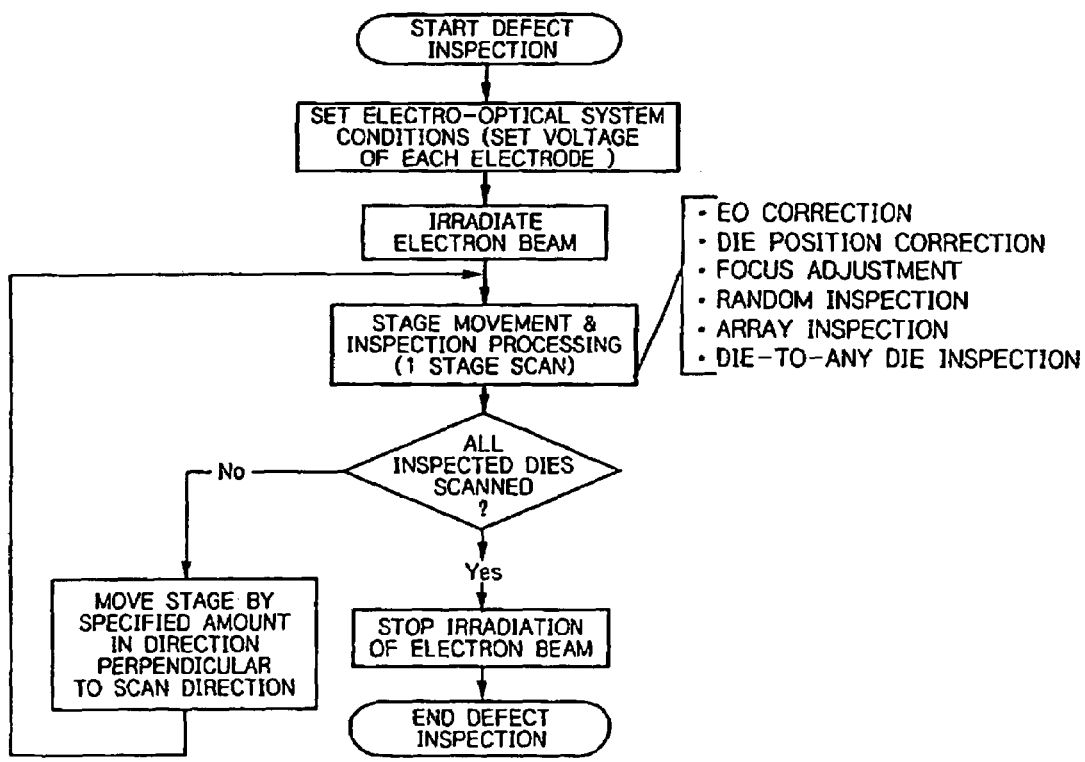
FIG. 22 is a diagram for explaining a defect inspection procedure in the electron beam apparatus according to the present invention.
Figure 23:
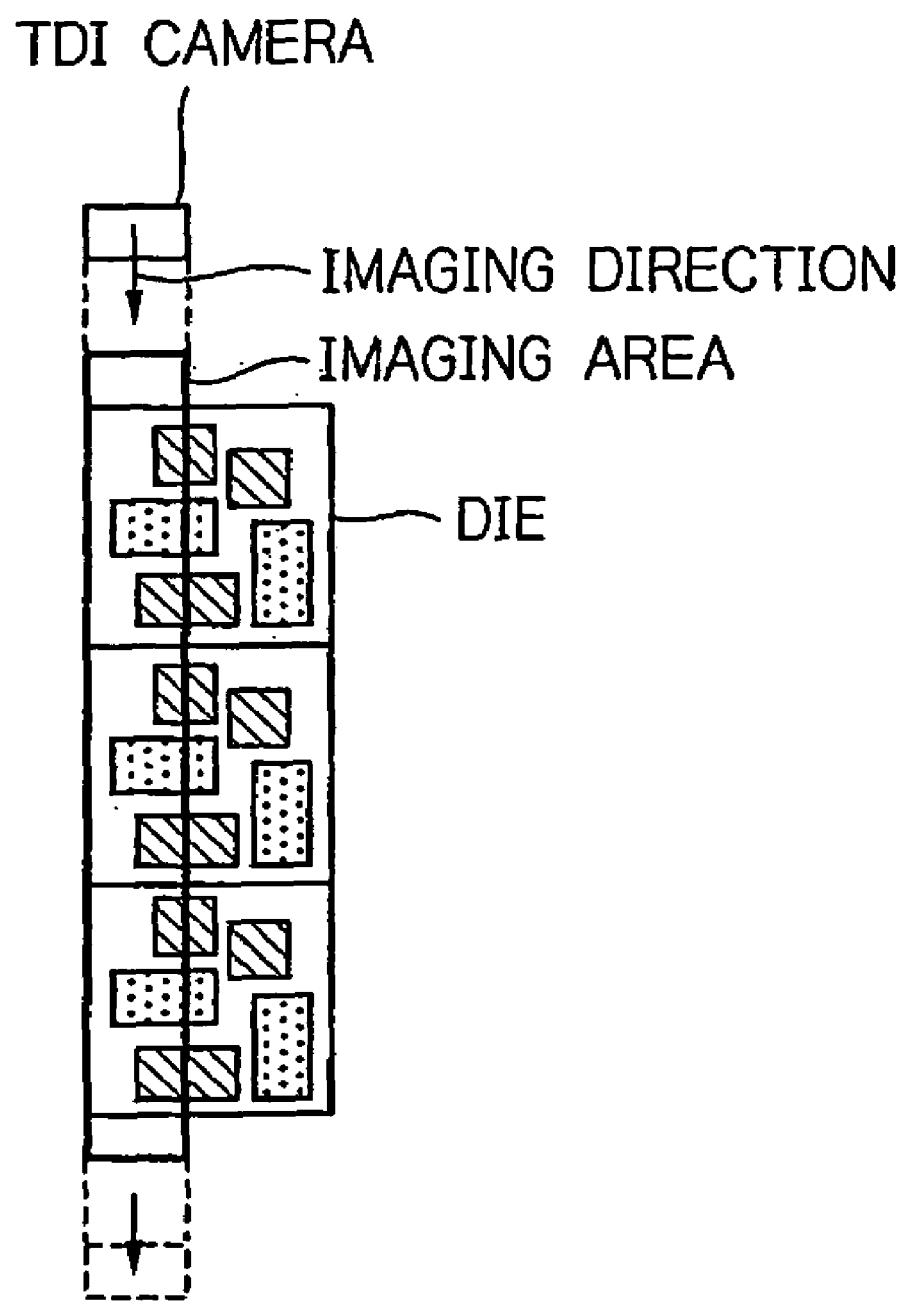
FIG. 23 is a diagram for explaining a defect inspection procedure in the electron beam apparatus according to the present invention.

As illustrated in FIG. 22, the defect test involves moving the stage while irradiating electron beams for TDI scan imaging (FIG. 23), and using a test dedicated processing unit (IPE) in accordance with set inspection conditions (an array inspection condition, a random inspection condition, an area under inspection) for inspecting a sample for defects in real time.

Figure 24:
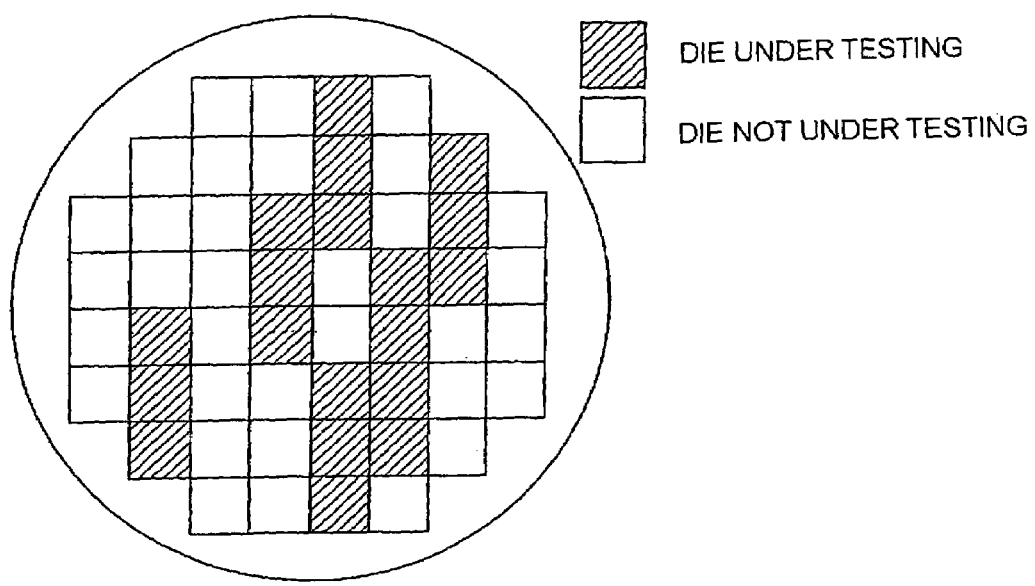
FIGS. 24(A) and 24(B) are diagrams for explaining a defect inspection procedure in the electron beam apparatus according to the present invention.
Figure 24:
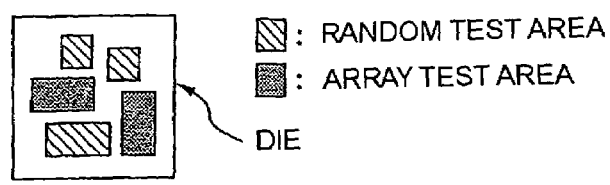

Inspection recipes or prescriptions set conditions for the opto-electro systems, dies under inspection, area under inspection, a inspection method (random/array), and the like (FIGS. 24(A) and 24(B)).

For capturing stable images for the defect test, the inspection apparatus simultaneously makes an EO correction for limiting the shaking of captured images due to shifted positions, speed variations and the like; a die position correction for absorbing an error between an ideal placement on a die map and an actual die position; and a focus adjustment for compensating for a focus value of the overall wafer area using a focus value previously measured at a finite measuring point in real time.

Figure 25:
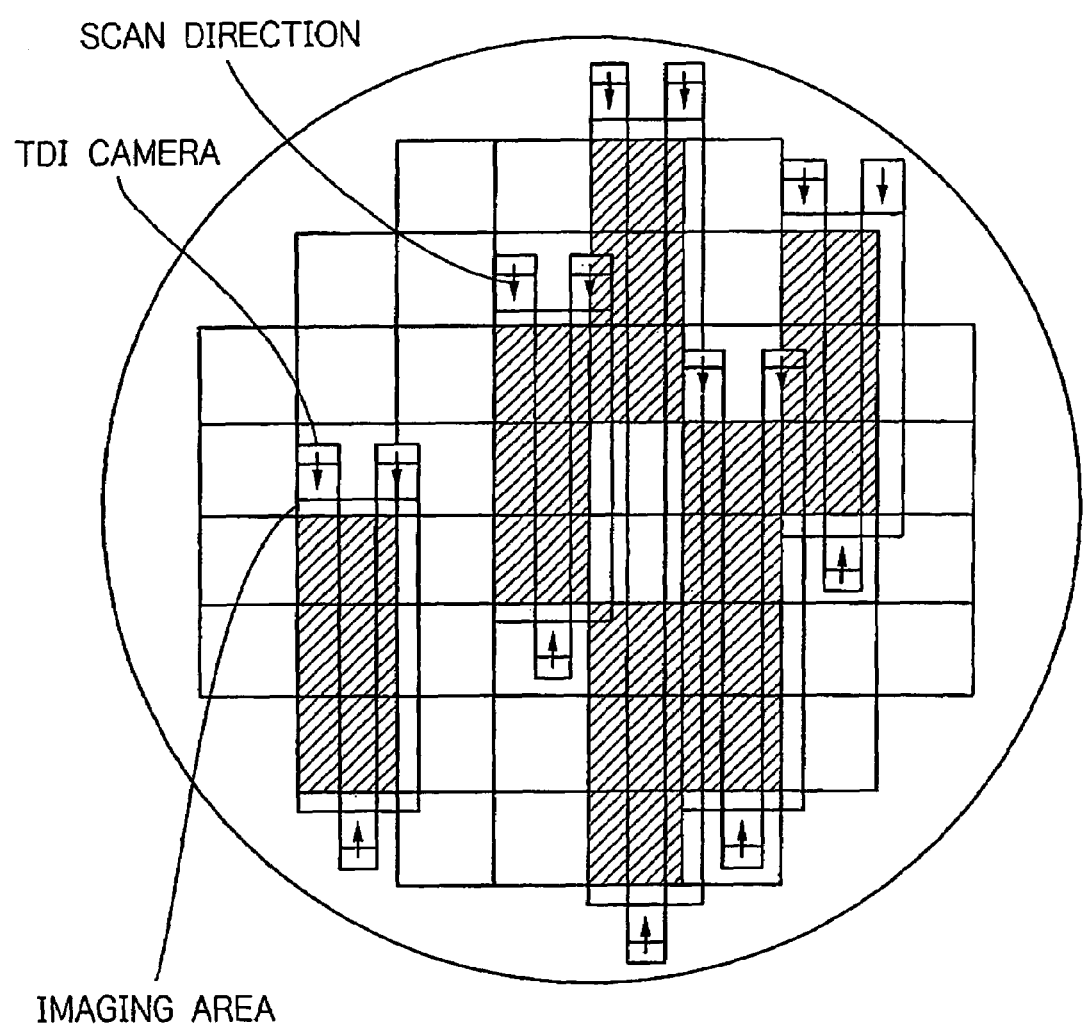
FIG. 25 is a diagram for explaining a defect inspection procedure in the electron beam apparatus according to the present invention.
Figure 26:
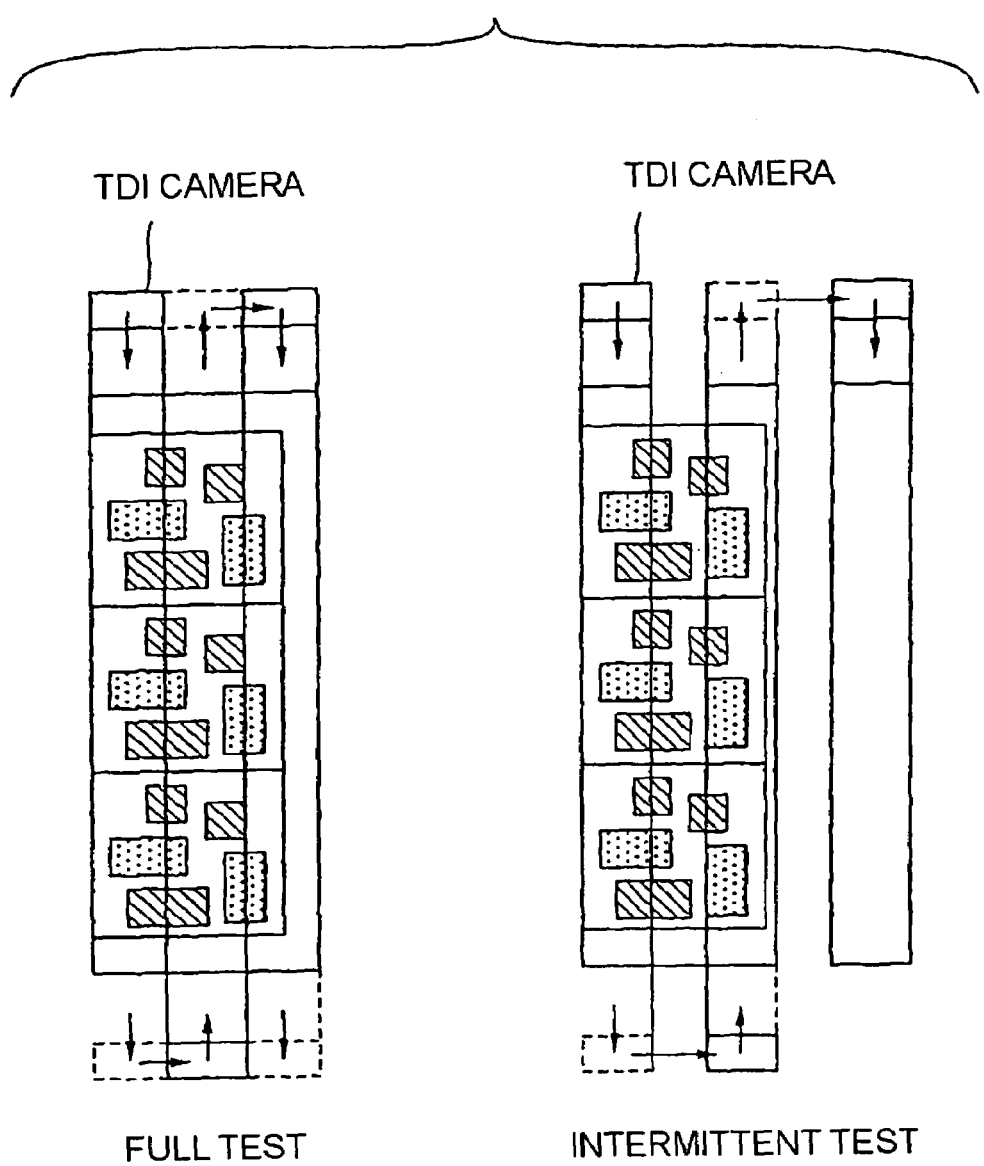
FIG. 26 is a diagram for explaining a defect inspection procedure in the electron beam apparatus according to the present invention.

In a scanning operation involved in the defect test, instead of testing the entire area of a die under inspection (FIG. 25), an intermittent test can also be made by adjusting step moving increments in a scanning direction and an orthogonal direction, as illustrated in FIG. 26 (for reducing a test time).

After completion of the test, the result of the test is displayed on a display device, including the number of defects, positions of the dies including defects, sizes of the defects, positions of defects within each die, types of defects, images of the defects, and images for comparison. If the foregoing information, recipe information and the like are saved in a file, the results of past tests can be confirmed and reproduced.

Figure 27:
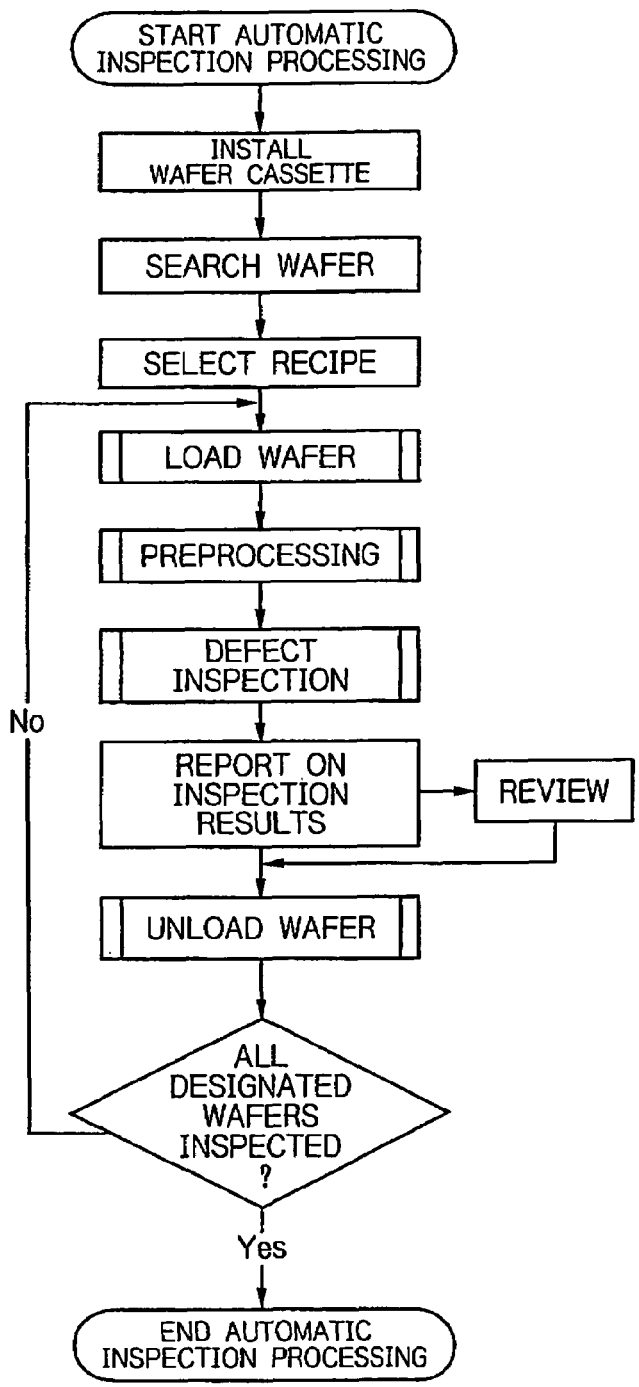
FIGS. 27(A) and 27(B) are diagrams for explaining a defect inspection procedure in the electron beam apparatus according to the present invention.
Figure 27:
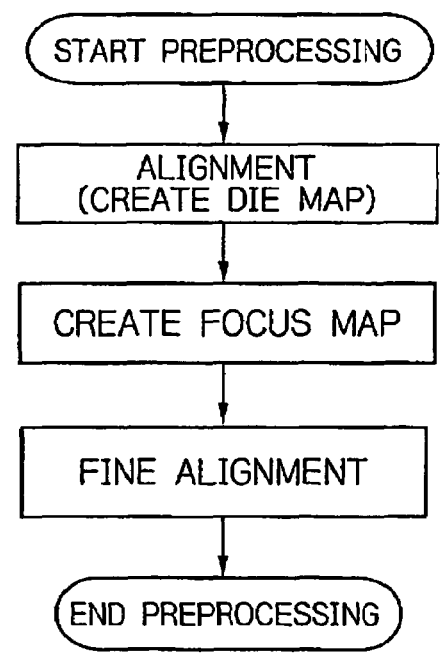

During an automatic defect test, a selection of a variety of recipes triggers loading a wafer in accordance with a transfer recipe, aligning the wafer on the stage in accordance with an alignment recipe, setting focus conditions in accordance with a focus map recipe, conducting a test in accordance with a test recipe, and unloading the wafer in accordance with the transfer recipe (FIGS. 27(A) and 27(B)).

Control Device 2

Figure 28:
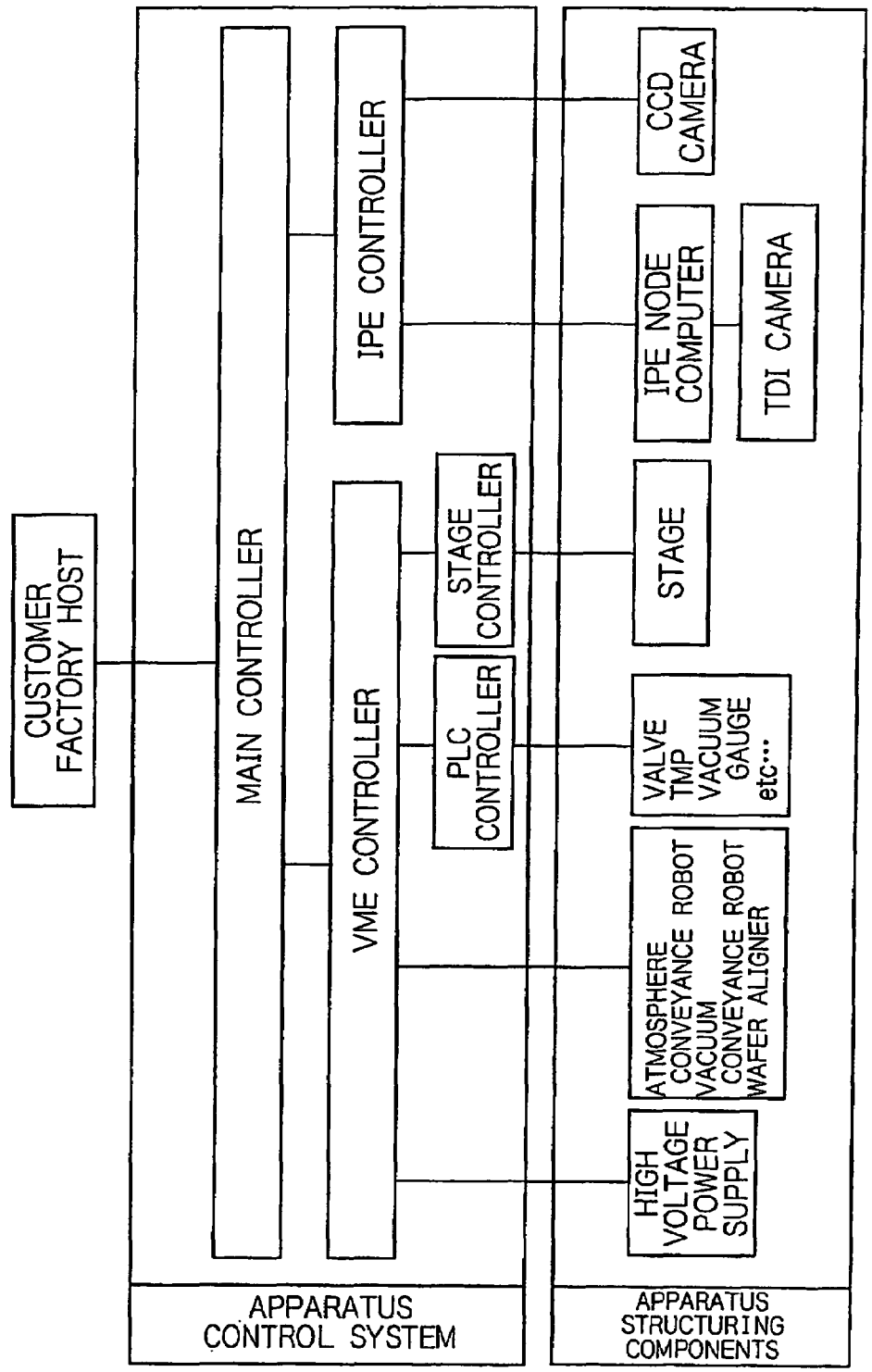
FIG. 28 is a diagram for explaining the configuration of a control system in the electron beam apparatus according to the present invention.

The control device 2 (FIG. 12) for the defect test comprises a plurality of controllers as illustrated in FIG. 28.

A main controller, which governs a GUI unit and sequence operations of the apparatus (EBI), receives operation instructions from a factory host computer or GUI, and gives necessary instructions to a VME controller and an IPE controller. The main controller is provided with a man-machine interface through which the operator performs operations (entering a variety of instructions/commands, recipes and the like, instructing the start of a test, entering all necessary commands for switching between an automatic and a manual test mode, commands involved in the manual test mode, and the like). Otherwise, the main controller is responsible for communications with the host computer in the factory, control of an evacuation system, transfer of wafers, control of positioning, transmission of commands to and reception of information from a stage controller and other controllers, and the like. The main controller also has a stage vibration correcting function for capturing an image signal from an optical microscope and feeding a stage fluctuation signal back to the opto-electro system to correct deteriorated images, and an automatic focus correcting function for detecting a displacement of a wafer observation position in the Z-axis direction (axial direction of the secondary optical system) and feeding the detected displacement to the opto-electro system to automatically correct the focus. The transmission and reception of feedback signals to and from the opto-electro system, as well as the transmission and reception of signals to and from the stage device are performed through the IPE controller and stage controller, respectively.

The VME controller governs the operation of component devices of the apparatus (EBI), and gives instructions to the stage controller and PLC controller in accordance with instructions from the main controller.

The IPE controller acquires defect test information from an IPE node computer, classifies acquired defects, and displays-images of the defects thus classified. The IPE node computer acquires images output from a TDI camera, and conducts a defect test. The IPE node computer also controls the opto-electro system 70, i.e., controls the electron gun, lenses, aligner and the like. The IPE node computer controls automatic voltage setting and the like for the respective lens systems and aligner corresponding to each operation mode (associative control); for example, controlling a power supply such that a constant electron current is irradiated to a target area at all times even if a different scaling factor is selected, and automatically setting voltages to the respective lens systems and aligner corresponding to each scaling factor.

The PLC controller receives instructions from the VME controller, drives devices such as valves, acquires sensor information, and monitors for abnormalities such as an abnormal degree of vacuum which must be monitored at all times.

The stage controller receives instructions from the VME controller, and moves the stage in the X- and Y-directions as well as rotating a wafer placed on the stage. In particular, the stage controller enables precise movements on the order of μm in the X-axis direction and Y-axis direction (with a tolerance of approximately ±0.5 μm), and also enables a control in the rotating direction (θ control) within an error accuracy of approximately ±0.3 seconds.

With the configuration of a distributed control system as described above, even if a component device is changed at an end, no change is required in software and hardware of higher rank controllers, due to maintaining the same interfaces between the respective controllers. Also, even if a sequence operation is added or modified, a flexible support can be provided for a change in configuration by minimizing changes in higher rank software and hardware.

User Interface

Figure 29:
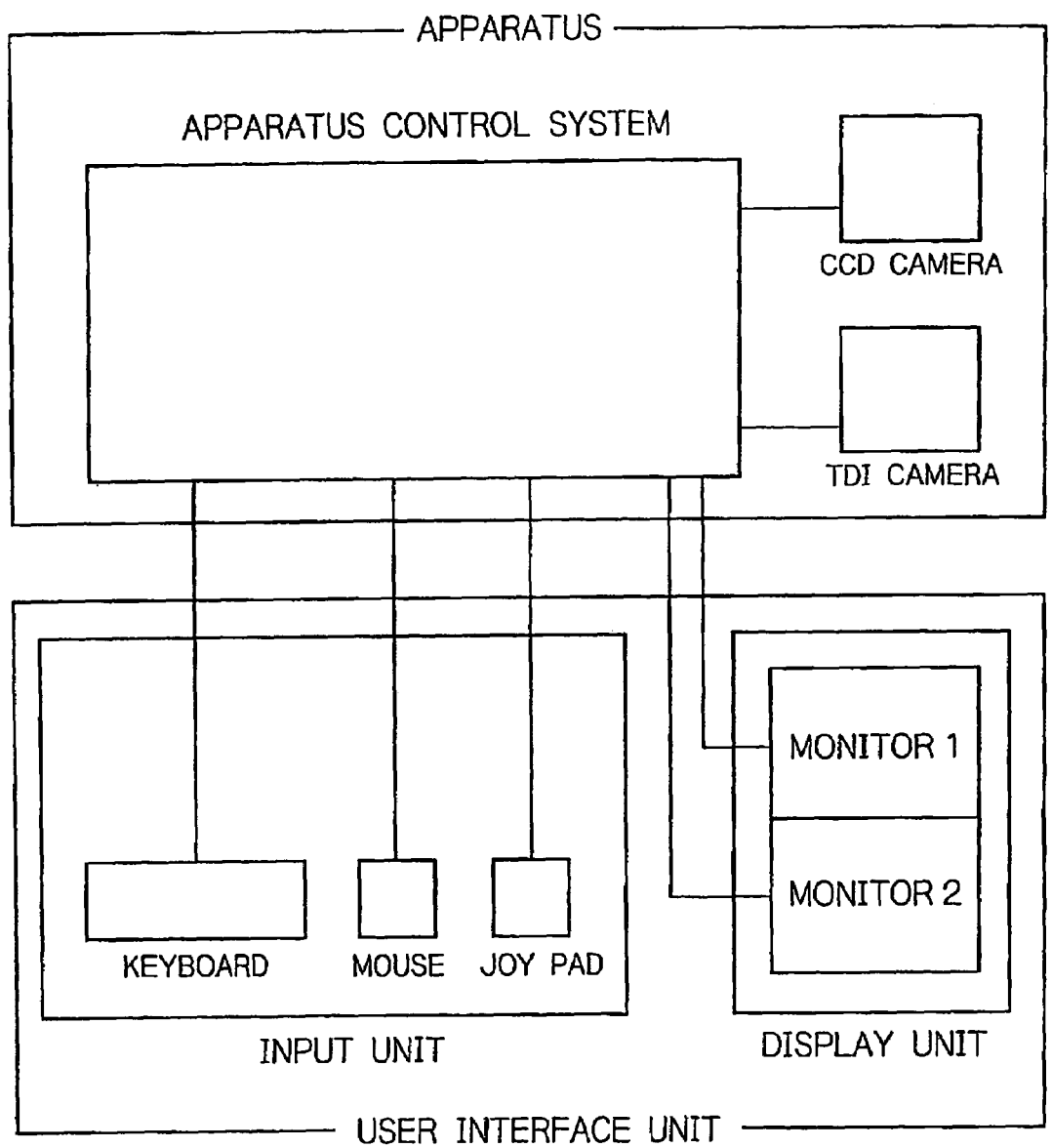
FIG. 29 is a diagram for explaining the configuration of a user interface in the electron beam apparatus according to the present invention.

FIG. 29 illustrates a device configuration in the user interface.

An input section shows devices which receive entries from the user, and comprises "keyboard," "mouse," and "JOY pad."

A display section shows devices for displaying information to the user, and comprises two monitors. A monitor 1 displays an image captured by a CCD camera or a TDI camera, while a monitor 2 displays a GUI screen.

Additionally, the progress of a test may be displayed on the screen in real time using different colors. The progress of a test will become apparent if different colors are used to display wafer location information indicative of where a certain wafer is found, and information on wafers under inspection such as to which stage the test has been made, where defects are found on each wafer, and the like. Also, dies under inspection may be displayed every swath.

The present apparatus defines the following three coordinate systems.

(1) Stage Coordinate System [$X_S$, $Y_S$]

This is the reference coordinate system for indicating a position during stage position control, and only one stage coordinate system exists in the apparatus.

The lower left corner of the chamber is defined to be the origin, and the X-coordinate value increases in the right direction, while the Y-coordinate value increases in the upward direction.

A position (coordinate values) represented by the stage coordinate system is the center of the stage (the center of a wafer). In other words, when coordinate values [0, 0] are specified in the stage coordinate system, the center of the stage (center of a wafer) moves to match the origin of the stage coordinate system.

The unit is [μm], but a minimum resolution is defined to be $\lambda/1,024$ (~0.618 [μm]), where $\lambda$ is the wavelength of a laser used in a laser interferometer ($\lambda$–632.991 [μm]).

(2) Wafer Coordinate System [$X_W$, $Y_W$]

This is a reference coordinate system for indicating a position on a wafer which is to be observed (imaged and displayed), and only one wafer coordinate system exists in the apparatus.

The center of a wafer is defined to be the origin, and the X-coordinate value increases in the right direction, while the Y-coordinate value increases in the upward direction. A position indicated in the wafer coordinate system (coordinate values) is the center of imaging in an imaging device (CCD camera, TDI camera) selected at that time.

The unit is [μm], but a minimum resolution is defined to be λ/1,024 (–0.618 [μm]), where λ is the same as the foregoing.

(3) Die Coordinate System $[X_D, Y_D]$

This is a reference coordinate system for defining a position on each die which is to be observed (imaged and displayed), and exists on each die.

The lower left corner of each die is defined to be the origin, and the X-coordinate value increases in the right direction, while the Y-coordinate value increases in the upward direction.

The unit is [μm], but a minimum resolution is defined to be λ/1,024 (–0.618 [μm]), where λ is the same as the foregoing.

Dies on a wafer are numbered, and a die which is the basis for the numbering is called the "origin die." By default, the origin die is the one closest to the origin of the wafer coordinate system, but the position of the origin die can be selected in response to a designation of the user.

Figure 30:
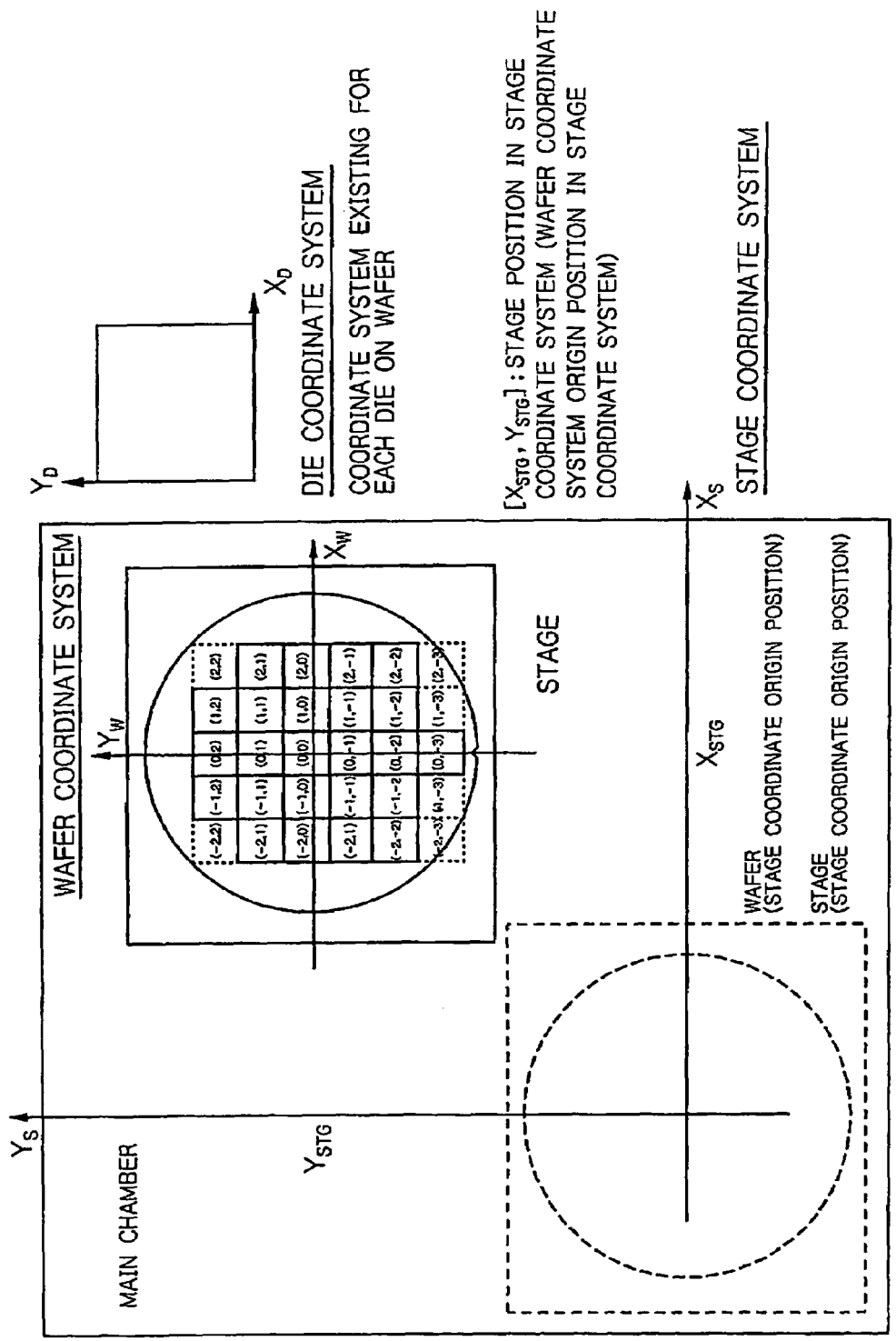
FIG. 30 is a diagram for explaining the configuration of the user interface in the electron beam apparatus according to the present invention.

The relationship between the coordinate values in the respective coordinate systems and a position at which an observation (display) is made is as shown in FIG. 30. Also, the relationship between coordinates indicated by the user interface and a direction in which the stage is moved is as described below.

(1) Joy Stick & GUI Arrow Buttons:

A direction indicated by the joy stick and a GUI arrow button is assumed to be a direction in which the operator wishes to view, so that the stage is moved in the direction opposite to the indicated direction.

EXAMPLE

Indicated Direction: Right . . . Stage Moving Direction: Left (an image moves to the left=the field of view moves to the right)

Indicated Direction: Upward . . . Stage Moving Direction: Downward (an image moves downward=the field of view moves upward)

(2) Direct Entry of Coordinates on GUI:

Coordinates directly entered on the GUI are regarded as a location at which the operator wishes to view on the wafer coordinate system, so that the stage is moved such that the coordinate on a wafer are displayed at the center of a captured image.

Figures 1, 31:
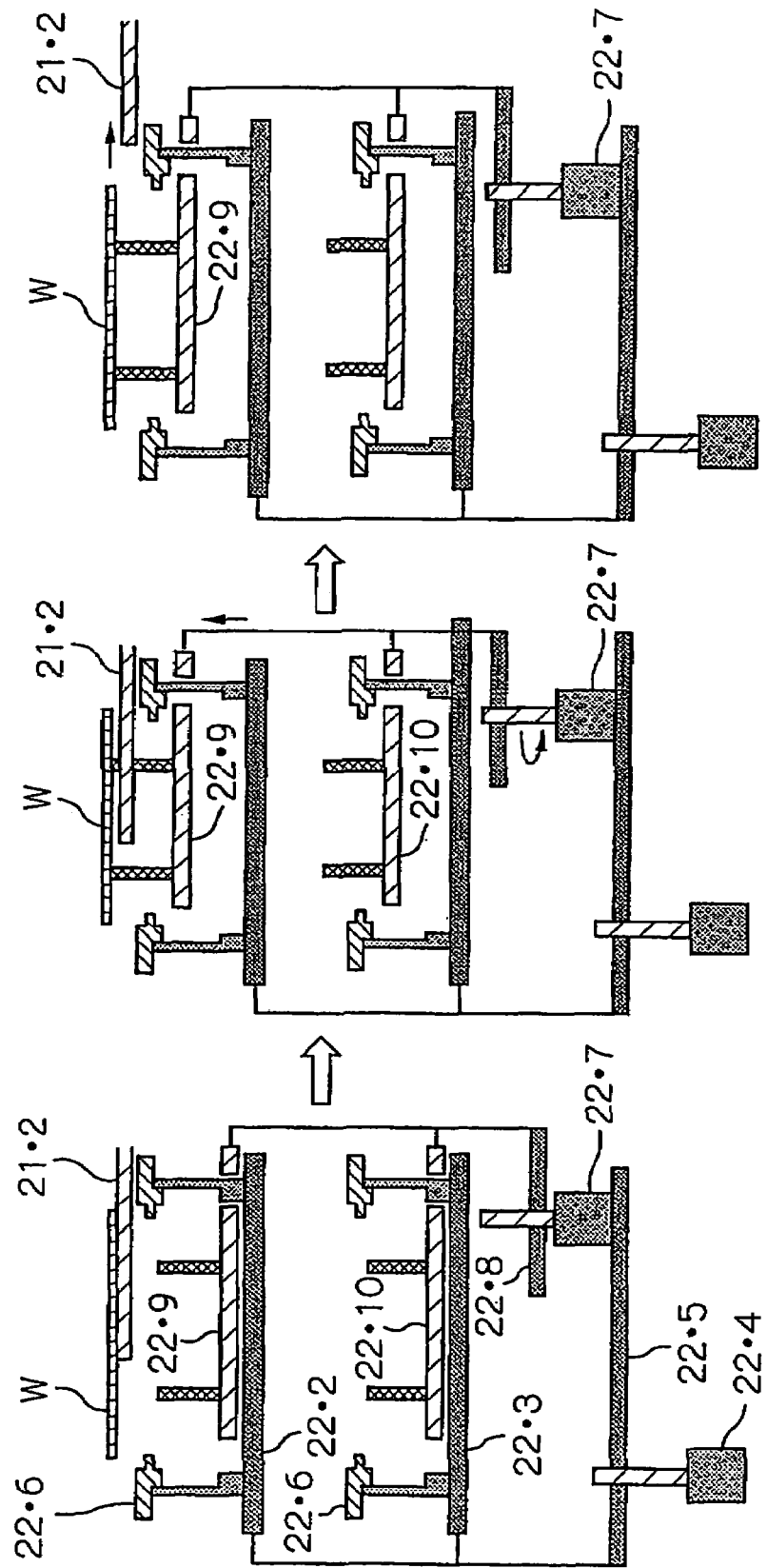
Figures 2, 31:
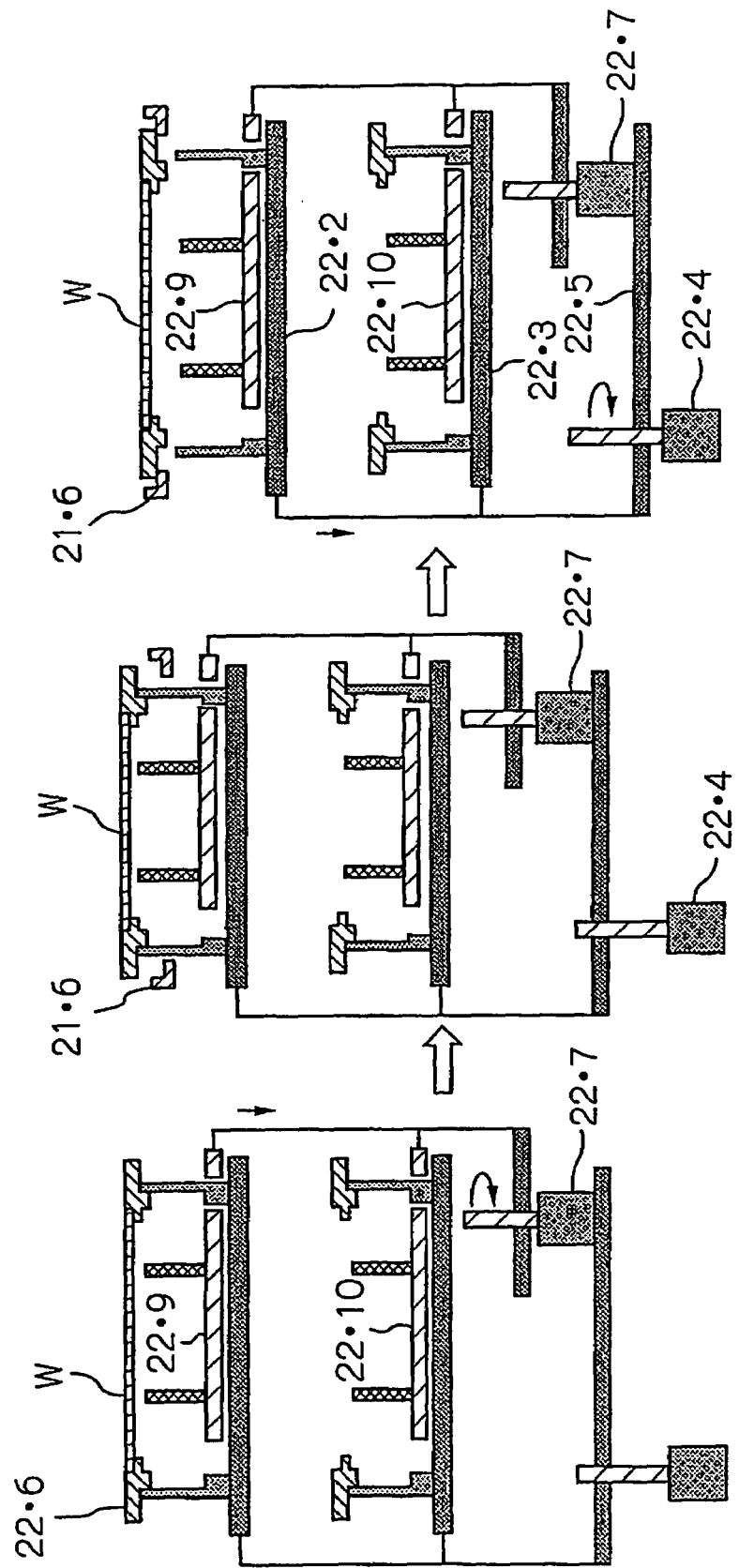

In the apparatus described in connection with FIG. 20, a procedure is taken to mount a correction ring on the electrostatic chuck, and position a wafer such that the wafer fits in the inner diameter of the correction ring. Therefore, in the inspection apparatus illustrated in FIG. 21, a procedure is taken to mount a correction ring on a wafer in the load lock chamber 22-1, integrally transfer the wafer mounted with the correction ring into the sample chamber 21-7, and place the wafer mounted with the correction ring on the electrostatic chuck on the stage. A feature for implementing the foregoing procedure may be an elevator mechanism for moving up and down an elevator to pass a wafer from the atmosphere transfer robot to the vacuum transfer robot, as shown in FIGS. 31-1, 31-2. The following description will be focused on a procedure of transferring a wafer using this mechanism.

As illustrated in FIG. 31-1(A), the elevator mechanism disposed in the load lock chamber has a plurality of stages of correction ring support shelves (two stages in the figure) arranged for movement in the vertical direction. An upper correction ring support shelf 22-2 and a lower correction ring support shelf 22-3 are fixed to a first base 22-5 which is moved up and down through rotations of a first motor 22-4. Thus, the rotation of the first motor 22-4 causes the first base 22-5 and the upper and lower correction ring support shelves 22-2, 22-3 to move up or down.

Carried on each correction ring support shelf are correction rings 22-6 each having an inner diameter suited to a particular size of a wafer. There are two types of correction rings 22-6 provided for 200-mm wafers and 300-mm wafers, respectively. These correction rings have the same outer diameter. Such use of correction rings having the same outer diameter results in compatibility, allowing correction rings for 200-mm wafers and for 300-mm wafers to be stored in a free combination in the load lock chamber. In other words, for a line on which 200-mm wafers and 300-mm wafers flow in mixture, the upper shelf is dedicated to correction rings for 300-mm wafers, while the lower shelf is dedicated to correction rings for 200-mm wafers, such that a test can be conducted for whichever wafer appears, thus supporting any wafer in a flexible manner. On the other hand, for a line on which wafers of the same size flow, the upper and lower shelves are dedicated to correction rings for 200-mm or 300-mm wafers, so that wafers on the upper and lower shelves can be alternately tested to improve the throughput.

A second motor 22-7 is carried on the first base 22-5, while a second base 22-8 is attached to the second motor 22-7 such that the second base 22-8 can be moved up and down. An upper wafer support shelf 22-9 and a lower wafer support shelf 122-10 are fixed on the second base 22-8. With this structure, the rotation of the second motor 22-7 causes the second base 22-8 and upper and lower wafer support shelves 22-9, 22-10 to integrally move up or down.

Bearing the foregoing in mind, a wafer W placed on the hand of the atmosphere transfer robot 21-2 is introduced into the load lock chamber 22-1, as illustrated in FIG. 31-1(A). Next, as illustrated in FIG. 31-1(B), the second motor 22-7 is rotated in a first direction, causing the wafer support shelves 22-9, 22-10 to move up. Then, a wafer W is placed on the upper wafer support shelf 22-9. In this way, the wafer W is moved from the atmospheric transfer robot 21-2 to the wafer support shelf 22-9. Subsequently, as illustrated in FIG. 31-1(C), the atmosphere transfer robot 21-2 is retracted, and the second motor 22-7 is rotated in the direction opposite to the first direction, as illustrated in FIG. 31-2(D), when the atmosphere transfer robot 21-2 has been retracted, causing the wafer support shelves 22-9, 22-10 to move down. In this way, the wafer W is placed on the upper correction ring 22-6.

Next, as illustrated in FIG. 31-2(E), the hand of the vacuum transfer robot 21-6 is introduced into the load lock chamber 22-1, and stopped below the correction ring 22-6. In this state, the first motor 22-4 is rotated to move down the first base 22-5, upper and lower correction ring support shelves 22-2, 22-3, second motor 22-7, and upper and lower wafer support shelves 22-9, 22-10, as illustrated in FIG. 31-2(F). In this way, the correction ring 21-6 and wafer W placed on the upper wafer support shelf 22-9 can be carried on the hand of the vacuum transfer robot 21-6, and introduced into the sample chamber 21-7.

The operation for bringing a wafer which has undergone a test in the sample chamber 21-7 back into the load lock chamber 21-4 is performed in a procedure reverse to the foregoing. A wafer carried on a wafer support shelf together with a correction ring by the vacuum transfer robot is transferred to a correction ring support shelf, next to the wafer support shelf, and finally on the atmosphere transfer robot. While the foregoing description has been made of the wafer passing operation on the upper shelf with reference to FIGS. 31-1 and 31-2, a similar operation can be accomplished as well on the lower shelf by adjusting the hands of the atmosphere transfer robot 21-2 and vacuum transfer robot 21-6 in height. By appropriately switching the heights for the hands of the atmosphere transfer robot 21-2 and vacuum transfer robot 21-6 in the foregoing manner, it is possible to alternate the introduction of an untested wafer from one shelf into the sample chamber and the removal of a tested wafer from the sample chamber to the other shelf.

Loader 60

The loader 60 (FIG. 12) comprises a robot-based first transfer unit 61 disposed in the housing 22 of the mini-environment device 20, and a robot-based second transfer unit 63 disposed in the second loading chamber 42.

The first transfer unit 61 has a multi-node arm 612 for rotation about an axis $O_1$—$O_1$ relative to a driver 611. While an arbitrary structure may be applied to the multi-node arm, this embodiment employs the multi-node arm 612 which has three parts attached for rotation relative to each other. A part of the arm 612 of the first transfer unit 61, i.e., a first part closest to the driver 611 is attached to a shaft 613 which can be rotated by a driving mechanism (not shown) in a general-purpose structure arranged in the driver 611. The arm 612 is rotatable about the axis $O_1$—$O_1$ by the shaft 613, and is telescopical in a radial direction relative to the axis $O_1$—$O_1$ as a whole through relative rotations among the parts. At the leading end of the third part furthest away from the shaft 613 of the arm 612, a chuck 616 is attached for chucking a wafer, such as a mechanical chuck in a general-purpose structure, an electrostatic chuck or the like. The driver is vertically movable by an elevating mechanism in a general-purpose structure.

In this first transfer unit 61, the arm 612 extends toward one of two cassettes c held in the cassette holder 10 in a direction M1 or M2 (FIG. 13), and a wafer W stored in the cassette c is carried on the arm, or is chucked by the chuck (not shown) attached at the leading end of the arm for removal. Subsequently, the arm is retracted (to the state illustrated in FIG. 13), and the arm is rotated to a position at which the arm can extend toward the pre-aligner 25 in a direction M3, and is stopped at this position. Then, the arm again extends to the pre-aligner 25 to transfer the wafer held by the arm thereto. After receiving the wafer from the pre-aligner 25 in a manner reverse to the foregoing, the arm is further rotated and stopped at a position at which the arm can extend toward the first loading chamber 41 (in a direction M4), where the wafer is passed to a wafer receiver 47 within the first loading chamber 41. It should be noted that when a wafer is mechanically chucked, the wafer should be chucked in a peripheral zone (in a range approximately 5 mm from the periphery). This is because the wafer is formed with devices (circuit wires) over the entire surface except for the peripheral zone, so that if the wafer were chucked at a portion inside the peripheral zone, some devices would be broken or defects would be produced.

The second transfer unit 63 is basically the same as the first transfer unit 61 in structure, and differs only in that the second transfer unit 63 transfers a wafer W between the wafer lack 47 and the carrying surface of the stage device 50.

The first and second transfer units 61, 63 transfer wafers from the cassette c held in the cassette holder onto the stage device 50 disposed in the working chamber 31 and vice versa while holding the wafer substantially in a horizontal posture. Then, the arms of the transfer units 61, 63 are moved up and down only when a cassette is extracted from the cassette c and loaded into the same, when a wafer is placed on the wafer lack and is extracted from the same, and when a wafer is placed on the stage device 50 and removed from the same. Therefore, the transfer units 61, 63 can smoothly move even a large wafer which may have a diameter of, for example, 30 cm.

Now, description will be made in order of the transfer of a wafer from the cassette c supported by the cassette holder 10 to the stage device 50 disposed in the working chamber 31 in the inspection system 1 having the configuration described above.

The cassette holder 10 for use in the inspection system 1 may have an appropriate structure either when cassettes are manually set or when cassettes are automatically set, as mentioned above. In this embodiment, as the cassette c is set on the up/down table 11, the up/down table 11 is moved down by the elevating mechanism 12 to bring the cassette c into alignment to the access port 225. As the cassette c is in alignment to the access port 225, a cover (not shown) disposed on the cassette c is opened, whereas a cylindrical cover is arranged between the cassette c and the access port 225 of the mini-environment device 20 to block the cassette c and mini-environment space 21 from the outside. When the mini-environment device 20 is equipped with a shutter for opening/closing the access port 225, the shutter is operated to open the access port 225.

On the other hand, the arm 612 of the first transfer unit 61 remains oriented in either the direction M1 or M2 (in the direction M1 in this description), and extends to receive one of wafers stored in the cassette c with its leading end as the access port 225 is opened.

Once the arm 612 has received a wafer, the arm 612 is retracted, and the shutter (if any) is operated to close the access port 225. Then, the arm 612 is rotated about the axial line $O_1$—$O_1$ so that it can extend in the direction M3. Next, the arm 612 extends to transfer the wafer carried on the leading end thereof or chucked by a chuck onto the pre-aligner 25 which determines a direction in which the wafer is rotated (direction about the center axis perpendicular to the surface of the wafer) within a predetermined range. Upon completion of the positioning, the first transfer unit 61 retracts the arm 612 after the wafer is received from the pre-aligner 25 to the leading end of the arm 612, and takes a posture in which the arm 612 can be extended in the direction M4. Then, the door 272 of the shutter 27 is moved to open the access ports 226, 436, permitting the arm 612 to place the wafer on the upper shelf or lower shelf of the wafer rack 47 within the first loading chamber 41. It should be noted that before the shutter 27 opens the access ports to pass the wafer to the wafer rack 47, the opening 435 formed through the partition 434 is hermetically closed by the door 461 of the shutter 46.

In the wafer transfer process by the first transfer unit 61, clean air flows in a laminar state (as a down flow) from the gas supply unit 231 disposed in the housing body 22 of the mini-environment device 20, for preventing dust from sticking to the upper surface of the wafer during the transfer. Part of air around the transfer unit (in this embodiment, approximately 20% of the air supplied from the gas supply unit 231, which is mainly contaminated) is aspired from the suction duct 241 of the discharger 24 for emission out of the housing body 22. The remaining air is recovered through the recovery duct 232 arranged on the bottom of the housing body 22, and again returned to the gas supply unit 231.

As a wafer is placed on the wafer rack 47 within the first loading chamber 41 of the loader housing 40 by the first transfer unit 61, the shutter 27 is closed to hermetically close the loading chamber 41. Then, the loading chamber 41 is brought into a vacuum atmosphere by expelling the air within the loading chamber 41, filling an inert gas in the loading chamber 41, and then discharging the inert gas. The vacuum atmosphere in the loading chamber 41 may have a low degree of vacuum. As the degree of vacuum has reached a certain level in the loading chamber 41, the shutter 46 is operated to open the access port 434, which has been hermetically closed by the door 461, and the arm 632 of the second transfer unit 63 extends to receive one wafer from the wafer receiver 47 with the chuck 616 at the leading end thereof (placed on the leading end or chucked by a chuck attached to the leading end). As the wafer has been received, the arm 632 is retracted, and the shutter 46 is again operated to close the access port 435 with the door 461. It should be noted that before the shutter 36 opens the access port 435, the arm 632 has previously taken a posture in which it can extend toward the wafer rack 47 in a direction N1. Also, as described above, before the shutter 46 opens the access port 435, the shutter 45 closes the access ports 437, 325 with the door 452 to block communications between the second loading chamber 42 and the working chamber 31, and the second loading chamber 42 is evacuated.

As the shutter 46 closes the access port 435, the second loading chamber 42 is again evacuated to a degree of vacuum higher than that of the first loading chamber 41. In the meantime, the arm 612 of the second transfer unit 61 is rotated to a position from which the arm 612 can extend toward the stage device 50 within the working chamber 31. On the other hand, in the stage device 50 within the working chamber 31, the Y-table 52 is moved upward, as viewed in FIG. 13, to a position at which the center line $X_0$—$X_0$ of the X-table 53 substantially matches an X-axis line $X_1$—$X_1$ which passes the axis of rotation $O_2$—$O_2$ of the second transfer unit 63. Also, the X-table 53 has moved to a position close to the leftmost position, as viewed in FIG. 2, and is waiting at this position. When the degree of vacuum in the second loading chamber 42 is increased to a level substantially identical to that of the working chamber 31, the door 452 of the shutter 45 is moved to open the access ports 437, 325, and the arm 612 extends so that the leading end of the arm, which holds a wafer, approaches the stage device 50 within the working chamber 31. Then, the wafer W is placed on the carrying surface 551 of the stage device 50. Once the wafer W has been placed on the stage device 50, the arm 612 is retracted, and the shutter 45 closes the access ports 437, 325.

The foregoing description has been made of a sequence of operations until a wafer W in the cassette c is transferred to the working chamber 31 and placed on the carrying surface 551 of the stage device 50. For returning a wafer W which has undergone a test from the stage device 50 to the cassette c, operations reverse to the foregoing are performed. Also, since a plurality of wafers are placed on the wafer rack 47, the first transfer unit 62 can transfer a wafer between the cassette c and the wafer rack 47 while the second transfer unit 63 is transferring a wafer between the wafer rack 47 and the stage device 50. Consequently, operations associated with the test can be efficiently conducted.

Opto-Electro System 70

The opto-electro system 70 (FIG. 12) is a system for producing images of a sample, and as described above, can employ the electron beam apparatus according to the present invention described in connection with FIGS. 1–9.

Pre-Charge Unit 81

The pre-charge unit 81 is disposed in close proximity to the lens column 71 of the opto-electro system 70 within the working chamber 31, as previously shown in FIG. 12. Since the inspection system 1 of the present invention irradiates a wafer with electron beams for scanning to test a device pattern and the like formed on the surface of the wafer, the wafer can be charged on the surface depending on conditions such as the material of the wafer, energy of irradiated electron beams, and the like. Further, the wafer surface may include a region which is more charged and a region which is less charged. In addition, while information on secondary electrons or the like generated by irradiation of electron beams is used for analyzing the wafer surface, possible variations in the amount of charge on the wafer surface may cause the information on the secondary electrons to include variations as well, thereby failing to provide accurate images. To prevent such variations in charge, the pre-charge unit 81 is provided in this embodiment. The pre-charge unit 81 includes a charged particle irradiating unit 811 which irradiates charged particles to a wafer before primary electron beams are emitted for testing, thereby eliminating variations in charge. How the wafer surface is charged can be detected by previously forming an image of the wafer surface using the opto-electro system 70, and evaluating the image. Then, the irradiation of charged particles from the charged particle irradiating unit 811 is controlled based on the detected charging state. The pre-charge unit 81 may irradiate blurred primary electron beams.

Alignment Control Unit 87

The alignment control unit 87 aligns a wafer W to the opto-electro system 70 using the stage device 50. The alignment control unit 87 is configured to control a low magnification alignment (alignment with a lower magnification than the opto-electro system 70) which is a rough alignment of a wafer through a wide field observation using the optical microscope 871 (FIGS. 12 and 32); a high magnification alignment for a wafer using the opto-electro system 70; focus adjustment; setting of an area under inspection; pattern alignment; and the like. It should be noted that a wafer is tested at a low magnification as mentioned above because for automatically inspecting patterns on a wafer, an alignment mark must be readily detected by electron beams when the wafer is aligned by observing the patterns on the wafer in a narrow field of view using electron beams.

The optical microscope 871 is installed within the main housing 30, but may be movably disposed within the main housing 30. A light source (not shown) for operating the optical microscope 871 is also disposed within the main housing 300. Further, the opto-electro system involved in observations at high magnification shares components (primary optical system 72 and secondary optical system 74) of the opto-electro system 70.

Figure 32:
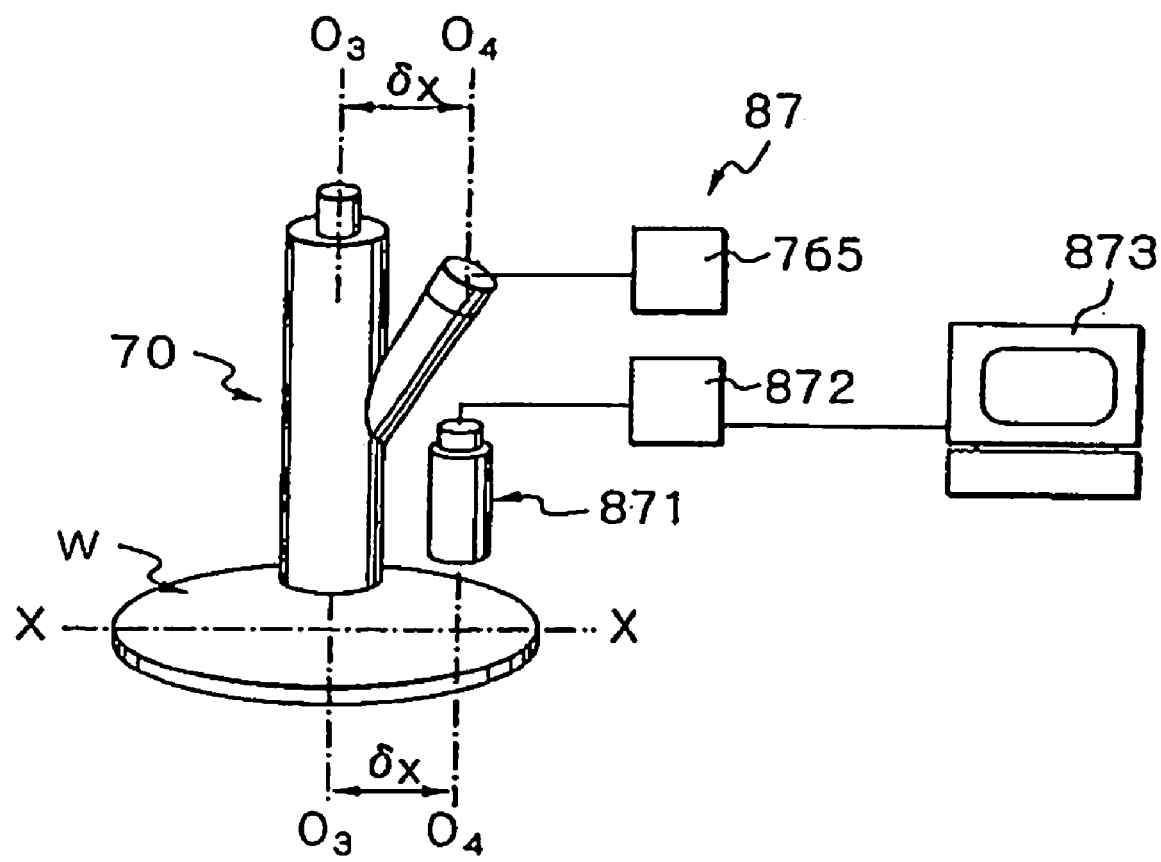
FIG. 32 is an explanatory diagram generally illustrating a wafer alignment controller which can be applied to an opto-electro system of the inspection system illustrated in FIG. 12.

FIG. 32 generally illustrates the configuration of the alignment control unit 87. For observing a site under observation on a wafer W at a low magnification, the site under observation on the wafer W is moved into the field of view of the optical microscope 871 by moving the X-stage or Y-stage of the stage device 50. The wafer W is viewed in a wide field of view using the optical microscope 871, and the site under observation on the wafer W is displayed on a monitor 873 through a CCD 872 to roughly determine where the site under observation is found. In this event, the magnification of the optical microscope 871 may be gradually changed from a low magnification to a high magnification.

Next, the stage device 50 is moved by a distance corresponding to a spacing δx between the optical axis of the opto-electro system 70 and the optical axis of the optical microscope 871, thereby moving the site under observation on the wafer W, which has been previously determined using the optical microscope 871, into the field of view of the opto-electro system 70. In this event, since the distance δx between the axial line $O_3$—$O_3$ of the opto-electro system 70 and the optical axis $O_4$—$O_4$ of the optical microscope 871 has been previously known (while both are shifted only in the X-direction in this embodiment, they may be shifted in the Y-direction), the site under observation can be moved to a viewing position of the opto-electro system 70 if the wafer W is moved by the distance δx. After the site under observation has been moved to the viewing position of the opto-electro system 70, the site under observation is imaged at a high magnification by the opto-electro system, and the resulting image is stored or displayed on a monitor 873.

After the site under observation of the wafer is displayed at a high magnification by the opto-electro system as described above, a displacement of the wafer in the rotating direction relative to the center of rotation of the rotary table 54 of the stage device 50, i.e., a shift δθ of the wafer in the rotating direction relative to the optical axis $O_3$—$O_3$ of the opto-electro system is detected by a known method, and a displacement of a predetermined pattern is detected in the X-axis and Y-axis directions relative to the opto-electro system 70. Then, the operation of the stage device 50 is controlled to align the wafer based on the detected values, data on a test mark separately attached on the wafer, or data related to the shapes of the patterns on the wafer.

Next, an alignment procedure will be described in greater detail.

Figure 33:
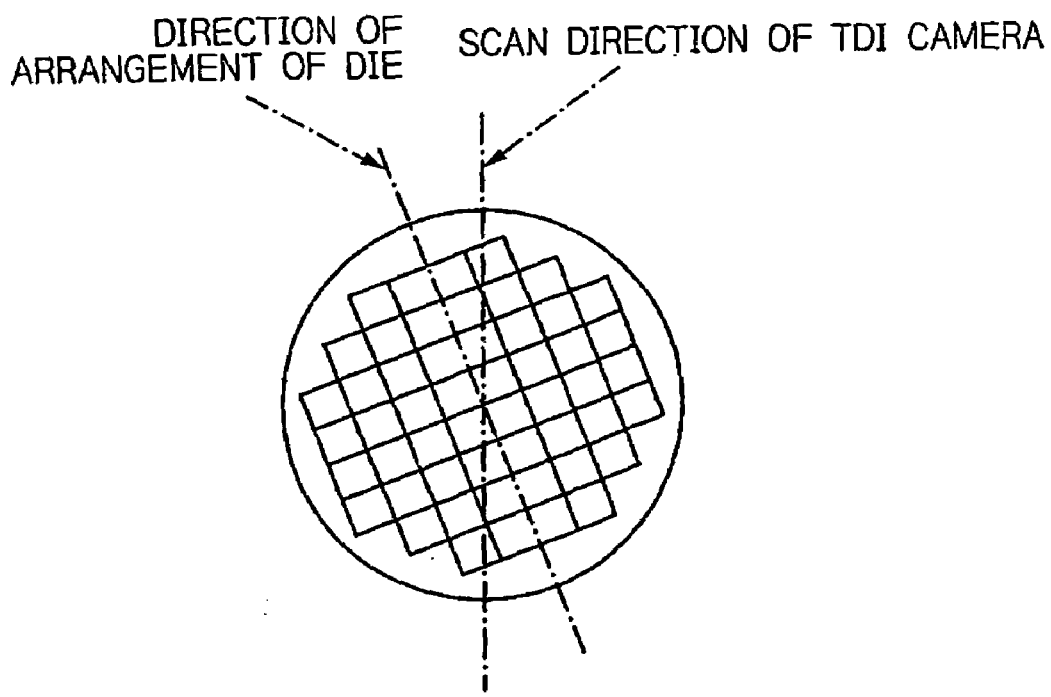
FIG. 33 is a diagram for explaining why a wafer must be in alignment.
Figure 34:
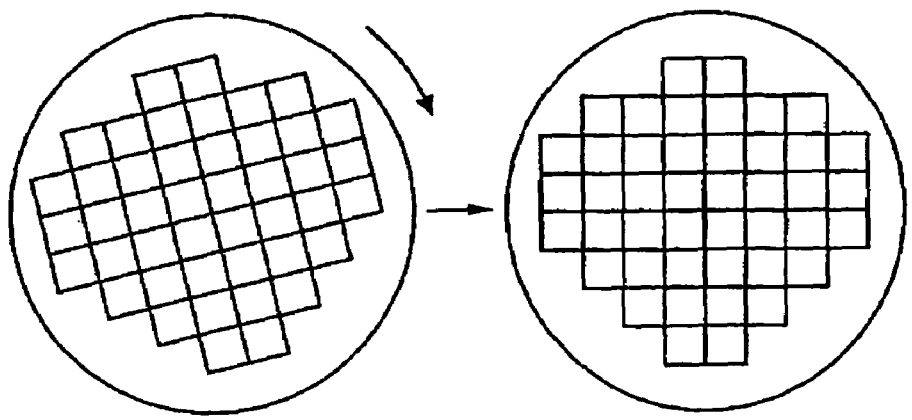
FIG. 34 is a diagram for explaining how a wafer is brought into alignment.

Dies on a wafer loaded on the stage are arranged in a direction which is not necessarily coincident with a scanning direction of a TDI camera (see FIG. 33). To make them coincident, the wafer must be rotated on the θ stage through an operation called "alignment" (FIG. 34). An alignment recepi saves alignment execution conditions after a wafer is loaded on the stage.

In addition, a die map (FIG. 35) is also created for indicating the arrangement of dies upon execution of the alignment, and a die map recipe including the size of dies, the position of an origin die (which serves as the origin for indicating the location of a particular die), and the like is stored.

The alignment (positioning) procedure involves first making a rough alignment at a low magnification with an optical microscope, making a detailed alignment at a high magnification with the optical microscope, and finally making a fine alignment using an EB image.

A. Imaging at Low Magnification using Optical Microscope:

(1) Specify First, Second, Third Searched Dies and Template (1-1) Specify First Searched Die and Template:

The user moves the stage such that the lower left corner of a die located in a lower region of a wafer is positioned near the center of the camera, and captures a template image for pattern matching after determining the position. This die is referenced for the positioning, and the coordinate at the lower left corner are the coordinate of a characteristic point. From then on, this template image is used for pattern matching to measure the coordinate of the precise location of an arbitrary die on the wafer. An image selected for the template image must be a unique pattern within a search region.

While the lower left corner is defined to be the position at which the template image for pattern matching is captured in this embodiment, the characteristic point is not limited to the lower left corner, but may be an arbitrary location within a die. Generally, however, it is easier to use a corner is to identify the coordinate than a point located within a die or on a side of the die, so that one of the four corners is preferably selected. Likewise, in this embodiment, a template image for pattern matching is captured for a die located in a lower region of a wafer, but it goes without saying that an arbitrary die may be selected to facilitate the alignment.

(1-2) Specify Second Searched Die:

A die next to the first searched die on the right side is chosen to be a second searched die, and the user moves the stage such that the lower left corner of the second searched die is positioned near the center of the camera. After determining the position, the pattern matching is automatically performed using the template image captured in the aforementioned section (1-1) to acquire precise coordinate values for a pattern of the second searched die which is coincident with the template image specified in the first searched die.

While the die adjacent to the first searched die on the right side is chosen to be the second searched die for purposes of description in this embodiment, the second searched die of the present invention is not limited to this die, as a matter of course. In essence, the selection may be made for a point at which a positional relationship of dies in the row direction can be more precisely found from the reference point at which precise coordinate has been found for the position of the characteristic point. Therefore, a die adjacent to the first searched die on the left side may be chosen to be the second searched die.

(1-3) Specify Third Searched Die:

A die immediately above the second searched die is chosen to be a third searched die, and the user moves the stage such that the lower left corner of the third searched die is positioned near the center of the camera. After determining the position, the pattern matching is automatically performed using the template image captured in the aforementioned step (1-1) to acquire precise coordinates for a pattern of the third searched die which are coincident with the template image specified in the first searched die.

While the die immediately above the first searched die on the right side is chosen to be the third searched die for purposes of description in this embodiment, the third searched die of the present invention is not limited to this die, as a matter of course. In essence, the selection may be made such that a positional relationship including a distance to the coordinate of a particular point of a die in the column direction can be found, with reference to the die at which precise coordinate has been found for the position of the characteristic point. Therefore, a die immediately above the second searched die may be chosen to be the third searched die.

(2) Y-Direction Low Magnification Pattern Matching using Optical Microscope (2-1) Moving amounts (dX, dY) to the immediately above die are calculated from the relationship between the pattern match coordinate (X2, Y2) of the second searched die and the pattern match coordinate (X3, Y3) of the third searched die:

$$dX = X3 - X2$$

$$dY = Y3 - Y2$$

(2-2) The stage is moved to coordinate (XN, YN) at which a pattern of a die immediately above the first searched die will (be expected to) exist using the calculated moving amount (dX, dY).

$$XN = X1 + dX$$

$$YN = Y1 + dY$$

In the above, (X1, Y1) are the coordinate values of a pattern of the first searched die.

(2-3) Precise coordinate values (XN, YN) of a pattern currently under observation are captured by imaging at a low magnification with the optical microscope after the stage has been moved and executing the pattern matching using the template image, and one is set to the initial value for the number of detected dies (DN).

(2-4) Moving amount value (dX, dY) are calculated from the coordinate (X1, Y1) of the pattern of the first searched die to the coordinate (XN, YN) of the pattern which is currently being imaged.

$$dX = XN - X1$$

$$dY = YN - Y1$$

(2-5) The stage is moved from the first searched die by moving amounts (2*dX, 2*dY) twice as much as the calculated moving amounts (dX, dY).

(2-6) The precise coordinate (XN, YN) of the pattern currently under observation are updated by imaging at a low magnification with the optical microscope after the stage has been moved, and executing the pattern matching using the template image, and the number of detected dies is increased by a factor of two. See FIG. 36 for this operation.

(2-7) Steps (2-4) to (2-6) are executed in repetition toward the upward direction on the wafer until a previously specified Y-coordinate value is exceeded.

While this embodiment has been described in connection with an exemplary scenario in which a double moving amount is repeated in order to increase the accuracy, reduce the number of times of processing (number of repetitions), and reduce the processing time, a high integer magnification of more than two, such as three times or four times may be used for execution on the condition that no problem occurs in accuracy and the processing time is preferably further reduced. Conversely, the movement may be repeated with a fixed moving amount for further increasing the accuracy, on the condition that no problem occurs. In either case, it goes without saying that this should be reflected to the number of detected dies.

Figure 37:
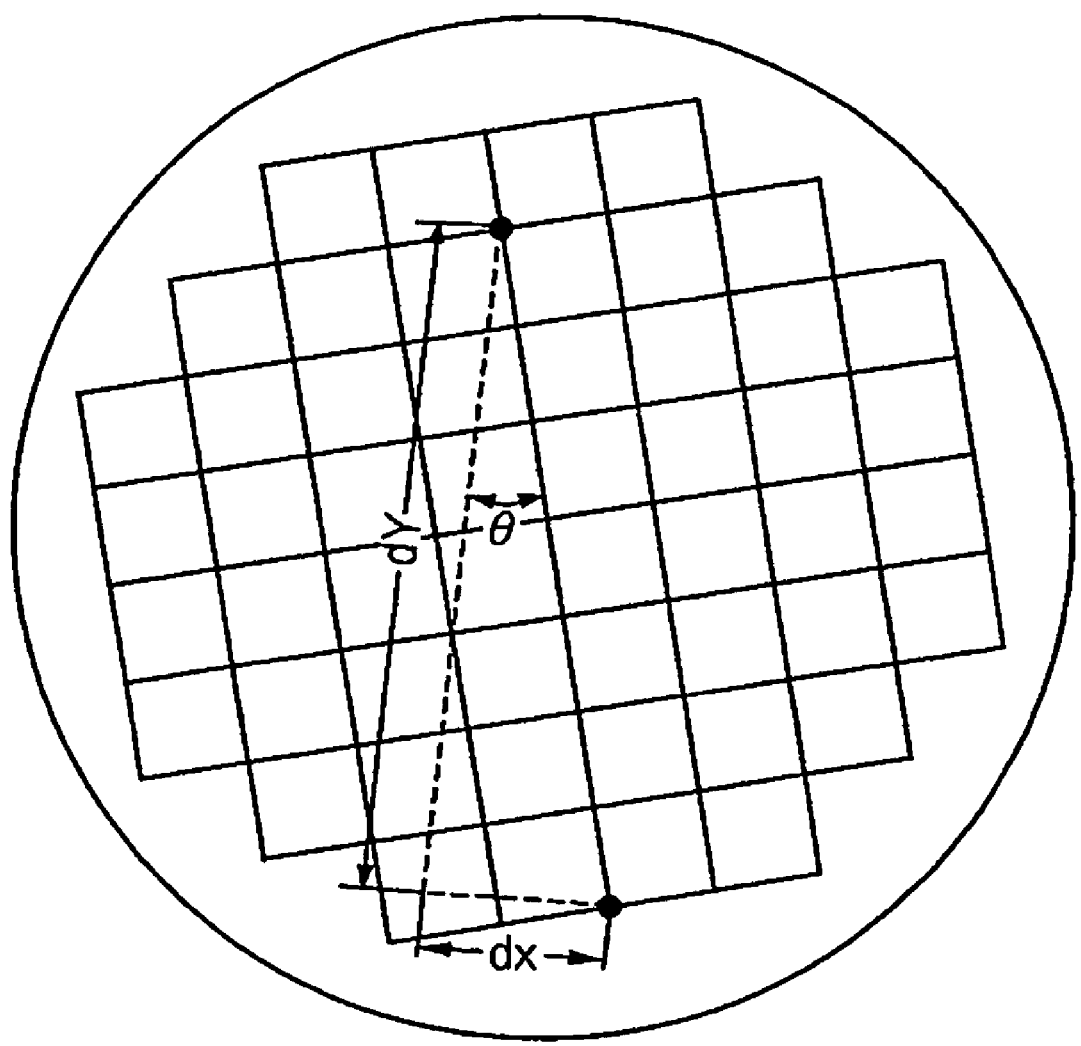
FIG. 37 is a diagram for explaining an amount of rotation and a size in the Y-direction of the wafer in the wafer alignment procedure.

(3) θ Rotation at Low Magnification of Optical Microscope (3-1) A rotating amount (θ) and a Y-direction die size (YD) are calculated using the moving amount from the pattern coordinate (X1, Y1) of the first searched die to the precise coordinate (XN, YN) of the pattern of the finally searched die, and the number (DN) of dies so far detected (see FIG. 37).

$$dX = XN - X1$$

$$dY = YN - Y1$$

$$\theta = \tan^{-1}(dX/dY)$$

$$YD = ((dX)^2 + (dY)^2)^{1/2}/DN$$

(3-2) The θ Stage is Rotated by the Calculated Rotating Amount (θ).

B. Imaging at High Magnification using Optical Microscope:

(1) A procedure similar to (1) of the imaging at a low magnification is executed at a high magnification using the optical microscope.

(2) A procedure similar to (2) of the imaging at a low magnification is executed at a high magnification using the optical microscope.

(3) A procedure similar to (3) of the imaging at a low magnification is executed using the optical microscope.

(4) Check Tolerance after Optical Microscope High Magnification □ Rotation (4-1) Specify First Searched Die and Template for Imaging at High Magnification with Optical Microscope The coordinate (X'1, Y'1) of the first searched die after the rotation is calculated from the coordinate (X1, Y1) before the rotation and the rotating amount (θ). The stage is moved to the coordinate (X'1, Y'1). After determining the position, A template image is captured for pattern matching.

$$X'1 = x_1 * \cos\theta - y_1 * \sin\theta$$

$$Y'1 = x_1 * \sin\theta + y_1 * \cos\theta$$

(4-2) Pattern Matching in Y-Direction at High Magnification with Optical Microscope The stage is moved in the Y-direction by dY from the coordinate (X'1, Y'1) of the first searched die after the rotation, and the pattern matching is executed to acquire precise coordinate (XN, YN) of the pattern currently under observation.

(4-3) From Coordinates (X'1, Y'1) of First Searched Die after Rotation to Coordinate of Pattern Currently under Imaging Moving amounts (dX, dY) to the coordinate (XN, YN) is calculated.

$$dX = XN - X'1$$

$$dY = YN - Y'1$$

(4-4) The stage is moved from the first searched die by moving amounts (2*dX, 2*dY) twice as much as the calculated moving amounts (dX, dY).

(4-5) The precise coordinate (XN, YN) of the pattern currently under observation is updated by imaging at a low magnification with the optical microscope after the stage has been moved, and executing the pattern matching using the template image.

(4-6) Steps (4-3) to (4-5) are executed in repetition in the upward direction on the wafer until a previously specified Y-coordinate value is exceeded.

(4-7) Calculate Rotating Amount of θ:

The rotating amount (θ) is calculated using a moving amount from the coordinate (X'1, Y'1) of the first searched die after the rotation to the precise coordinate (XN, YN) of a pattern of a finally searched die.

$$dX = XN - X1$$

$$dY = YN - Y1$$

$$\theta = \tan^{-1}(dX/dY)$$

(4-8) Optical Microscope High Magnification θ Tolerance Check:

Confirmation is made as to whether the rotating amount (θ) calculated in (4-7) falls within a predefined value. If it does not, steps (4-1) to (4-8) are executed again after the θ stage is rotated using the calculated rotating amount (θ). However, when the rotating amount (θ) does not fall within the tolerance even after repeating steps (4-1) to (4-8) a predefined number of times, the processing is aborted, and it is determined that an error has occurred.

C. Alignment Using EB Image (1) Specify Y Search First Die and EB Template

A procedure similar to (1) of the imaging at a high magnification with the optical microscope is executed using an EB image.

(2) EB Y-Direction Pattern Matching

A procedure similar to (2) of the imaging at a high magnification with the optical microscope is executed using an EB image.

(3) EB θ Rotation

A procedure similar to (3) of the imaging at a high magnification with the optical microscope is executed using an EB image.

(4) EB Tolerance Check after Rotation of θ

A procedure similar to (4) of the imaging at a high magnification with the optical microscope is executed using an EB image.

(5) Steps (1) to (4) are executed using an EB image at a high magnification as required.

(6) An approximate value for the die size (XD) in the X-direction is calculated from the coordinate (X1, Y1) of the first searched die and the coordinate (X2, Y2) of the second searched die.

$$dX = X2 - X1$$

$$dY = Y2 - Y1$$

$$XD = ((dX)^2 + (dY)^2)^{1/2}$$

D. Creation of Die Map Recipe (1) Specify X-Search First Die and EB Template

The user moves the stage such that the lower left corner of the die located at the left end of the wafer is positioned near the center of a TDI camera, and acquires a template image for pattern matching after determining the position. Selected for this template image should be an image which is a unique pattern within a search region.

(2) EB X-Direction Pattern Matching (2-1) The stage is moved to the coordinate (X1+XD, Y1) at which a pattern of a die on the right side of the first searched die in the X-direction will (be expected to) exist, using an approximate value (XD) of the die size in the X-direction.

(2-2) After the stage is moved, an EB image is captured by the TDI camera. Precise coordinate (XN, YN) of a pattern currently under observation are acquired by executing the pattern matching using the template image, and one is set to an initial value for the number of detected dies (DN).

(2-3) Moving amounts (dX, dY) are calculated from the coordinate (X1, Y1) of the pattern on the X-search first die to the coordinate (XN, YN) of the pattern which is currently being imaged.

$$dX = XN - X1$$

$$dY = YN - Y1$$

(2-4) The stage is moved from the first searched die in the X-direction by moving amounts (2*dX, 2*dY) which is twice as much as the calculated moving amounts (dX, dY).

(2-5) The precise coordinate (XN, YN) of the pattern currently under observation is updated by capturing an EB image with the TDI camera after the stage has been moved, and executing the pattern matching using the template image, and the number of detected dies is increased by a factor of two.

(2-6) Steps (2-3) to (2-5) are repeatedly executed in the right direction on the wafer until a previously specified X-coordinate value is exceeded.

(3) Calculation of X-Direction Slope

A stage straight-going error (F) and X-direction die size (XD) are calculated using the moving amount from the coordinate (X1, Y1) of the pattern on the first searched die in the X-direction to the precise coordinate value (XN, YN) of the pattern on the finally searched die, and the number (DN) of dies so far detected.

$$dX = XN - X1$$

$$dY = YN - Y1$$

$$\Phi = \tan^{-1}(dX/dY)$$

$$XD = ((dX)^2 + (dY)^2)^{1/2}/DN$$

(4) Creation of Die Map

The X-direction die size (XD) thus calculated is combined with a Y-direction die size (YD) found during the calculation of the rotating amount (θ) to create a die map (ideal die arrangement information). The die map permits an ideal arrangement for dies to be found. On the other hand, any die on the substrate is affected, for example, by mechanical errors of the stage (errors in parts such as guides, and errors in assembly), errors of the interferometer (for example, due to the assembly of mirrors and the like), distorted images due to charge-up, so that all dies cannot be observed for an ideal arrangement, but the test should be conducted while finding errors between the actual locations of dies and an ideal arrangement on the die map, and automatically correcting the errors in consideration thereof.

E. Focus Recipe Creation Procedure

Figure 38:
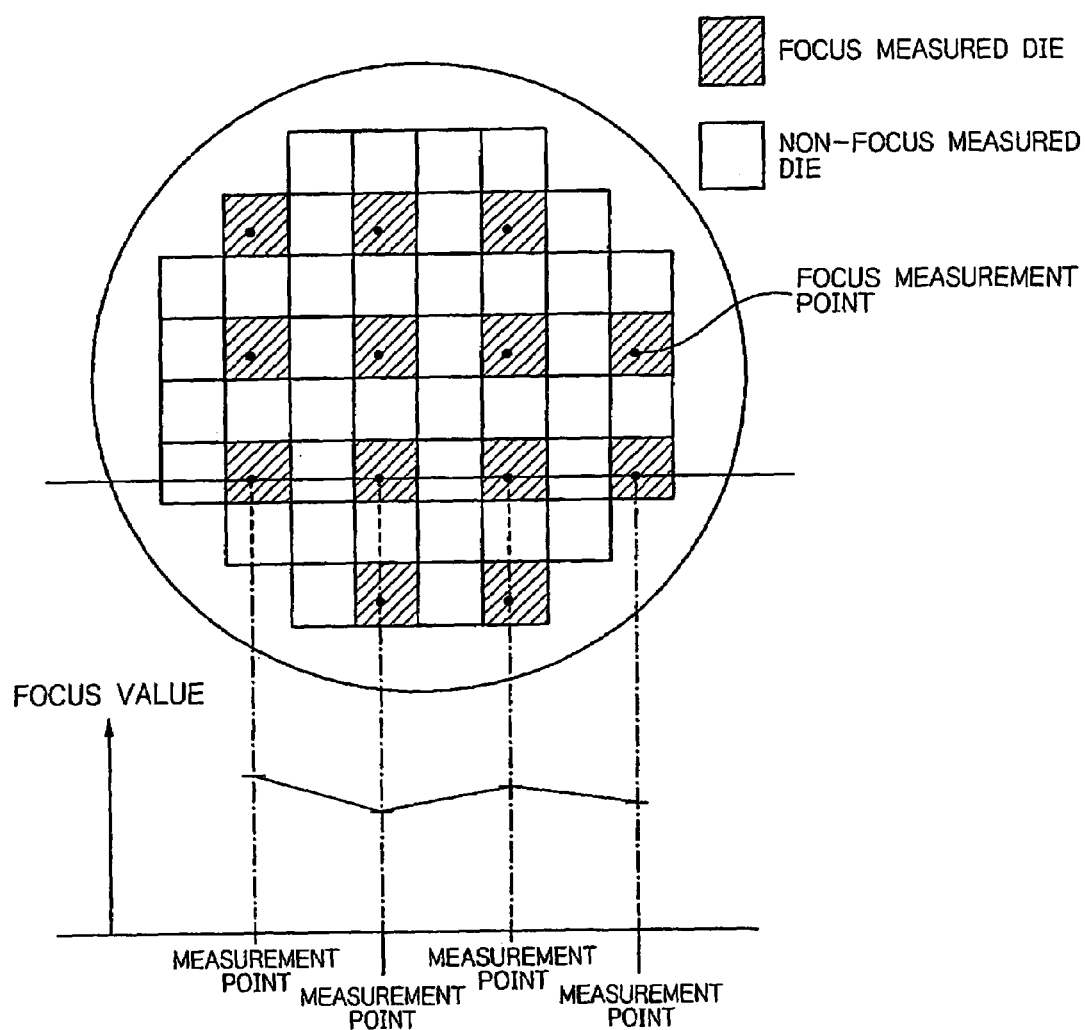
FIG. 38 is a diagram for explaining an interpolation of focus values during the creation of a focus prescription or recipe in the wafer alignment procedure.

Next, description will be made of a procedure of creating a focus recipe. The focus recipe stores information on an optimal focus position at a position of a mark on a flat surface of a sample such as a substrate, and information on a variety of conditions related to the focus position in a predetermined format such as a table. On a focus map recipe, the focus condition is set only for specified locations on a wafer, and focus values between the specified locations are linearly interpolated (see FIG. 38). The focus recipe creation procedure is as follows.

(1) A die subjected to a focus measurement is selected from the die map.

(2) A focus measurement point is set within a die.

(3) The stage is moved to each point at which the focus value (CL12 voltage) is manually adjusted based on the image and contrast value.

Figure 39:
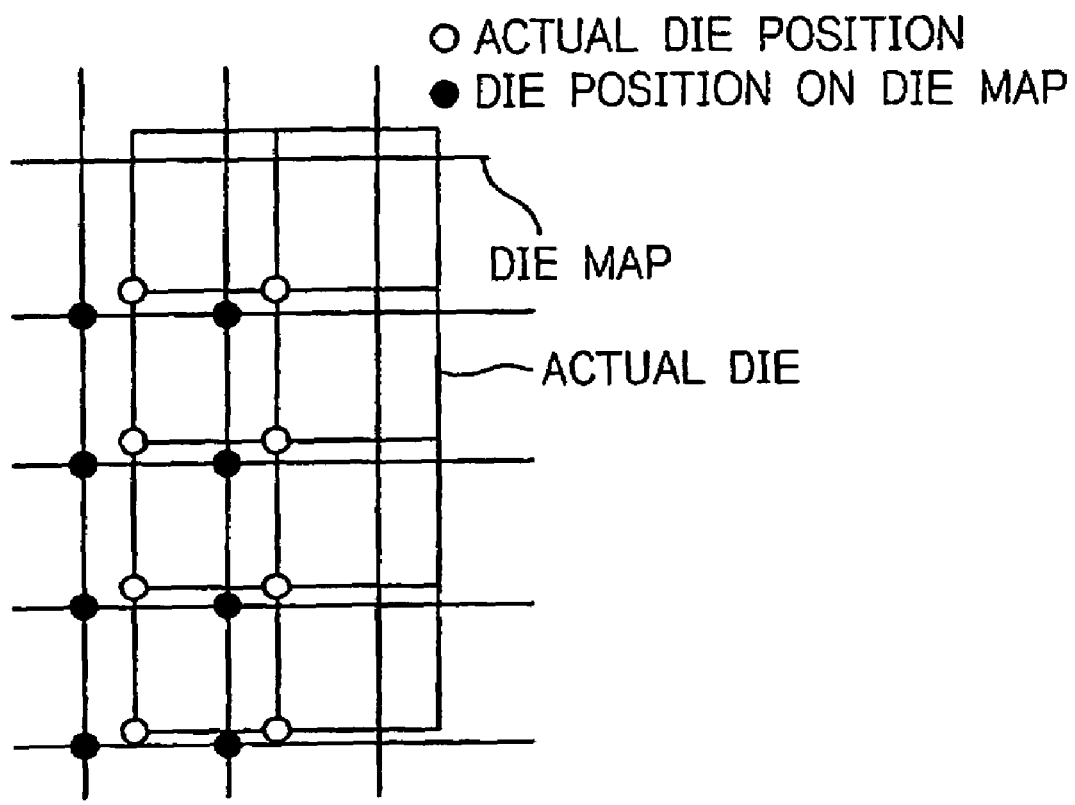
FIG. 39 is a diagram for explaining an error which can occur in the wafer alignment procedure.

The die map created through the alignment processing shows ideal positional information calculated from the coordinate of the dies at both ends of a wafer, and errors can occur due to a variety of factors between the locations of dies on the die map and actual locations of dies (see FIG. 39). A procedure for creating a parameter for absorbing the errors is called "fine alignment," and a fine alignment recipe error information of the die map (ideal die arrangement information) and actual locations of dies. The information set herein is used during a defect detection. In the fine alignment recipe, errors are measured only for those dies which are specified on the die map, and errors between the specified dies are linearly interpolated.

F. Fine Alignment Procedure (1) Dies subjected to error measurement for fine alignment are specified from the die map.
(2) A reference die is selected from the die subjected to error measurement, and the location of this die is defined to be a point at which there is no error with respect to the die map.
(3) The lower left corner of the reference die is imaged by the TDI camera to capture a template image for pattern matching (however, a unique pattern within a search region is selected as the template image).
(4) Lower left (on the die map) coordinate (X0, Y0) of a nearby die subjected to error measurement are acquired, and the stage is moved thereto. After the movement, the die is imaged by the TDI camera, and precise coordinate (X, Y) is acquired by executing the pattern matching using the template image captured in Step (3).
(5) Errors between the coordinate (X, Y) acquired through the pattern matching and coordinate (X0, Y0) on the die map are saved.
(6) Steps (4)–(5) are executed for all the dies subjected to error measurement.

A further detailed description will be made on a defect detecting apparatus for processing data generated by the opto-electro system 70 to acquire image data and for detecting defects on a semiconductor wafer based on the acquired image data in accordance with the present invention.

Generally, the inspection apparatus using electron beams, i.e., the opto-electro system 70 is expensive and presents a lower throughput than other process apparatuses. For this reason, the inspection apparatus is currently utilized after important processes which are thought to have the most need of the test (for example, etching, deposition, CMP (chemical mechanical polishing) planarization, and the like) or in part of a wiring process which involves finer wires, i.e., one or two steps of the wiring process, in a gate wiring step in the pre-process, and the like. In particular, it is important to find defective shapes and electric defects of wires having a design rule of 100 nm or less, via holes having diameters of 100 nm or less, and the like, and to feed the found defects back to associated processes.

As described above, a wafer to be tested is transferred by the atmosphere transfer system and vacuum transfer system, aligned on the highly precise stage device (X-Y stage) 50, and then fixed by an electrostatic chucking mechanism or the like. Then, in a defect inspection process, an optical microscope is used to confirm the location of each die and detect the height of each location, as required, and such data is stored. The optical microscope is also used to capture an optical microscopic image of desired sites such as defects and to compare electron beam images. Next, conditions are set for the opto-electro system, and an electron beam image is used to modify the information set by the optical microscope to improve accuracy.

Next, information on recipes is entered to the apparatus depending on the type of wafer (after which process, whether the wafer size is 200 mm or 300 mm, and the like). Subsequently, after specifying a inspection place, setting the opto-electro system, setting inspection conditions, and the like, a defect test is normally conducted in real time while images are captured. A comparison of cells to one another, a comparison between dies, and the like are performed by a high speed information processing system which has associated algorithms installed therein, and the results are output to a CRT or the like, and stored in a memory, as required.

Figure 40:
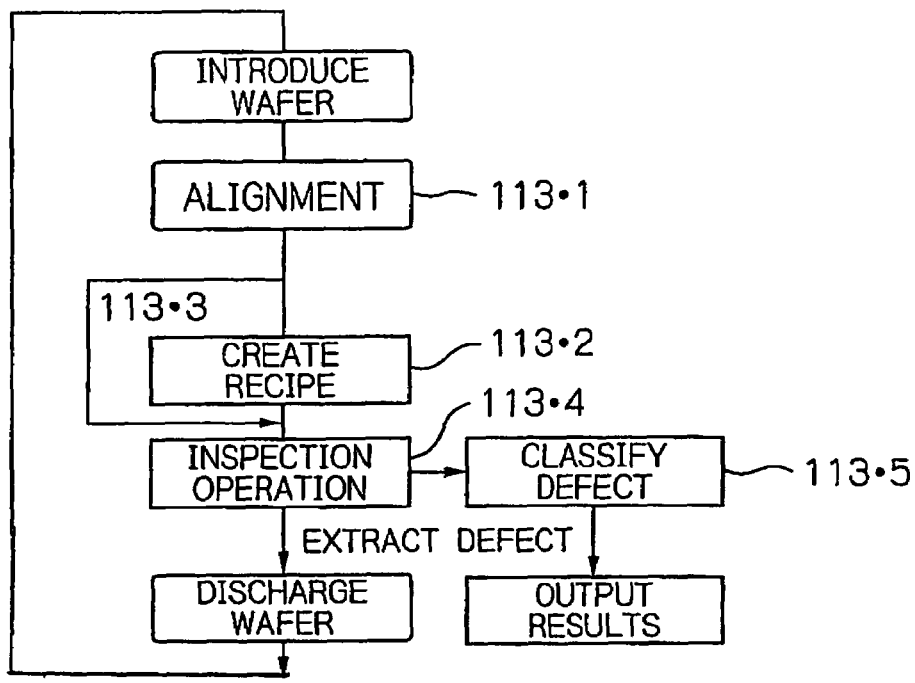
FIG. 40 is a diagram for explaining a basic flow of a semiconductor device inspection procedure.

FIG. 40 illustrates a basic flow of the defect test. First, after transfer of wafers including an alignment operation 113-1, the recipes are created for setting conditions related to the test, and the like (113-2). While at least one type of recipe is needed for each wafer under inspection, a plurality of recipes may be created for a single wafer under inspection in order to support a plurality of inspection conditions. Also, when there is a plurality of wafers having the same pattern, the plurality of wafers may be tested in accordance with a single recipe. A path 113-3 in FIG. 40 indicates that when a test is conducted using recipes created in the past, the creation of recipes is not required immediately before the inspection operation.

In FIG. 40, the inspection operation 113-4 involves a test on a wafer in accordance with the conditions described in the recipe and a sequence. A defect is extracted immediately each time it is found during the inspection operation through the following operations which are executed substantially in parallel.

Defects are classified (113-5) to add extracted defect information and defect classification information to a result output file.

An extracted defect image is added to a result output file dedicated to images or to a file.

Defect information such as locations of extracted defects is displayed on an operation screen.

Upon completion of the test on a wafer-by-wafer basis, the following operations are next executed substantially in parallel.

The result output file is closed and saved.

When the result of the test is requested through a communication from the outside, the result of the test is sent.

The wafer is removed.

When the inspection system is set to continuously test wafers, the next wafer under inspection is transferred, followed by a repetition of the sequence of operations described above.

In the creation of recipes in FIG. 40, recipes created therein include a file for setting conditions associated with the test, and the like. The recipes can be saved as well, so that the recipes may be used to set conditions at the time of or before a test. The conditions associated with the test described in the recipes include, for example, the following items: dies under inspection;

region to be tested within a die;

inspection algorithm;

detecting conditions (required for extracting defects, such as a test sensitivity); and observation conditions (magnification, lens voltages, stage speed, inspection order, and the like, which are required for observation).

Figure 41:
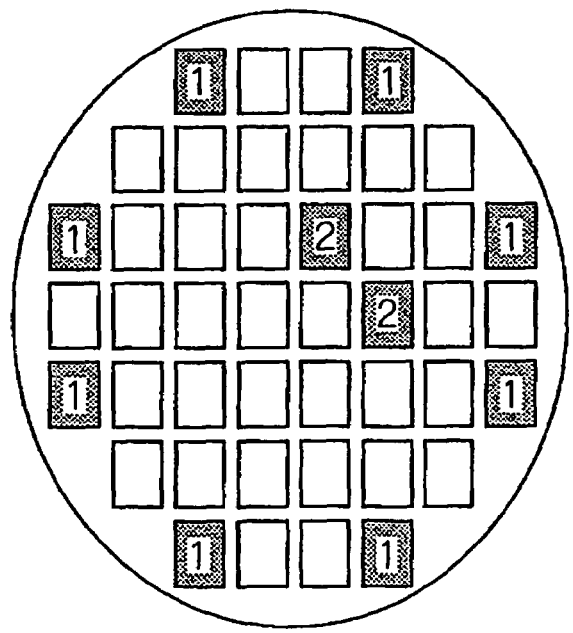
FIG. 41 is a diagram showing how dies under inspection are set.

Among the test conditions listed above, the setting of dies under inspection involves an operator specifying dies to be tested on a die map screen displayed on the operation screen, as illustrated in FIG. 41. In the example of FIG. 41, dies 1 near the periphery of the wafer and dies 2 clearly determined as defective in the pre-process are grayed out and removed from dies under inspection, and the remaining dies are subjected to the test. The alignment control unit 2 also has a function of automatically specifying dies under inspection based on the distance from the periphery of the wafer and information on good/fail of dies detected in the pre-process.

Figure 42:
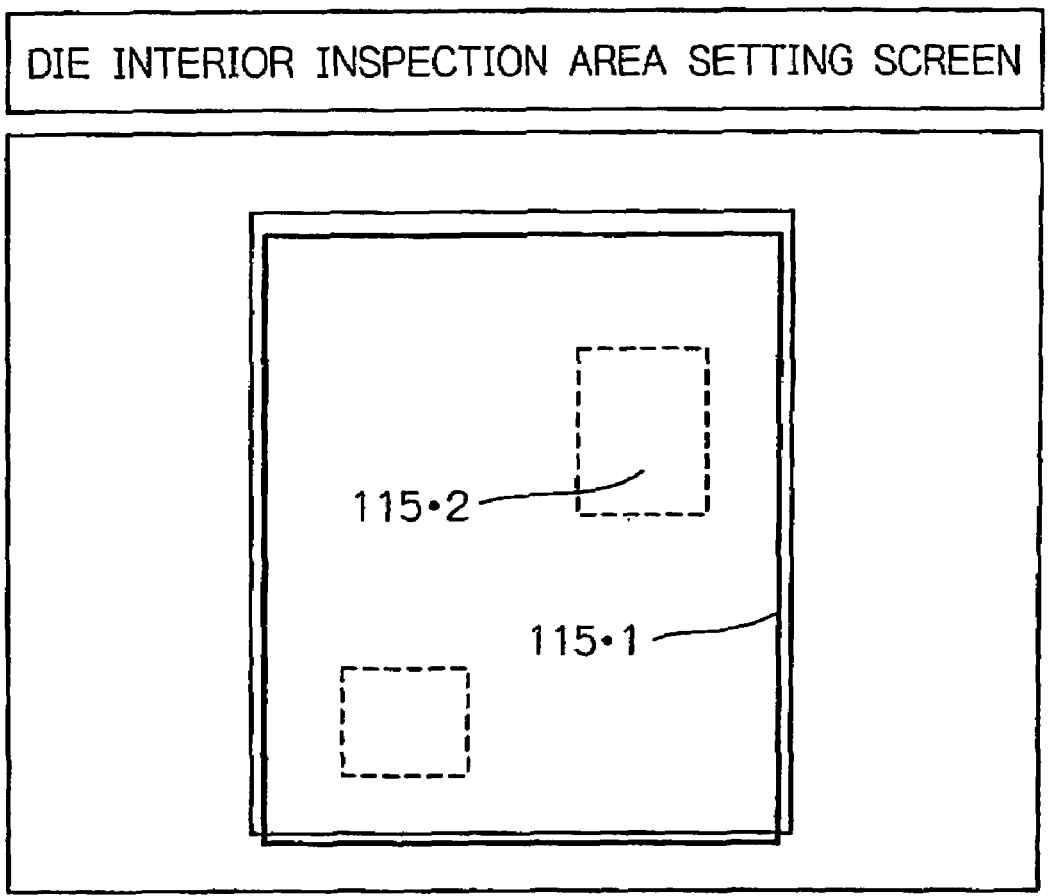
FIG. 42 is a diagram for explaining how a test is set within a die.

An area under inspection within a die is specified by the operator on a die internal test region setting screen displayed on the operation screen, as illustrated in FIG. 42, using an input device such as a mouse based on an image captured by an optical microscope or an EB microscope. In the example of FIG. 42, an area 115-1 indicated by a solid line, and an area 115-2 indicated by a broken line are set to be areas under inspection.

The area 115-1 includes substantially the entire die which is set to be under inspection. In this event, an adjacent die comparison method is employed for a test algorithm, and detailed detection conditions and observation conditions for this area are separately set. For the area 115-2, an array test is employed for a test algorithm, and detection conditions and detailed observation conditions for this area are separately set. Thus, a plurality of areas under inspection can be set, and an appropriate test algorithm and test sensitivity can be set for each of the areas. Also, some areas under inspection can be overlapped, so that different test algorithms can be simultaneously executed for the same area.

Figure 43:
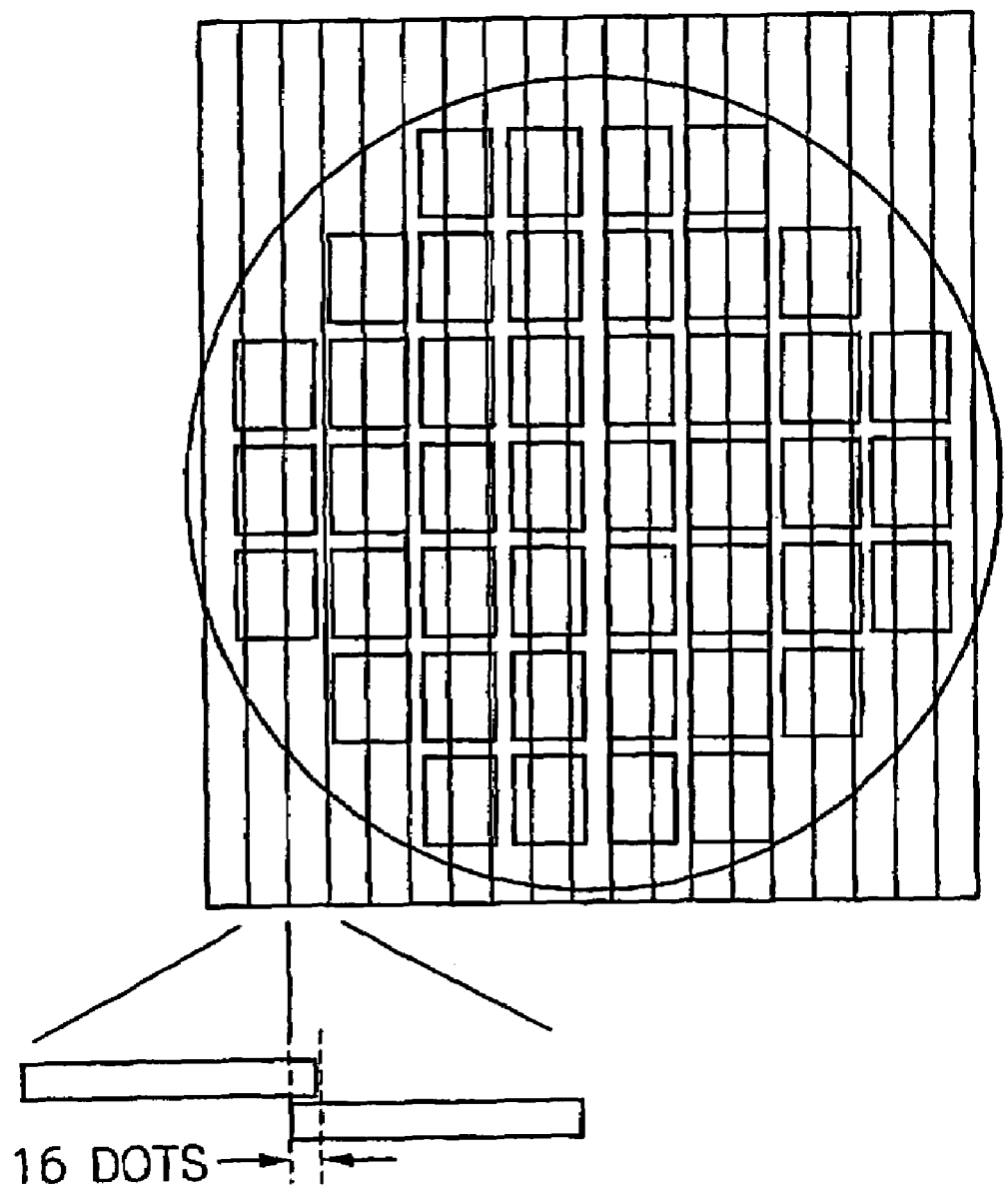
FIG. 43 is a diagram for explaining a semiconductor device inspection procedure.

In the inspection operation 113-4 in FIG. 40, a wafer under inspection is sectioned in scanning widths, as illustrated in FIG. 43. The scanning width is substantially determined by the length of a line sensor, but is set such that adjacent line sensors slightly overlap in their respective edge portions. This is intended to ensure a margin for determining the continuity between lines when detected defects are totally processed at a final stage, and for an alignment of images involved in a comparison test. An overlapping amount is approximately 16 dots for a 2,048-dot line sensor.

FIGS. 44(A) and 44(B) schematically illustrate scanning directions and sequences. Specifically, a bi-directional operation (Operation A) for reducing a test time, and a uni-directional operation (Operation B) due to mechanical restrictions can be selected by the operator.

Figure 45:
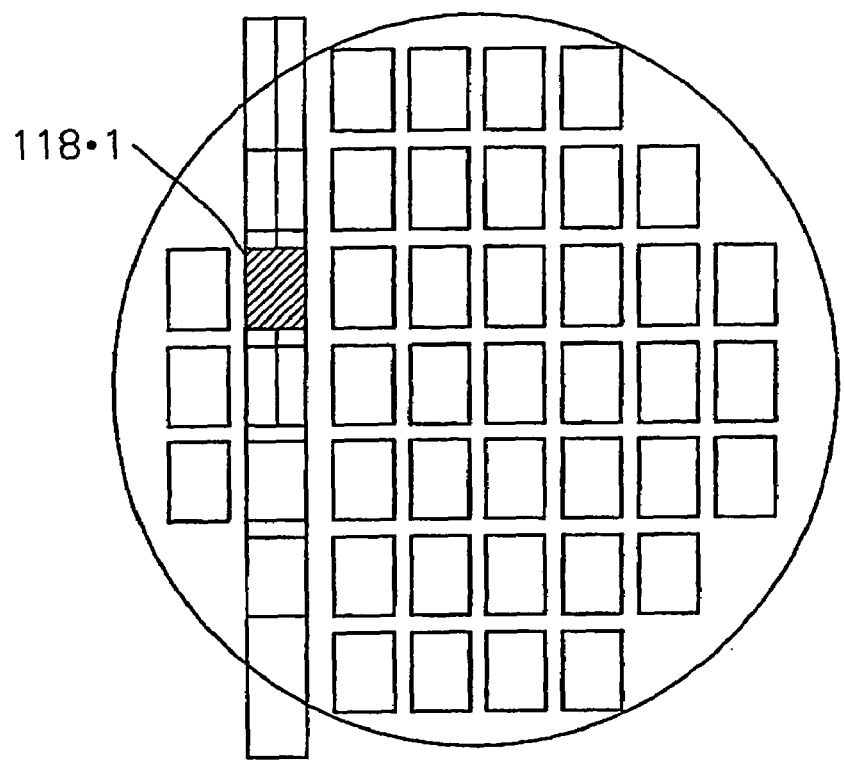
FIGS. 45(A) and 45(B) are diagrams showing how a wafer is scanned when there is one die under inspection on the wafer, and an exemplary die under inspection, respectively.
Figure 45:
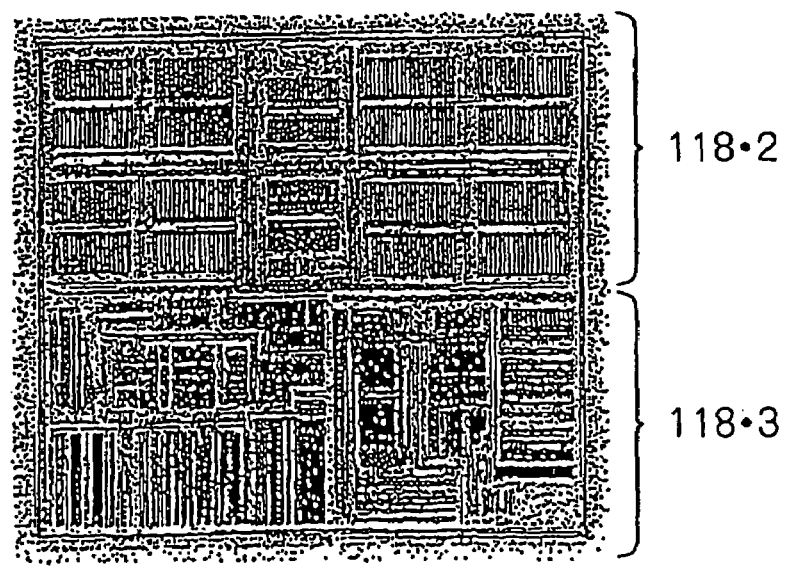

The control unit also has a function of automatically processing and detecting to execute an operation which reduces the amount of scanning for the test based on target die information stored in the recipe. FIG. 45(A) shows an example of scanning which is done when there is only one die under inspection, in which case unnecessary scanning is omitted.

A test algorithm set by the recipe can be classified into a cell test (array test) and a die test (random test).

As illustrated in FIG. 45(B), a die is divided into a cell area 118-2 which has a periodic structure mainly used for memories, and a random area 118-3 which does not have the periodic structure. Since the cell area 118-2 having the periodic structure includes a plurality of cells to be compared within the same die, the cells within the same die can be tested using the cell test by comparing them with one another. On the other hand, since the random area 118-3 cannot be compared within the same die, dies must be compared using the die test. The die test method is further classified as follows depending on what is compared:

Adjacent die comparison method (Die-to-Die test);
Reference die comparison method (Die-to-Any Die test); and
CAD data comparison method (Cad Data-to-Any Die test).

A scheme generally called a "golden template scheme" falls under the basic die comparison method and CAD data comparison method. In the reference die comparison method, a reference die is used as a golden template, while in the CAD data comparison method, CAD data is used as a golden template.

The following description will be made on the operation of the respective test algorithms.

Cell Test (Array Test)

The cell test is applied to a test of a periodic structure. A DRAM cell is an example which is suitable for the cell test.

The test involves comparing a reference image with an image under inspection, and extracting differences therebetween as defects. The reference image and image under inspection may be digitized images or multi-valued images for improving the detection accuracy.

While defects may be differences themselves between the reference image and the image under inspection, a secondary determination may be made in order to prevent erroneous detections based on difference information such as the amount of detected difference, a total area of pixels which present differences, and the like.

In the cell test, the comparison of the reference image with the image under inspection is made in units of structural periods. Specifically, they may be compared in units of structural periods while reading the images collectively captured by a CCD or the like, or when the reference image comprises n units of structural periods, the n units of structural period can be compared at the same time.

Figure 46:
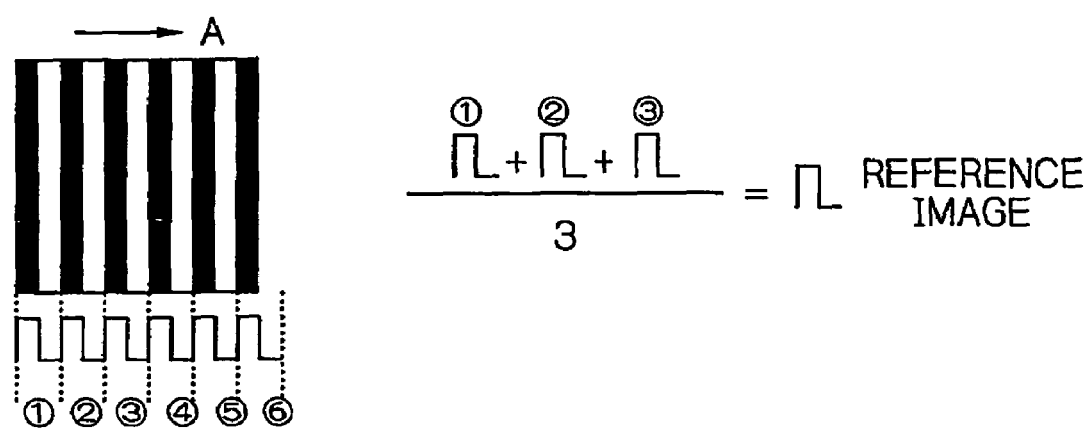
FIG. 46 is a diagram for explaining how a reference image is generated in the semiconductor device inspection procedure.

FIG. 46 illustrates an exemplary method of generating a reference image. FIG. 46 illustrates the generation of one structural period unit because the following description will be made on an exemplary comparison which is made on a unit-by-unit basis. The number of periods can be increased to n in the same method.

Assume that a test is conducted in a direction indicated by an arrow A in FIG. 46. Assume also that period 4 is chosen to be a period under inspection. Since the length of the period is entered by the operator while viewing the image, periods 1–6 can be readily recognized in FIG. 46.

The reference period image is generated by adding periods 1–3 immediately before the period under inspection and averaging them in each pixel. Even if a defect is found in any of periods 1–3, the influence is not significant because these periods are averaged. The reference period image thus generated is compared with the period image 4 under inspection to extract defects.

When a period image 5 under inspection is next tested, periods 2–4 are averaged to generate a reference period image. Subsequently, a period image under inspection is generated from images captured before the capturing of the period image under inspection in a similar manner to continue the test.

Die Test (Random Test)

The die test is applied without limited by the structure of die. The test involves comparing a reference image with an image under inspection, and extracting differences therebetween as defects. The reference image and image under inspection may be digitized images or multi-valued images for improving the detection accuracy. While defects may be differences themselves between the reference image and the image under inspection, a secondary determination may be made in order to prevent erroneous detections based on difference information such as the amount of detected difference, a total area of pixels which present differences, and the like. The die test can be classified according to how a reference image is generated. The following description will be made on the operation of an adjacent die comparison method, a reference die comparison inspection method, and a CAD data comparison method which are included in the die test.

A. Adjacent Die Comparison Method (Die-Die Test)

Figure 47:
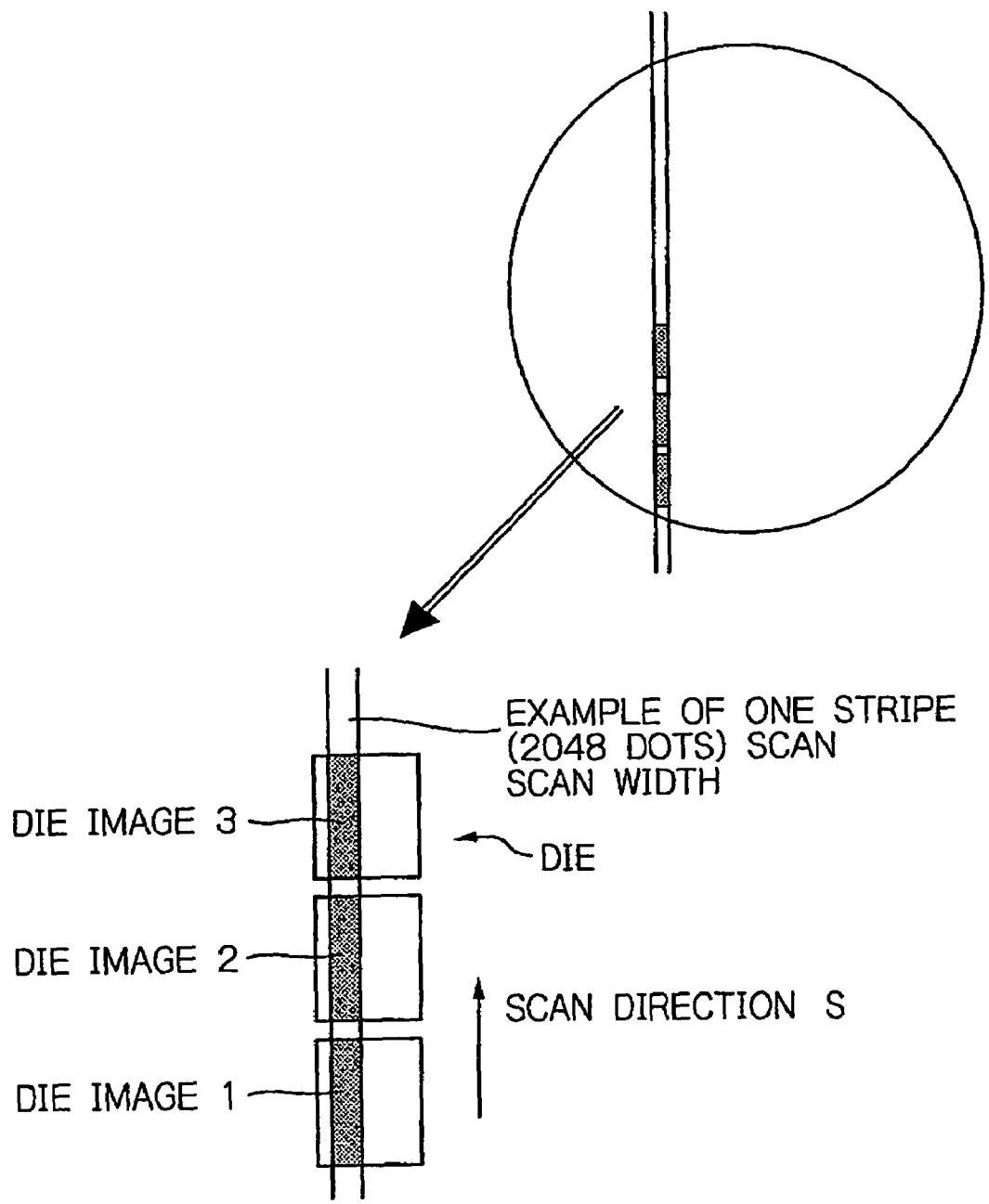
FIG. 47 is a diagram for explaining how adjacent dies are compared in the semiconductor device inspection procedure.

The reference image represents a die adjacent to an image under inspection. Two dies adjacent to the image under inspection are compared to determine a defect. Specifically, referring to FIGS. 47 and 48, the following steps are executed in a situation where a switch 121-4 and a switch 121-5 are set to connect a memory 121-1 and a memory 121-2 of an image processing apparatus are connected to a path 121-41 of a camera 121-3.

a) A step of storing a die image 1 from the path 121-41 to the memory 121-1 in accordance with a scanning direction S.

b) A step of storing a die image 2 from the path 121-41 to the memory 121-2.

c) A step of capturing the die image 2 from a path 121-42 simultaneously with the foregoing Step b), while comparing the capture die image 2 with image data stored in the memory 121-1 which is at the same relative position in the die to find differences.

d) A step of saving the differences found in Step c).

e) A step of storing a die image 3 from the path 121-41 to the memory 121-1.

f) A step of capturing the die image from the path 121-42 simultaneously with the foregoing Step e), while comparing the captured die image 3 with image data stored in the memory 121-2 which is at the same relative position in the die to find differences.

g) A step of saving the differences found in Step f).

h) A step of determining defects in the die image 2 from the result saved in Steps d) and g).

i) A step of subsequently repeating Steps a) to h) in consecutive dies.

Settings may be made to correct the two images to be compared such that a position alignment, i.e., a difference in position is eliminated in the two image before the differences are found in Steps c) and f). Alternatively, a correction may be made to eliminate density alignment, i.e., a difference density. In some cases, both processes may be required.

B. Reference Die Comparison Method (Die-Any Die Test)

Figure 50:
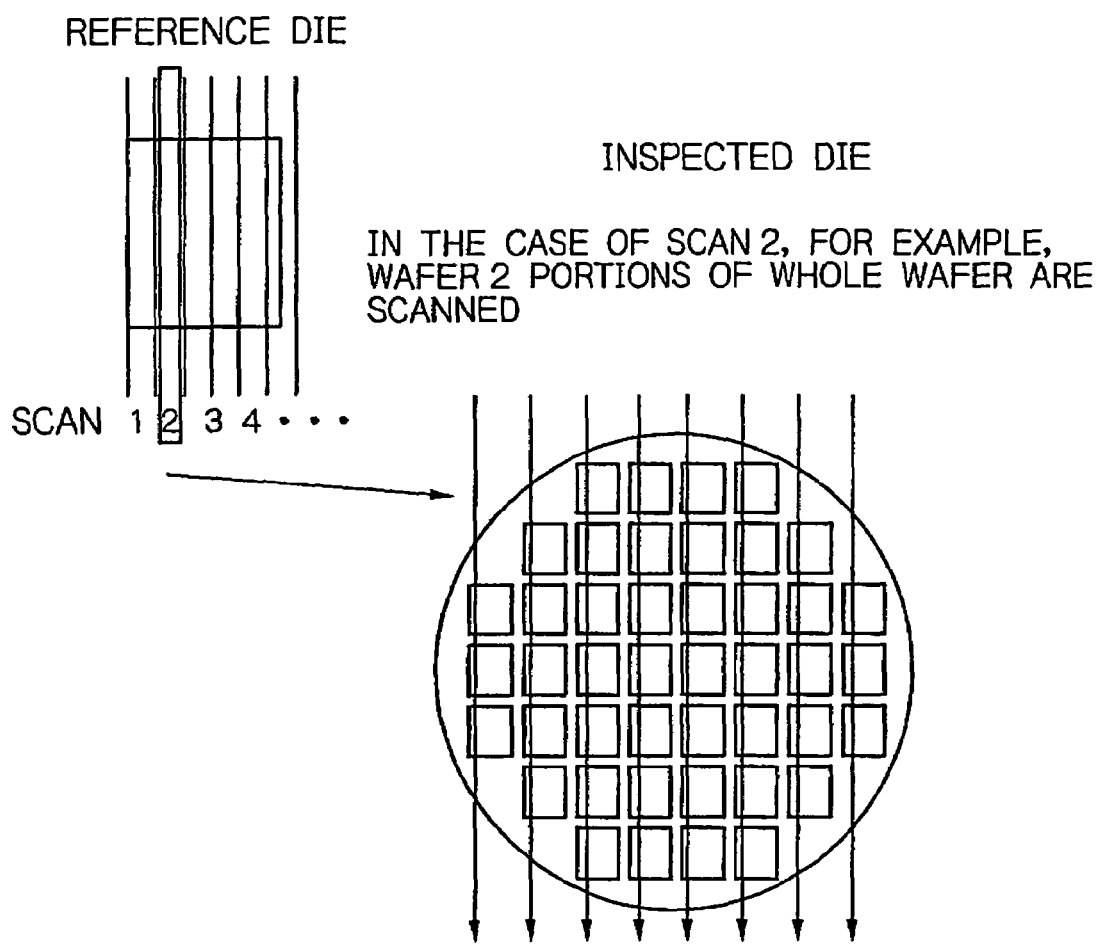
FIG. 50 is a diagram for explaining how adjacent dies are compared in the semiconductor device inspection procedure.

The operator specifies a reference die. The reference die is a die existing on a wafer, or a die image saved before the test. First, the reference die is scanned or transferred to wave its image in a memory for use as a reference image. Specifically, the following steps are executed in FIGS. 48 and 49.

a) A step of selecting the reference die by the operator from a die on a wafer under inspection or die images stored before the test.

b) A step of setting the switch 121-4 and switch 121-5 such that at least one of the memory 121-1 and memory 121-2 of an image processing apparatus is connected to a path 121-41 from a camera 121-3 when a reference die exists on the wafer under inspection.

c) A step of setting the switch 121-4 and switch 121-5 such that at least one of the memory 121-1 and memory 121-2 of the image processing apparatus is connected to a path 121-7 from a memory 121-7 which stores a reference image that is the die image when the reference die is a die image saved before the test.

d) A step of scanning the reference die, when it exists on the wafer under inspection, and transferring a reference image, which is a reference die image, to a memory of the image processing apparatus.

e) A step of transferring a reference image, which is a reference die image, to a memory of the image processing apparatus, without the need for scanning, when the reference die is a die image saved before the test.

f) A step of comparing an image generated by sequentially scanning the image under inspection, the image in the memory to which the reference image, i.e., the reference die image has been transferred, and image data which is at the same relative position in the die to find differences.

g) A step of determining defects from the differences found in the foregoing Step f).

h) A step of subsequently testing or inspecting the same portions for a scanning position of the reference die and the die origin of the die under inspection over the entire wafer, as illustrated in FIG. 50, and repeating the foregoing Steps d) to g) while changing the scanning position of the reference die until the entire die is tested.

Settings may be made to correct two images to be compared such that a position alignment, i.e., a difference in position is eliminated in the two images before the differences are found in Step f). Alternatively, a correction may be made to eliminate density alignment, i.e., a difference density. In some cases, both processes may be required.

The reference die image stored in the memory of the image processing apparatus in Step d) or e) may be the entire reference die, or a portion of the reference die which is updated.

C. CAD Data Comparison Method (CAD Data-Any Die Test)

A certain image is created for use as a reference image from CAD data which is the output of a CAD-based semiconductor pattern designing process. The reference image may represent an entire die, or part thereof which includes a portion under inspection.

This CAD data is typically vector data which cannot be used as the reference image unless the CAD data is converted to raster data equivalent to image data captured by a scanning operation. Thus, the following conversion process is executed in regard to the CAD data processing operation.

a) Vector data, which comprises the CAD data, is converted to raster data.

b) The foregoing step a) is performed in units of image scanning width which is known by scanning the die under inspection during a test.

c) The foregoing step b) converts image data which is at the same relative position in the die as an image which is expected to be captured by scanning the die under inspection.

d) The foregoing Step c) is performed while the test scanning is overlapped with the conversion operation.

While the foregoing Steps a)–d) are an exemplary sequence of making a conversion in units of image, scanning widths for faster processing, the test can be conducted without fixing the conversion unit to the image scanning width.

As an additional function to the operation for converting vector data to raster data, at least one of the following functions is provided.

a) A function of converting raster data to multi-value data.

b) A function of setting a gradation weight and an offset for the conversion to multi-value data in view of the sensitivity of the inspection apparatus in regard to the foregoing function a).

c) A function of processing an image for modifications such as expansion, reduction and the like after vector data has been converted to raster data.

Figure 48:
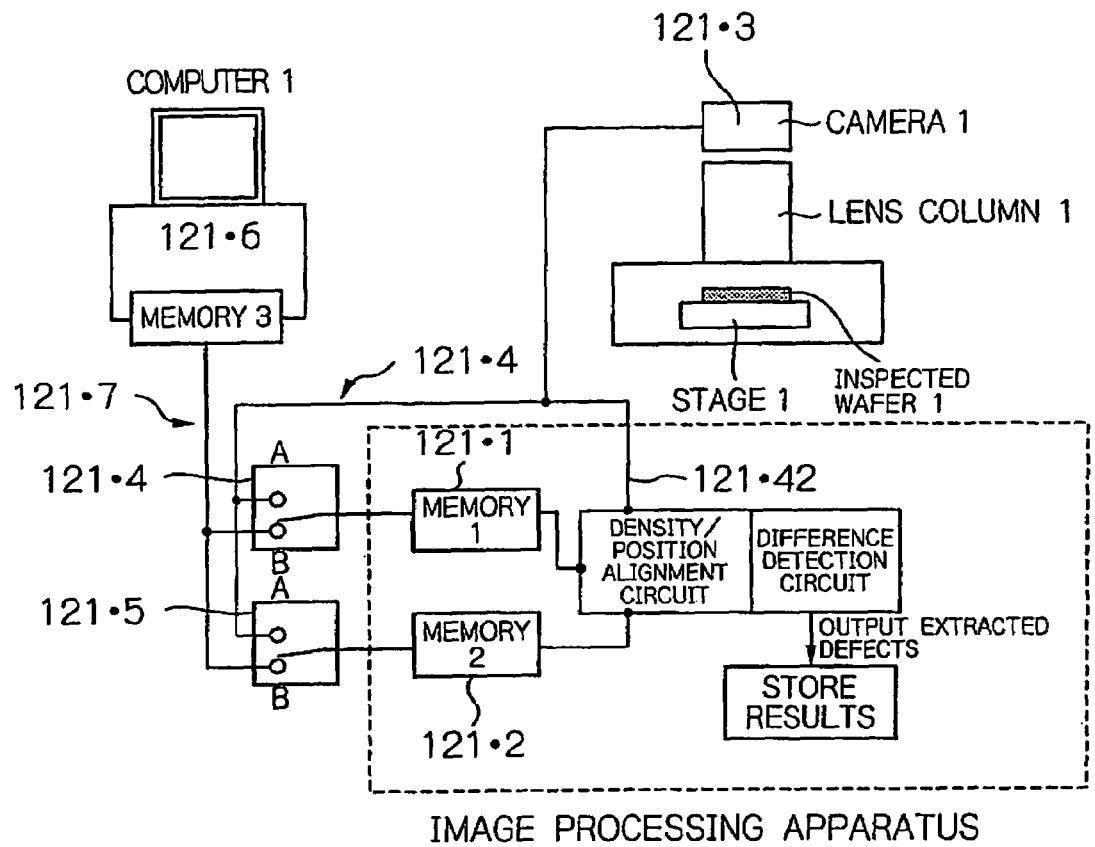
FIG. 48 is a diagram for explaining how adjacent dies are compared in the semiconductor device inspection procedure.
Figure 49:
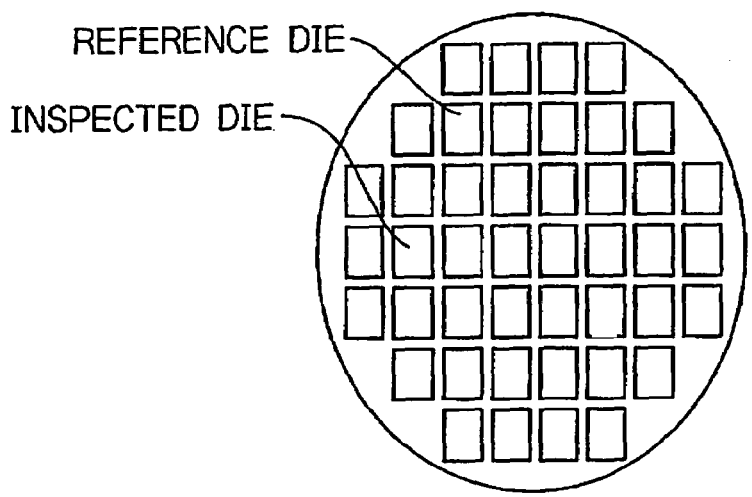
FIG. 49 is a diagram for explaining how adjacent dies are compared in the semiconductor device inspection procedure.

Inspection steps based on the CAD data comparison method executed in the system illustrated in FIG. 48 are as follows:

a) A step of converting CAD data to raster data in a computer 1, and generating a reference image and saving the reference image in the memory 121-6 with the aid of the foregoing additional function.

b) A step of setting the switch 121-4 and switch 121-5 such that at least one of the memory 121-1 and memory 121-2 of the image processing apparatus is connected to the path 121-7 from the memory 121-6.

c) A step of transferring the reference image in the memory 121-6 to a memory of the image processing apparatus.

d) A step of comparing an image generated by sequentially scanning the image under inspection, the image in the memory to which the reference image has been transferred, and image data which is at the same relative position in the die to find differences.

e) A step of determining defects from the differences found in the foregoing Step d).

f) A step of subsequently testing or inspecting the same portions for a scanning position of the reference die and the die origin of the die under inspection over the entire wafer, as illustrated in FIG. 50, and repeating the foregoing Steps a) to e) while changing the scanning position of the reference die until the entire die is tested.

Settings are made to correct two images to be compared such that a position alignment is made, i.e., a difference in position is eliminated in the two images before the differences are found in Step d). Alternatively, a correction is made to eliminate density alignment, i.e., a difference density. In some cases, both processes may be required.

The reference die image stored in the memory of the image processing apparatus in Step c) may be the entire reference die, or a portion of the reference die which may be tested while it is updated.

While the foregoing description has been made on the algorithms of the array test (cell test) for inspecting periodic structures, and the random test, the cell test and random test can be conducted simultaneously. Specifically, the cell area and random area are separately processed, wherein cells are compared with one another in a die in the cell area, and simultaneously, a comparison is made with adjacent dies, reference die, or CAD data-in the random area. By doing so, the inspection time can be largely reduced to improve the throughput.

In this event, inspection circuits for the cell area are preferably provided independently of one another. Also, if tests are not conducted simultaneously, a single inspection circuit may be provided with programs which can be switched for the cell test and random test, so that the comparison test can be conducted by switching the programs. Specifically, when patterns are tested with a plurality of processing algorithms applied thereto, these algorithms may be executed simultaneously with separate circuits provided therefor, or algorithms corresponding to them may be provided and switched by a single circuit for processing. In any case, this method can be applied as well when there is a plurality of types of cells which are compared with one another, and dies are compared with each other or with CAD data in the random section.

Figure 51:
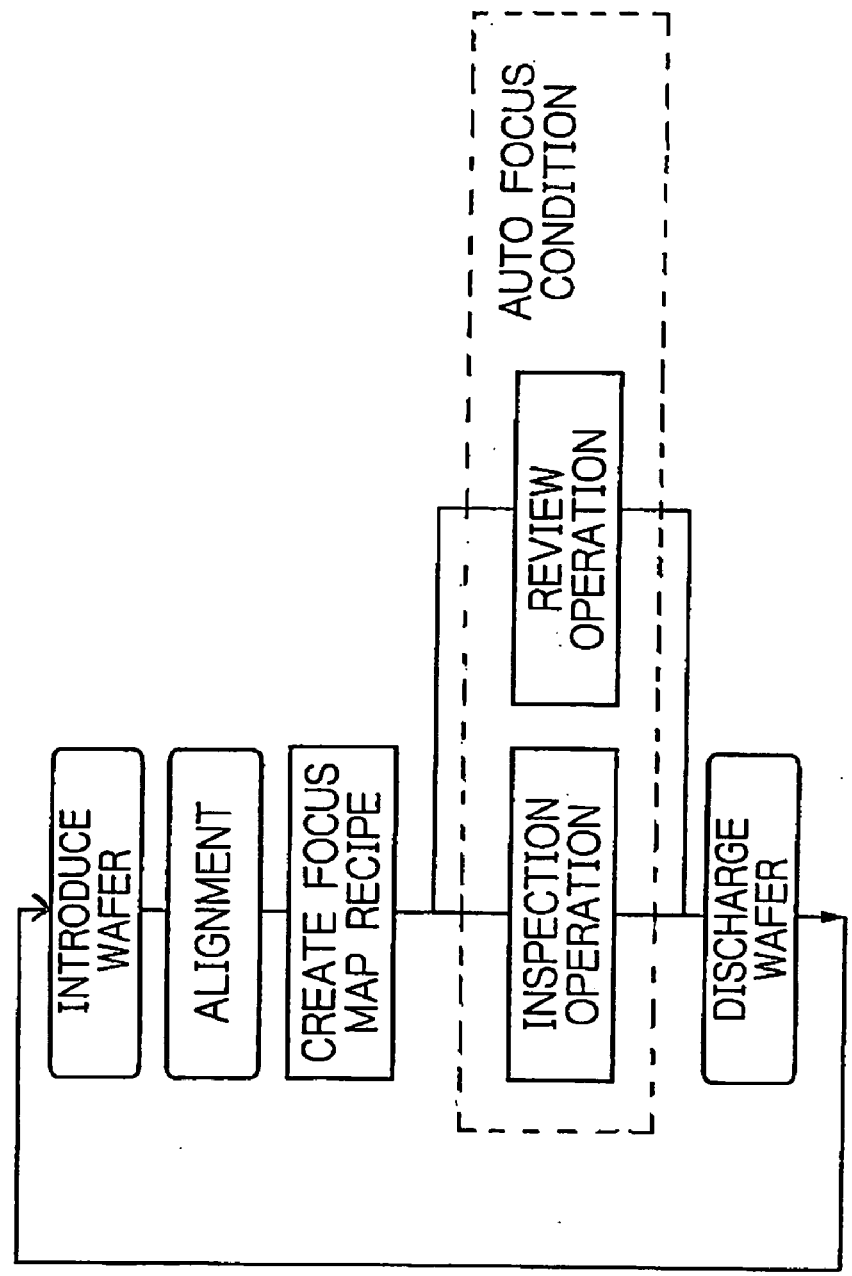
FIG. 51 is a diagram for explaining focus mapping in the semiconductor device inspection procedure.

FIG. 51 illustrates a basic flow of a focus function. First, after transferring a wafer including an alignment operation, recipes are created for setting conditions related to the test, and the like. One of the recipes is a focus map recipe which is relied on to perform an auto-focus operation during a inspection operation and a reviewing operation in accordance with focus information set therein. The following description will be made on a procedure of creating the focus map recipe, and a procedure of the auto-focus operation.

Figure 52:
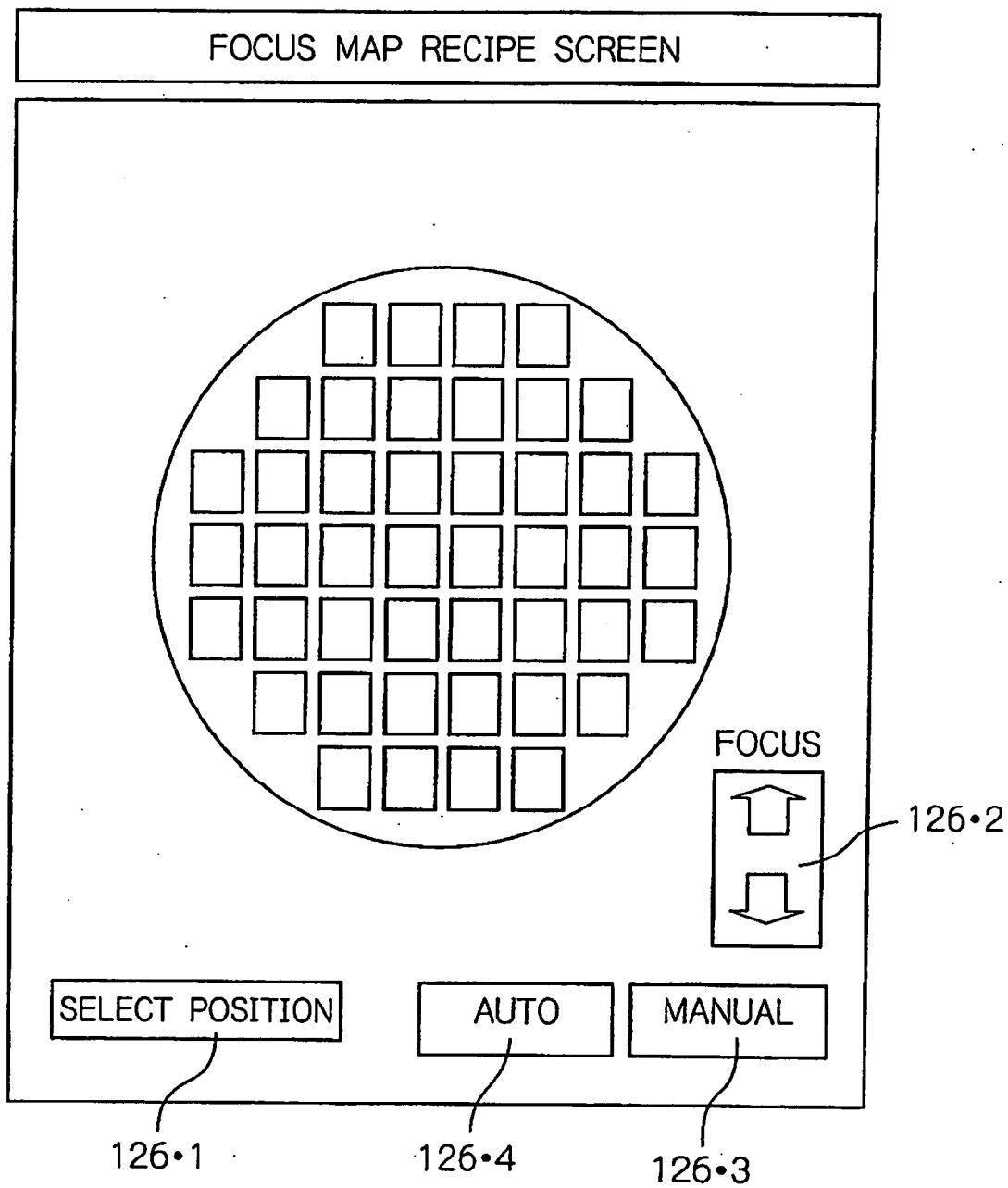
FIG. 52 is a diagram for explaining focus mapping in the semiconductor device inspection procedure.

In the following example, the focus map recipe has an independent input screen, and the operator executes the following steps to create the focus recipe. Such an input screen may be added to an input screen provided for different purposes.

a) A step of entering focus map coordinate representing the position of a die, a pattern within the die, or the like for which a focus value is entered using a switch 126-1 on a monitor screen illustrated in FIG. 52.

b) A step of setting a die pattern which is required for automatically measuring a focus value. This step may be skipped when the focus value is not automatically measured.

c) A step of setting a best focus value at the coordinate on the focus map determined at the foregoing Step a).

Among the foregoing steps, while the operator can specify an arbitrary die at Step a), other setting can also be made, such as a selection of all dies, a selection of every n die, and the like. In addition, the operator can select the input screen from any of a figure which schematically represents the arrangement of dies within a wafer and an image which uses an actual image.

At Step c), the operator manually selects a switch 126-3 in FIG. 52 and sets a focus value using a focus switch 126-2 which is associated with a voltage value provided to a focusing electrode, or select a switch 126-4 in FIG. 52 to automatically find a focus value to be supplied.

Figure 53:
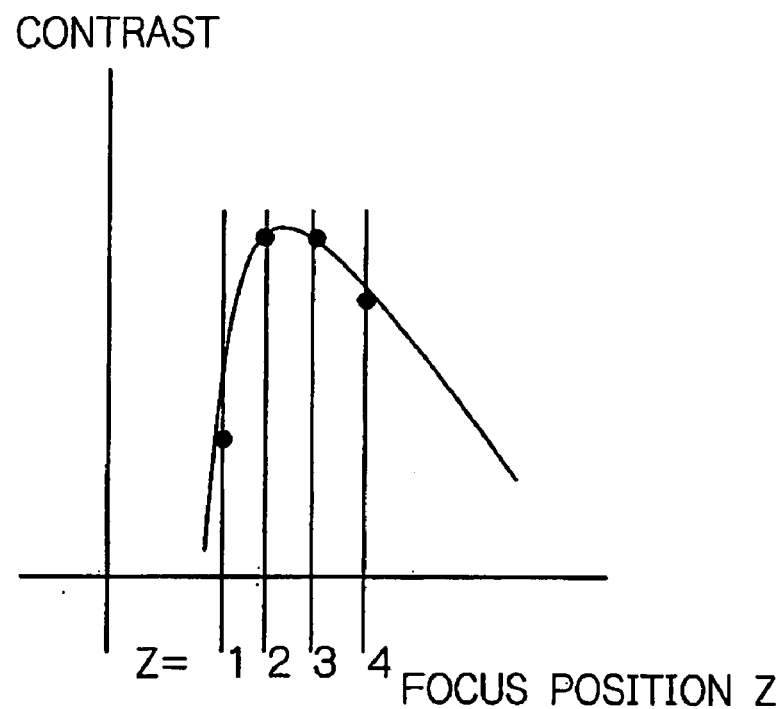
FIG. 53 is a diagram for explaining focus mapping in the semiconductor device inspection procedure.

A procedure for automatically finding a focus value at the forgoing Step c) involves, for example, the following steps:

a) finding an image with a focus position $Z=1$, and calculating the contrast thereof;

b) performing the foregoing Step a) while each of focus positions $Z=2$, 3, and 4;

c) regressing from the contrast values calculated at Steps a) and b) to find a contrast function (see FIG. 53); and d) calculating a Z value which results in a maximum value of the contrast function, and choosing it to be the best focus value.

Figure 54:
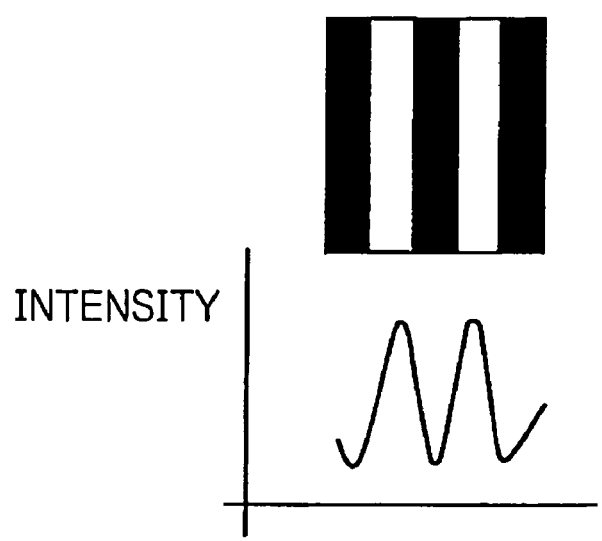
FIG. 54 is a diagram for explaining focus-mapping in the semiconductor device inspection procedure.

For example, a die pattern required for automatically measuring a focus value presents good results when a selected pattern consists of alternating lines and spaces as illustrated in FIG. 54, the contrast can be measured irrespective of the shape of a black and white pattern, whichever one is selected.

The single best focus value can be found by executing Steps a) to d). A data format in this event is (X, Y, Z), which is a combination of a set of the coordinate values X and Y at which the focus is found, and the best focus value Z. Therefore, there exist a number of focus map coordinates (X, Y, Z) determined by the focus map recipe. This is part of the focus map recipe, and is called a "focus map file."

A method of setting a focus to the best focus during a inspection operation for capturing an image and a reviewing operation, is implemented by the following steps.

a) Positional information is further sub-divided based on the focus map file 1 created during the creation of the focus map recipe, and the best focus at this time is calculated to create a sub-divided focus map file 2.

b) The calculation at Step a) is performed using an interpolation function.

c) The interpolation function at Step b) may be linear interpolation, spline interpolation or the like, and is specified by the operator upon creation of the focus map recipe.

d) The current X-Y position is monitored on the stage, and a voltage at the focus electrode is changed to a focus value described in the focus map file 2 suited to the current X-Y position.

Figure 55:
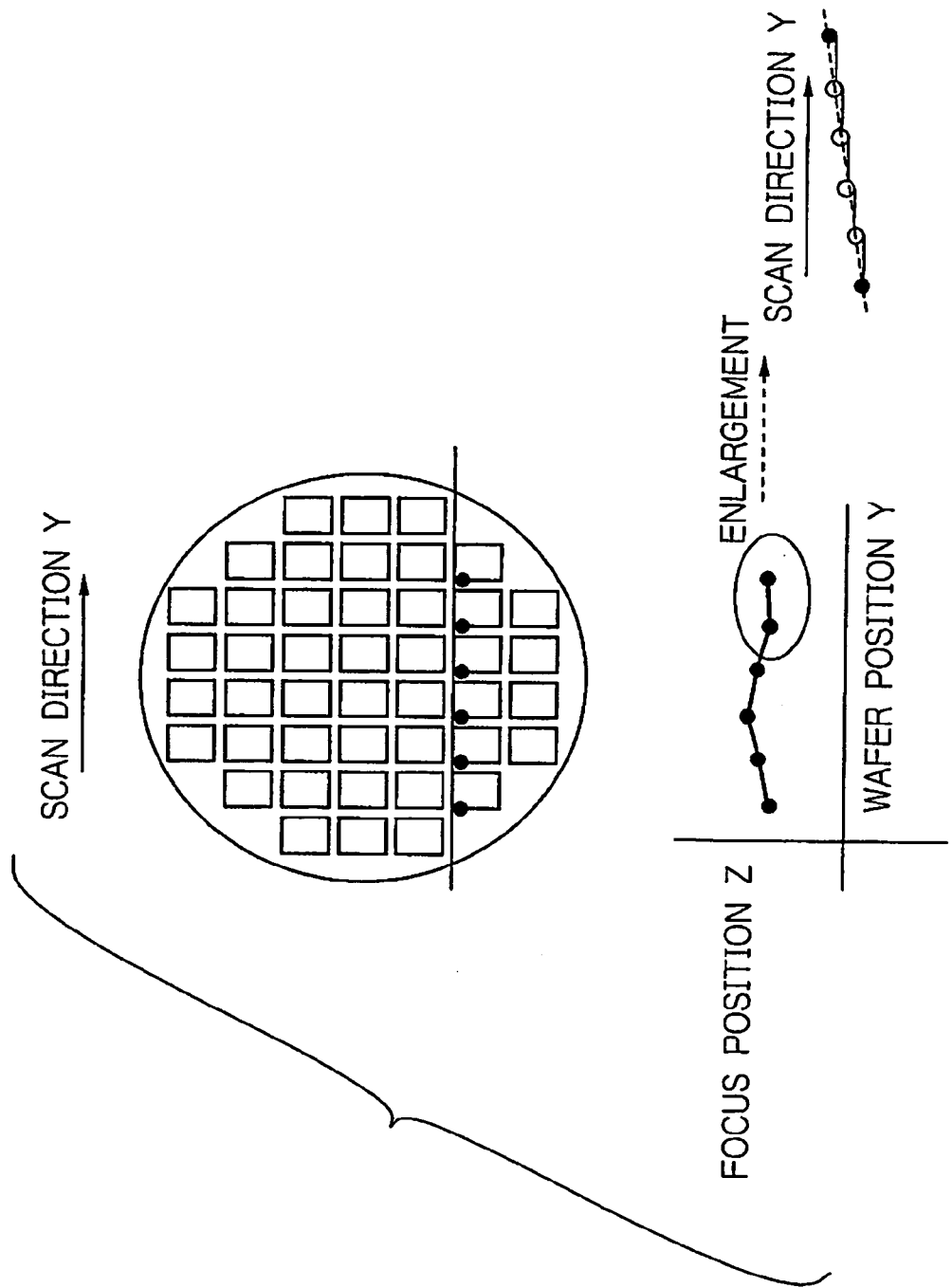
FIG. 55 is a diagram for explaining focus mapping in the semiconductor device inspection procedure.

Describing more specifically with reference to FIG. 55, a black circle represents a focus value of the focus map file 1, and a white circle represents a focus value of the focus map file 2, wherein:

1. focus values of the focus map file 2 are inserted between focus values of the focus map file 1; and
2. a focused position Z is varied following the scanning to maintain the best focus. In this event, the value of the preceding focus value is maintained between two white circles until the focus position is varied next time.

Figure 56:
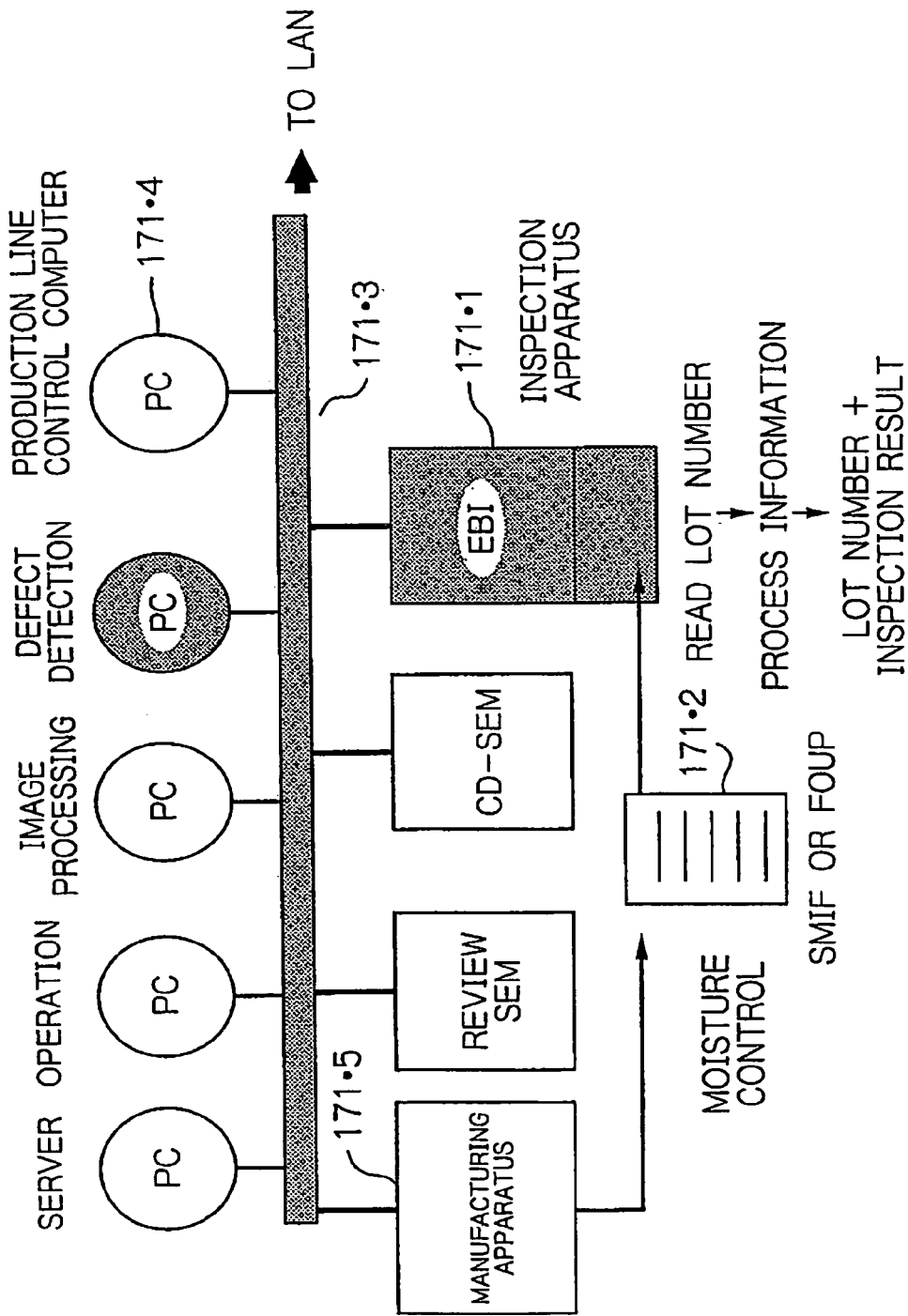
FIG. 56 is a block diagram illustrating an embodiment of a semiconductor manufacturing line system in which an electron beam apparatus according to the present invention is incorporated.

FIG. 56 illustrates an exemplary semiconductor manufacturing plant which employs the electron beam apparatus according to the present invention. In FIG. 56, the electron beam apparatus is designated by a reference numeral 171.1. Information such as a lot number of wafers to be tested by the electron beam apparatus, histories of manufacturing apparatuses, and the like are read from a memory included in SMIF or FOUP 171.2, or the lot number can be recognized by reading an ID number of the SMIF, FOUP 171.2 or a wafer cassette. During the transfer of wafers, the amount of moisture is controlled to prevent oxidization of metal wires and the like.

A PC 171.6 of a defect detector 171.1 for controlling a defect detection is connected to an information communication network 171-3 of a production line, so that information such as a lot number of wafers which are objects under inspection, and the result of their tests can be sent to a production line control computer 171-4, a variety of manufacturing apparatuses 171-5, and other inspection systems through the network 171-3. The manufacturing apparatuses 171-5 include those associated with lithography, for example, an exposure apparatus, a coater, a curing apparatus, a developer, and the like, an etching apparatus, deposition apparatuses such as a sputtering apparatus and a CVD apparatus, a CMP apparatus, a variety of measuring apparatuses, other inspection apparatus, and the like.

While the preferred embodiment of the present invention has been described in detail, it should be apparent to those skilled in the art that these modifications can be modified and altered without departing from the spirit and scope of the present invention.

What is claimed is:

1. An electron beam apparatus for evaluating a surface of a sample by detecting electrons having information on the sample surface generated by irradiation of a primary electron beam to the sample, comprising:

an electron gun for generating an electron beam;
a primary opto-electro system for setting the incident angle of the primary electron beam at the sample surface in a range of 70 degrees to 88 degrees;
an objective lens disposed near the sample for allowing the primary electron beam to pass through the objective lens; and
a detector for detecting the electrons having information on the sample surface.

2. An electron beam apparatus according to claim 1, wherein the primary opto-electro system is adapted to simultaneously direct a plurality of primary electron beams toward an observation spot on the sample surface.

3. An electron beam apparatus according to claim 2, wherein the primary opto-electro system is adapted to axially symmetrically irradiate a plurality of primary electron beams toward an observation spot on the sample surface.

4. An electron beam apparatus according to claim 1, wherein the primary opto-electro system is adapted to simultaneously direct a plurality of primary electron beams toward the sample surface, wherein at least one of the primary electron beams is directed in front of the observation spot in a scanning direction for pre-charge irradiation.

5. An electron beam apparatus according to claim 1, wherein the detector is located on a line perpendicular to the sample surface.

6. An electron beam apparatus according to claim 1, wherein the primary opto-electro system comprises a deflector for setting an incident angle of the primary electron beam into the sample surface by controlling a magnetic field or an electric field.

7. An electron beam apparatus according to claim 6, wherein the deflector is formed in a sector shape.

8. An electron beam apparatus according to claim 1, wherein the primary opto-electro system comprises means for forming a crossover on an optical axis of a secondary opto-electro system before irradiating the primary optical beam onto the sample surface.

9. An electron beam apparatus according to claim 1, wherein the electron gun comprises a cathode using a cold cathode source made of a carbon nano tube.

10. An electron beam apparatus according to claim 1, further comprising:

a sample stage having an electrostatic chuck for holding the sample through absorption; and
voltage applying means for applying the sample with a retarding voltage.

11. An electron beam apparatus according to claim 10, wherein the electrostatic chuck comprises an ampere meter for confirming that the sample is in a conducting condition before the retarding voltage is applied to the sample.

12. A semiconductor device manufacturing method comprising the step of evaluating a wafer in the middle or after completion of a process using the electron beam apparatus according to claim 1.

* * * * *

UNITED STATES PATENT AND TRADEMARK OFFICE
CERTIFICATE OF CORRECTION

| | | |
|---|---|---|
| PATENT NO. | : 7,176,459 B2 | Page 1 of 1 |
| APPLICATION NO. | : 10/999124 | |
| DATED | : February 13, 2007 | |
| INVENTOR(S) | : Kenji Watanabe et al. | |

It is certified that error appears in the above-identified patent and that said Letters Patent is hereby corrected as shown below:

<u>On the title page, Item (30) Foreign Application Priority Data</u>

Please insert -- Jan. 8, 2004 (JP) ... 2004-003202--.

Signed and Sealed this

Twenty-sixth Day of June, 2007

JON W. DUDAS
*Director of the United States Patent and Trademark Office*